US012692611B2

(12) United States Patent
Feng et al.

(10) Patent No.: US 12,692,611 B2
(45) Date of Patent: Jul. 28, 2026

(54) APPARATUSES, SYSTEMS, AND METHODS FOR GENERATING NITRIC OXIDE

(71) Applicant: Nanjing Novlead Biotechnology Co., Ltd., Nanjing (CN)

(72) Inventors: Zhichun Feng, Nanjing (CN); Wen Mao, Nanjing (CN); Yuyan Zhang, Nanjing (CN); Xiang Geng, Nanjing (CN); Tao Chen, Nanjing (CN); Yangbo Zhao, Nanjing (CN); Qing Wu, Nanjing (CN)

(73) Assignee: Nanjing Novlead Biotechnology Co., Ltd., Nanjing (CN)

( * ) Notice: Subject to any disclaimer, the term of this patent is extended or adjusted under 35 U.S.C. 154(b) by 660 days.

(21) Appl. No.: 18/043,900

(22) PCT Filed: Dec. 17, 2021

(86) PCT No.: PCT/CN2021/139117
§ 371 (c)(1),
(2) Date: Mar. 2, 2023

(87) PCT Pub. No.: WO2022/127902
PCT Pub. Date: Jun. 23, 2022

(65) Prior Publication Data
US 2023/0313399 A1 Oct. 5, 2023

(30) Foreign Application Priority Data

Dec. 18, 2020 (CN) .......................... 202011502839.7
Dec. 18, 2020 (CN) .......................... 202011502846.7
(Continued)

(51) Int. Cl.
*A61M 16/00* (2006.01)
*A61M 16/20* (2006.01)
(Continued)

(52) U.S. Cl.
CPC ......... *C25B 15/087* (2021.01); *A61M 16/202* (2014.02); *C25B 1/01* (2021.01);
(Continued)

(58) Field of Classification Search
CPC .. A61M 16/202; A61M 16/12; A61M 16/125; A61M 16/10; A61M 16/1005;
(Continued)

(56) References Cited

U.S. PATENT DOCUMENTS

| | | | |
|---|---|---|---|
| 5,827,420 A | 10/1998 | Shirazi et al. | |
| 2003/0062043 A1 | 4/2003 | Fine et al. | |
| 2015/0258299 A1* | 9/2015 | Flanagan | A61M 16/122 |
| | | | 128/202.16 |

FOREIGN PATENT DOCUMENTS

| | | | | |
|---|---|---|---|---|
| WO | WO 2018/191364 | 4/2017 | | |
| WO | WO-2018191364 A1 * | 10/2018 | | A61M 1/1698 |

OTHER PUBLICATIONS

International Search Report, dated Apr. 13, 2022, regarding International Application No. PCT/CN2021/139117, 11 pages.

* cited by examiner

*Primary Examiner* — Margaret M Luarca
*Assistant Examiner* — Sarah B Lederer
(74) *Attorney, Agent, or Firm* — Sheppard, Mullin, Richter & Hampton LLP

(57) ABSTRACT

Embodiments of nitric oxide (NO) generation apparatuses, systems, and methods are provided. In some embodiments, an NO generation apparatus may include a reaction chamber having a liquid region and a gas region. The liquid region may be configured to contain a reaction medium and the gas region may be configured to contain a product gas comprising NO. The NO generation apparatus may also include a plurality of electrodes disposed in the reaction medium, and may include an energy source electrically connected to the (Continued)

plurality of electrodes and configured to apply a predetermined voltage or a predetermined current to at least one of the plurality of electrodes to generate NO. The NO generation apparatus may also include an inlet circuit configured to receive a carrier gas, and may include at least one sparger in fluid communication with the inlet circuit and configured to emanate bubbles of the carrier gas in the reaction medium.

21 Claims, 17 Drawing Sheets

(30)         Foreign Application Priority Data

| | | |
|---|---|---|
| Dec. 18, 2020 | (CN) | .......................... 202011502862.6 |
| Dec. 18, 2020 | (CN) | .......................... 202011508948.X |
| Dec. 18, 2020 | (CN) | .......................... 202023064800.X |
| Dec. 18, 2020 | (CN) | .......................... 202023064847.6 |
| Dec. 18, 2020 | (CN) | .......................... 202023064866.9 |
| Dec. 18, 2020 | (CN) | .......................... 202023072485.5 |
| Dec. 18, 2020 | (CN) | .......................... 202023072503.X |
| Feb. 8, 2021 | (CN) | .......................... 202110183873.X |
| Feb. 8, 2021 | (CN) | .......................... 202120353644.4 |
| Feb. 8, 2021 | (CN) | .......................... 202120353650.X |

(51) Int. Cl.
  *C25B 1/01* (2021.01)
  *C25B 15/08* (2006.01)
  *F17C 1/00* (2006.01)
  *A61M 16/10* (2006.01)

(52) U.S. Cl.
  CPC .............. *C25B 15/085* (2021.01); *F17C 1/00* (2013.01); *A61M 2016/0033* (2013.01); *A61M 2016/1025* (2013.01); *A61M 2202/0275* (2013.01); *F17C 2205/0332* (2013.01); *F17C 2221/01* (2013.01); *F17C 2250/0636* (2013.01); *F17C 2250/0647* (2013.01); *F17C 2270/025* (2013.01)

(58) Field of Classification Search
  CPC .......... A61M 16/00; A61M 2016/1025; A61M 2202/0275
  See application file for complete search history.

$$y = 36.09x - 31.759$$
$$R^2 = 0.9999$$

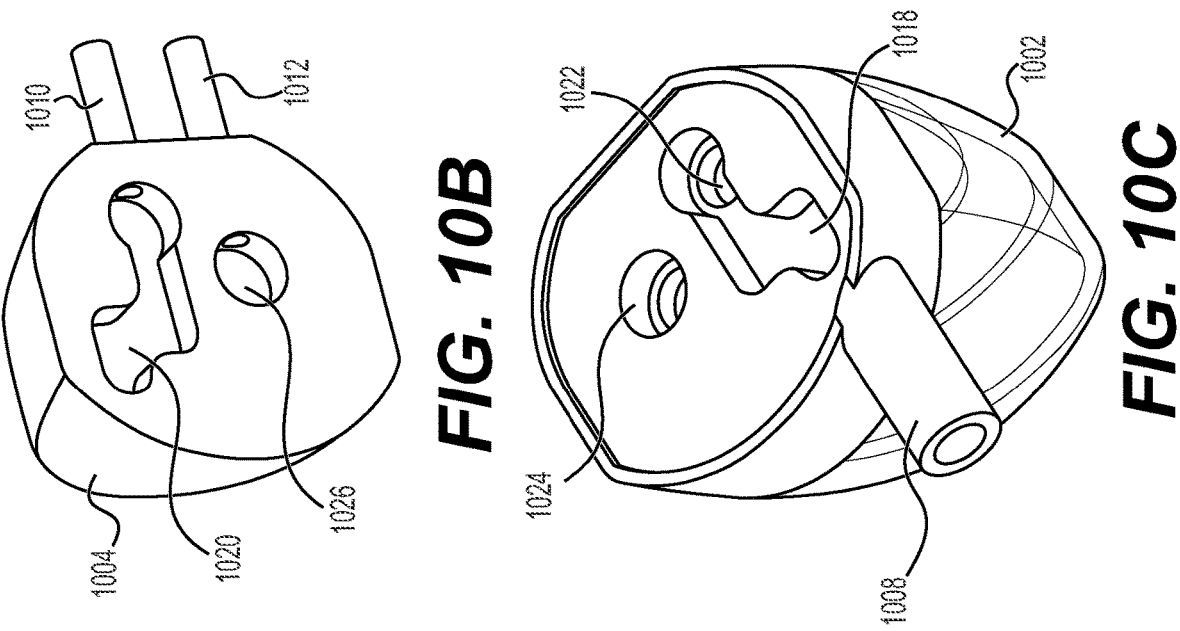
*FIG. 10B*
*FIG. 10C*
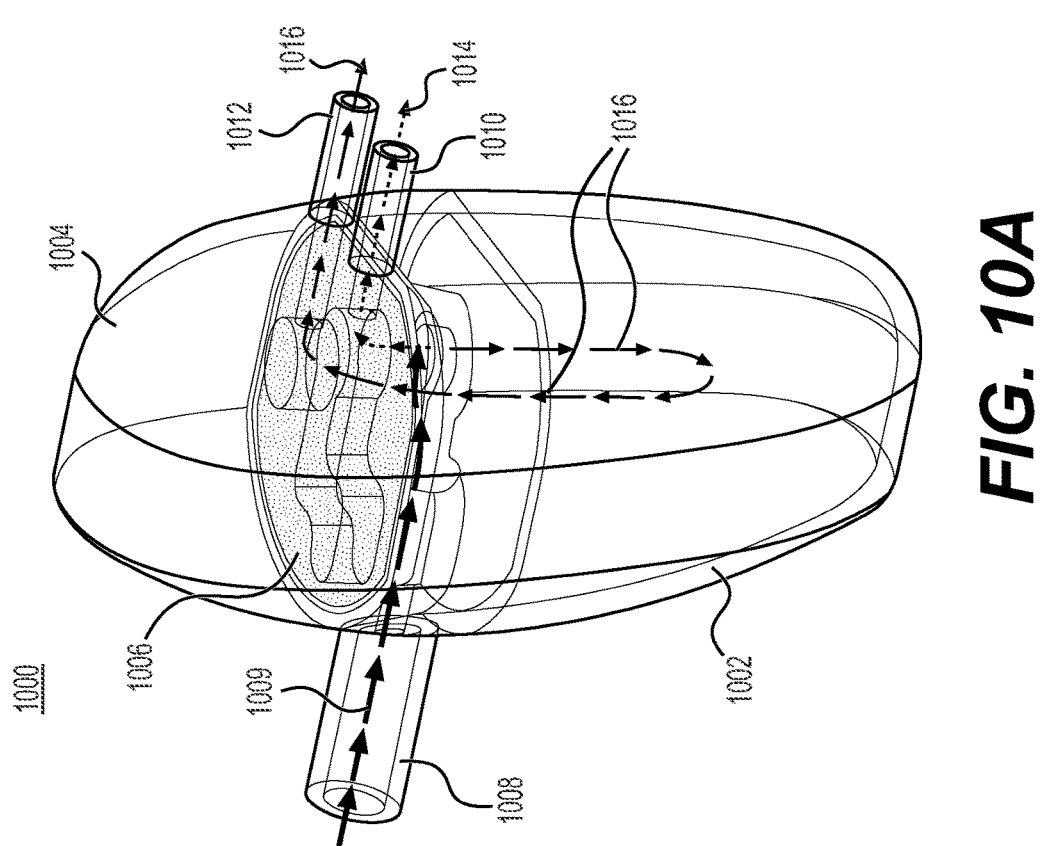
*FIG. 10A*

NO GENERATION METHOD 1200

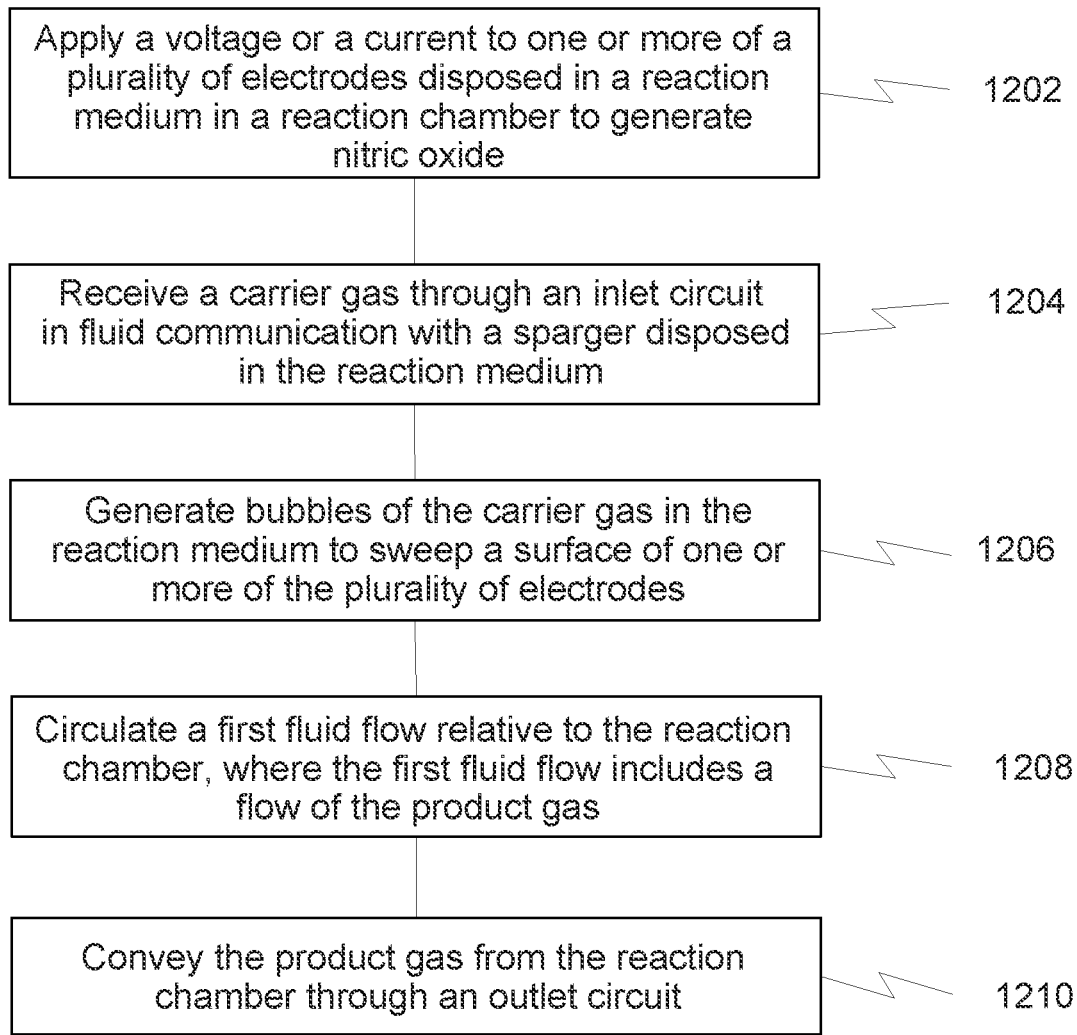

| Apply a voltage or a current to one or more of a plurality of electrodes disposed in a reaction medium in a reaction chamber to generate nitric oxide | 1202 |

| Receive a carrier gas through an inlet circuit in fluid communication with a sparger disposed in the reaction medium | 1204 |

| Generate bubbles of the carrier gas in the reaction medium to sweep a surface of one or more of the plurality of electrodes | 1206 |

| Circulate a first fluid flow relative to the reaction chamber, where the first fluid flow includes a flow of the product gas | 1208 |

| Convey the product gas from the reaction chamber through an outlet circuit | 1210 |

FIG. 12

APPARATUSES, SYSTEMS, AND METHODS FOR GENERATING NITRIC OXIDE

CROSS-REFERENCE TO RELATED APPLICATIONS

This application is a U.S. National Stage Application under 35 U.S.C. 371 of International Application PCT/CN2021/139117, filed Dec. 17, 2021, which claims the benefit of priority of Chinese Patent Application No. 202011502839.7, filed Dec. 18, 2020, Chinese Patent Application No. 202011502846.7, filed Dec. 18, 2020, Chinese Patent Application No. 202011502862.6, filed Dec. 18, 2020, Chinese Patent Application No. 202011508948.X, filed Dec. 18, 2020, Chinese Patent Application No. 202023064800.X, filed Dec. 18, 2020, Chinese Patent Application No. 202023064847.6, filed Dec. 18, 2020, Chinese Patent Application No. 202023064866.9, filed Dec. 18, 2020, Chinese Patent Application No. 202023072485.5, filed Dec. 18, 2020, Chinese Patent Application No. 202023072503.X, filed Dec. 18, 2020, Chinese Patent Application No. 202110183873.0, filed Feb. 8, 2021, Chinese Patent Application No. 202120353644.4, filed Feb. 8, 2021, Chinese Patent Application No. 202120353650.X, filed Feb. 8, 2021, all of which are incorporated herein by reference in their entireties.

TECHNICAL FIELD

This present disclosure relates to apparatuses, systems, and methods for generating and/or delivering nitric oxide, and more particularly to apparatuses, systems, and methods for generating and/or delivering nitric oxide on demand.

BACKGROUND

Nitric oxide (NO) is a gaseous signaling molecule that plays important roles in many physiological and pathological processes. NO may diffuse through cell membranes without an intermediary transport mechanism and thus can signal neighboring cells or tissue in an efficient and fast manner. For example, NO produced by vascular endothelial cells can signal the surrounding vascular smooth muscles to relax, resulting in vasodilation and increased blood flow. NO may also participate in electron transfer and redox reactions in cellular biochemical events in human bodies. NO may elicit various physiological effects, such as endothelium-dependent vasodilation, by activating guanylyl cyclase.

Inhalation of NO may improve the body's oxidative capacity and reduce the need for high-risk extracorporeal cardiopulmonary support for critically ill patients. Controlled administration of appropriate amounts of inhaled NO may reduce pulmonary hypertension and improve oxygenation. Inhaled NO as a medicine has been approved by the U.S. Food and Drug Administration for treating persistent pulmonary hypertension in newborns. NO inhalation therapies have also been used in various diseases or clinical medicine fields, such as neonatal respiratory disorders, critical care medicine, cardiothoracic surgery, acute respiratory distress, and anesthesiology.

In clinical settings, high-pressure gas tanks or cylinders are used for providing NO. Such tanks are of significant size and weight and are typically secured to a wheeled delivery device or cart, typically to be placed at the bedside in a crowded intensive care unit. Using such heavy and bulky gas tanks may pose safety risks to the patients and healthcare workers. For example, patients and healthcare workers may be exposed to toxic nitrogen dioxide formed during system setup or due to potential NO leaks from damaged regulators, valves, or supply lines. Healthcare workers may also suffer from physical injury associated with moving or exchanging tanks. Therefore, there is a need to overcome and/or address one or more of these shortcomings. The present disclosure is related to a tank-free or "tankless" systems and methods that may generate NO on-demand, on an as-needed basis without the need to store large volumes of pressurized NO.

SUMMARY

According to some embodiments of the present disclosure, an apparatus for generating nitric oxide (NO) is provided. In some embodiments, the apparatus may include a reaction chamber having a liquid region and a gas region. The liquid region may be configured to contain a reaction medium. The gas region may be configured to contain a product gas comprising NO. In some embodiments, the apparatus may include a plurality of electrodes disposed in the reaction medium. The plurality of electrodes may include a cathode. In some embodiments, the apparatus may include an energy source electrically connected to the plurality of electrodes. The energy source may be configured to apply a predetermined voltage or a predetermined current to the cathode to generate NO. In some embodiments, the apparatus may include a sparger disposed in the reaction medium. In some embodiments, the apparatus may include an inlet circuit. The inlet circuit may be in fluid communication with the sparger and configured to convey a carrier gas to the sparger. In some embodiments, the apparatus may include an outlet circuit. The outlet circuit may be in fluid communication with the gas region of the reaction chamber and configured to convey the product gas from the reaction chamber. In some embodiments, the apparatus may include a first circulation circuit configured to circulate a first fluid flow relative to the reaction chamber. The first circulation circuit may include a first inlet in fluid communication with the gas region of the reaction chamber, a first outlet in fluid communication with the sparger, and a first pump configured to create the first fluid flow from the first inlet to the first outlet.

According to an embodiment of the present disclosure, a method for generating nitric oxide is provided. In some embodiments, the method may include applying, by an energy source, a predetermined voltage or a predetermined current to one or more of a plurality of electrodes. The plurality of electrodes may be disposed in a reaction medium contained in a reaction chamber to generate NO. The plurality of electrodes may include a cathode. The reaction chamber may include a gas region and a liquid region. The liquid region may be configured to contain the reaction medium. The gas region may be configured to contain a product gas comprising NO. In some embodiments, the method may include receiving a carrier gas through an inlet circuit. The inlet circuit may be in fluid communication with a sparger disposed in the reaction medium. In some embodiments, the method may include emanating, by the sparger, bubbles of the carrier gas in the reaction medium. The bubbles may sweep a surface of one or more of the plurality of electrodes. In some embodiments, the method may include circulating, in a first circulation circuit, a first fluid flow relative to the reaction chamber. The first fluid flow may include a flow of the product gas. In some embodiments, the method may include conveying the product gas from the reaction chamber through an outlet circuit. The outlet circuit may be in fluid communication with the gas region of the reaction chamber.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of certain disclosed embodiments as set forth in the accompanying claims.

BRIEF DESCRIPTION OF THE DRAWINGS

FIG. 10A a perspective view of a moisture collector, according to some embodiments of the present disclosure.

FIG. 10B a partial perspective view of the moisture collector of FIG. 10A.

4

FIG. 10C another partial perspective view of the moisture collector of FIG. 10A.

Figure 11A:
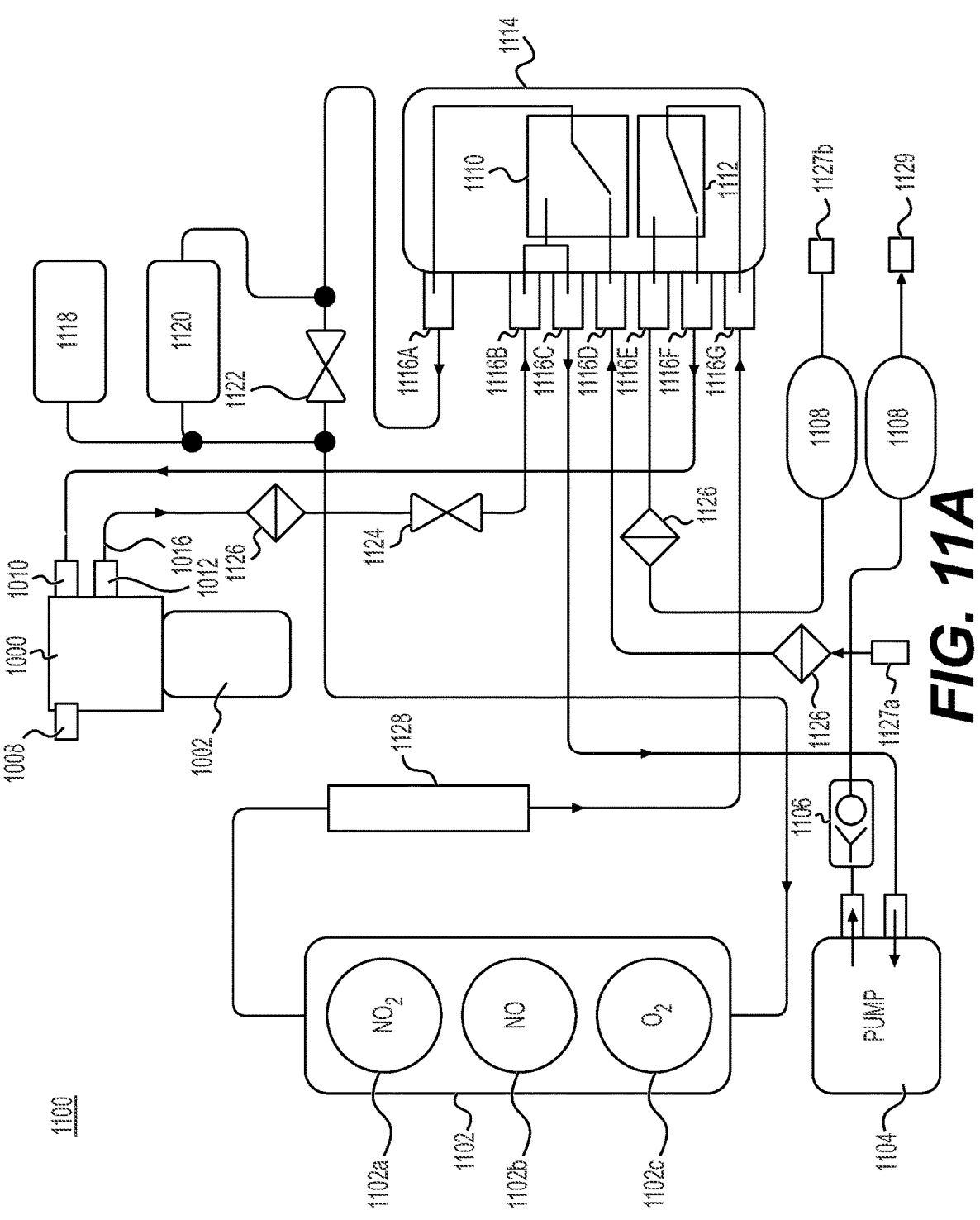

FIG. 11A a schematic representation of a sampling process of a gas monitoring device, according to some embodiments of the present disclosure.

Figure 11B:
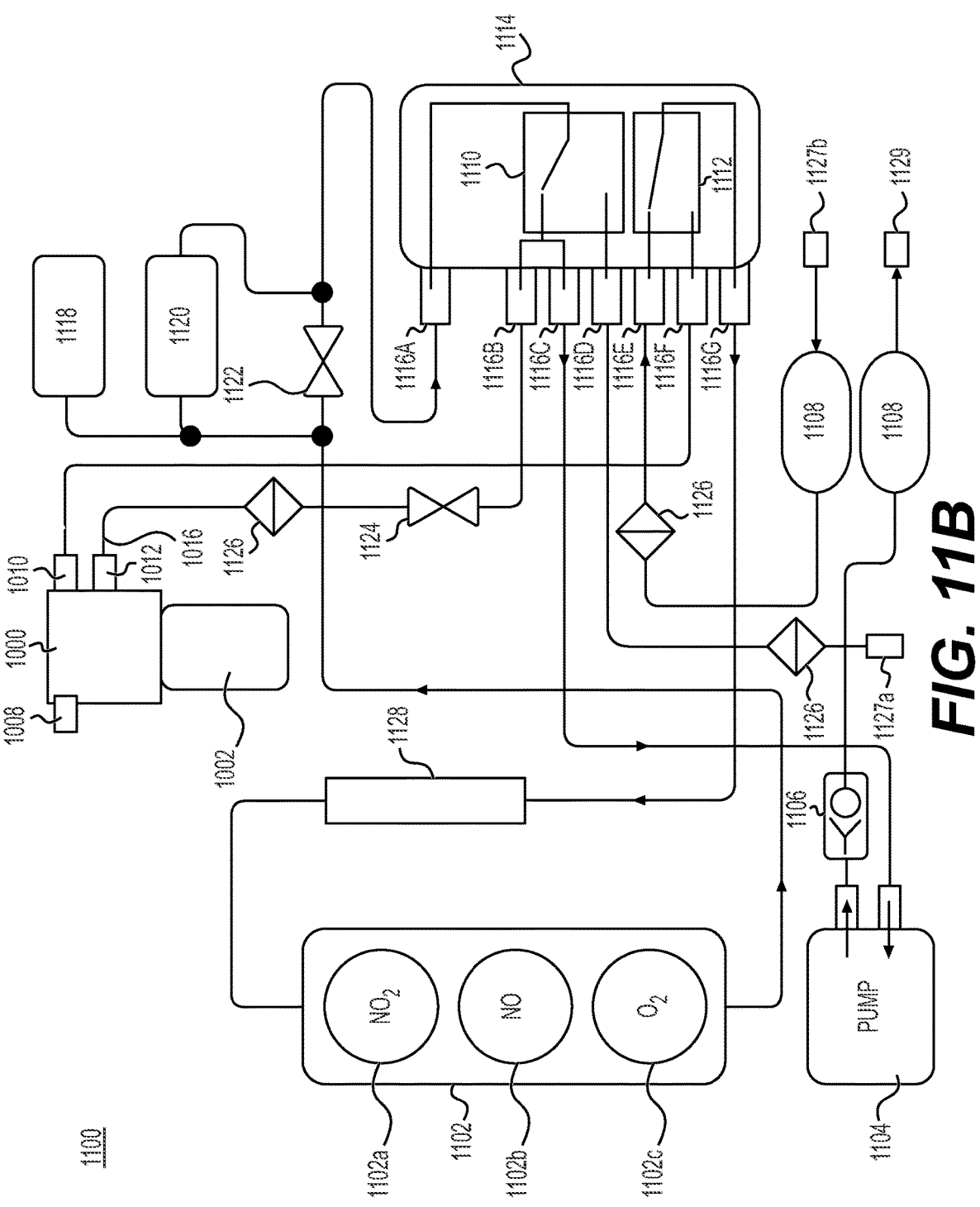

FIG. 11B a schematic representation of an initialization process of a gas monitoring device, according to some embodiments of the present disclosure.

Figure 11C:
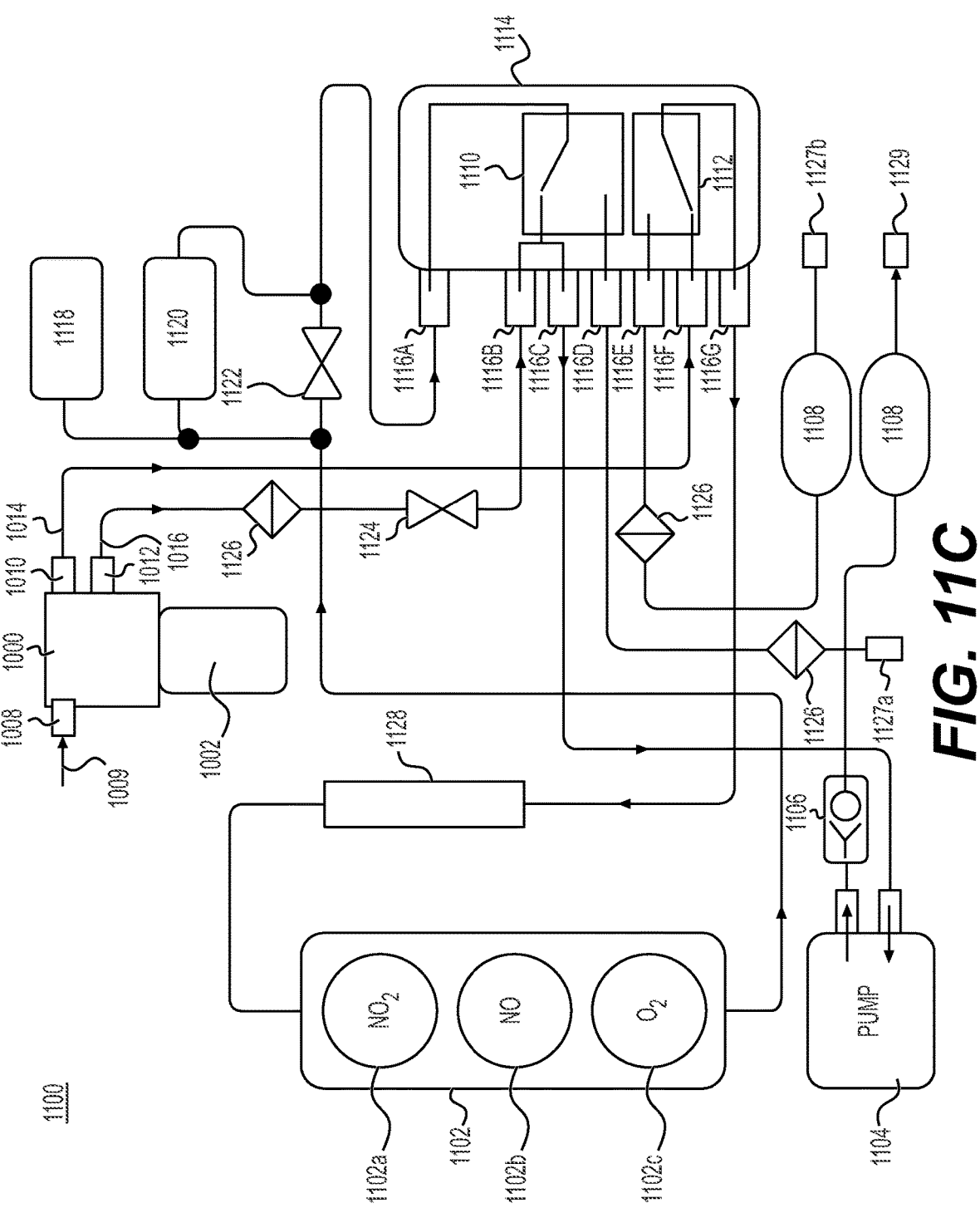

FIG. 11C a schematic representation of a cleaning process of a gas monitoring device, according to some embodiments of the present disclosure.

Figure 11D:
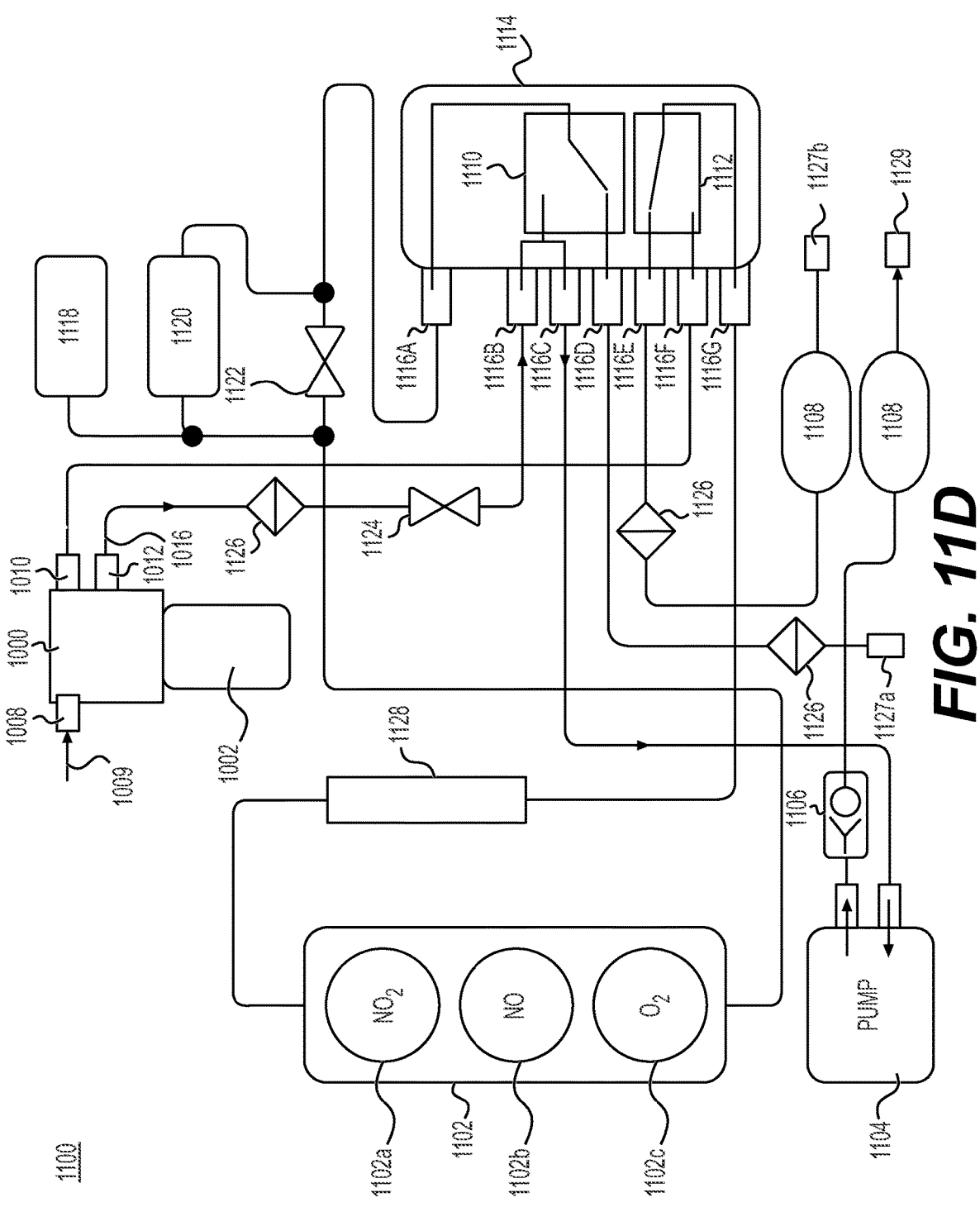

FIG. 11D a schematic representation of a calibration process of a gas monitoring device, according to some embodiments of the present disclosure.

FIG. 12 is a flow chart illustrating an NO generation method, according to some embodiments of the present disclosure.

DETAILED DESCRIPTION

Reference will now be made in detail to disclosed embodiments. Unless otherwise defined, technical or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

The present disclosure provides apparatuses, systems, and methods for generating NO from one or more electrochemical reactions. According to one aspect of the present disclosure, embodiments may output a product gas that includes NO. The NO in the product gas may be generated or delivered at a predetermined concentration and/or flow rate. For example, some embodiments may output a product gas having NO at clinically relevant concentrations and/or flow rates for inhaled NO therapies. The concentration and/or flow rate of NO in the product gas may be adjusted. The concentration of NO in the product gas may range from about 0 to about 20,000 ppm, for example.

The dimensionless unit "ppm" used in the present disclosure to describe gas concentrations refers to parts per million by volume and can be converted to other concentration units, such as parts per million by molar or milligrams per liter (mg/L). The dimensionless unit "%" or "% by volume" used in the present disclosure to describe gas concentrations refers to volume percentage and can be converted to other concentration units, such as weight percentage or molar concentration. As used herein, "about" in a numerical range indicates that the numerical range encompasses normal industry and subject matter variances or tolerances for manufacturing and/or operation. As used herein, the phrase "less than," "more than," "between one value and another value," or "form one value to another value" in a numerical range includes the endpoints and all values within or between the endpoints.

According to another aspect of the present disclosure, embodiments may allow for NO generation over a session that may include at least one operating period. The concentration and/or flow rate of NO in the product gas during an operating period may reach and/or remain at a steady state. As described herein, the concentration and/or flow rate of NO in the product gas at the steady state may vary from a certain value or a certain range by a steady state error. The steady state error may range from about 0 to about 10%, for example. The operating period may, for example, last for up to about 60 hours or more.

According to another aspect of the present disclosure, embodiments may allow for NO generation over a session that may include at least one ramp period. As described herein, a ramp period may refer to a transient period during which NO concentration of the product gas may increase or decrease from an initial concentration to a predetermined steady state concentration. The ramp period may be a ramp-up period or a ramp-down period. The ramp period may range from about 2 to about 10 minutes, for example. The ramp period may be predetermined or adjusted to allow for more rapid or immediate provision of a steady stream of NO, for example, as may be needed in an intensive care unit.

According to another aspect of the present disclosure, embodiments may allow for NO generation over a plurality of sessions. The plurality of sessions of NO generation may provide NO to treat the same patient over time or to treat different patients. One or more parameters for generating or delivering NO by some embodiments of the present disclosure may be predetermined and/or adjusted. For example, the number of sessions, the number of operating periods in a session, the start time and/or end time of an operating period, and/or the concentration and/or flow rate of NO in the product gas in an operating period of a session may be predetermined and/or adjusted.

According to another aspect of the present disclosure, to reduce exposure to health risks, embodiments may reduce or remove one or more toxic impurities, such as nitrogen dioxides, that may be present in the product gas.

Various apparatuses, systems, and methods for generating NO consistent with the present disclosure are described below.

Figure 1:
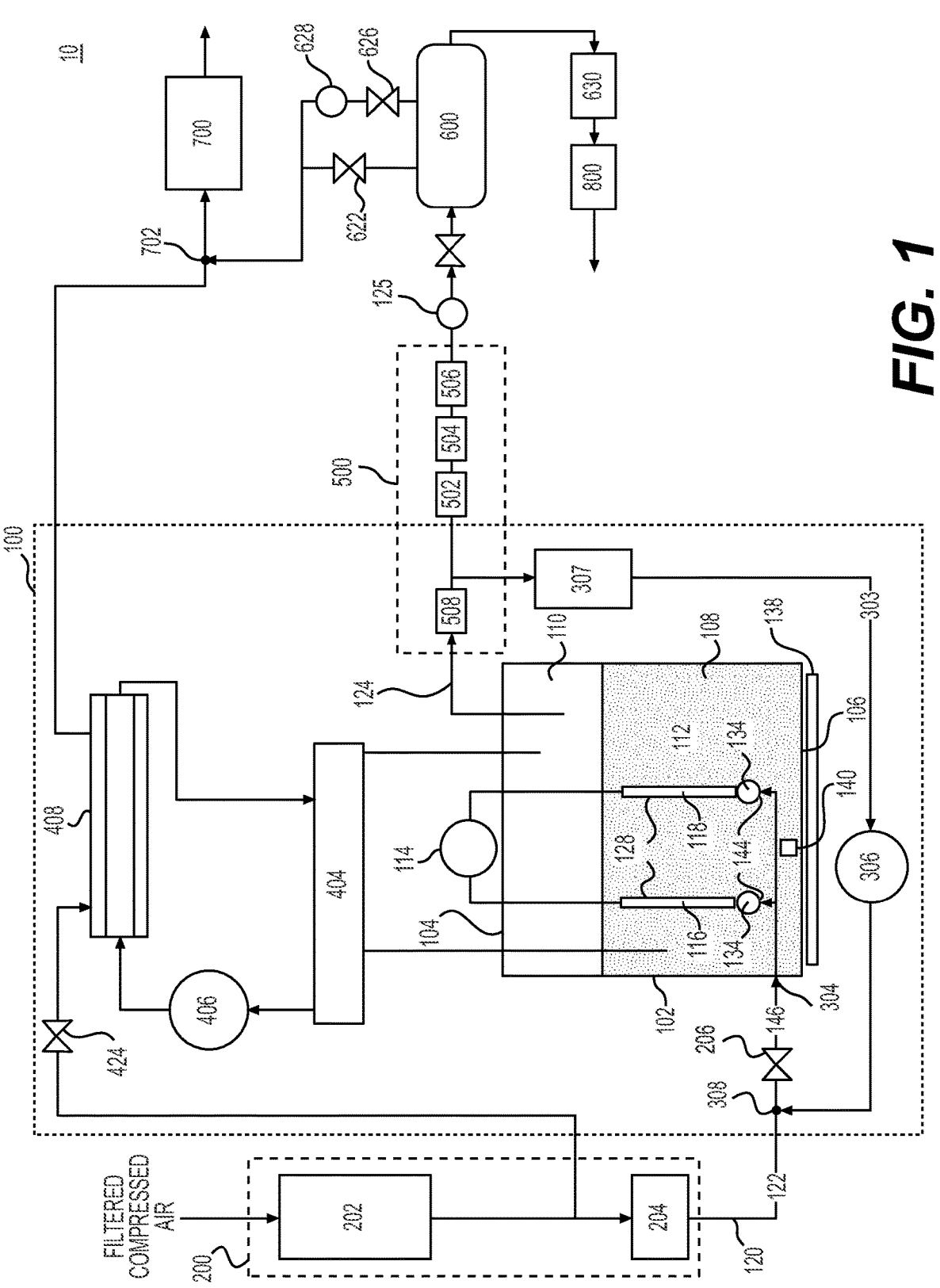
FIG. 1 is a schematic representation of an NO system, according to some embodiments of the present disclosure.

FIG. 1 is a schematic representation of an NO system 10, according to some embodiments of the present disclosure. As shown in FIG. 1, in some embodiments, system 10 includes an NO generation apparatus 100. NO generation apparatus 100 generates NO using one or more electrochemical reactions. In some embodiments, system 10 includes a carrier gas source 200 disposed upstream of and in fluid communication with NO generation apparatus 100. Carrier gas source 200 may generate or supply a carrier gas 122. Carrier gas 122 may be supplied to NO generation apparatus 100 to transport generated NO out of NO generation apparatus 100. For example, carrier gas 122 may sweep, purge, and/or entrain generated NO out of NO generation apparatus 100.

NO generation apparatus 100 may output generated NO in a product gas. The product gas may include one or more components. In some embodiments, the product gas includes the carrier gas. The product gas may flow from NO generation apparatus 100 to one or more downstream systems or devices. The one or more downstream systems or devices may transport, process, and/or store the product gas from NO generation apparatus 100. For example, the product gas may include one or more impurities, such as moisture, one or more toxic gases, and solid matter. In some embodiments, system 10 includes one or more filtration systems or devices to reduce or remove one or more impurities in the product gas. In some embodiments, system 10 includes a ventilation circuit to deliver NO to a patient with or without oxygen. Various embodiments of system 10 and methods for generating NO using system 10 are described below.

Electrochemical Generation of NO

Figure 2:
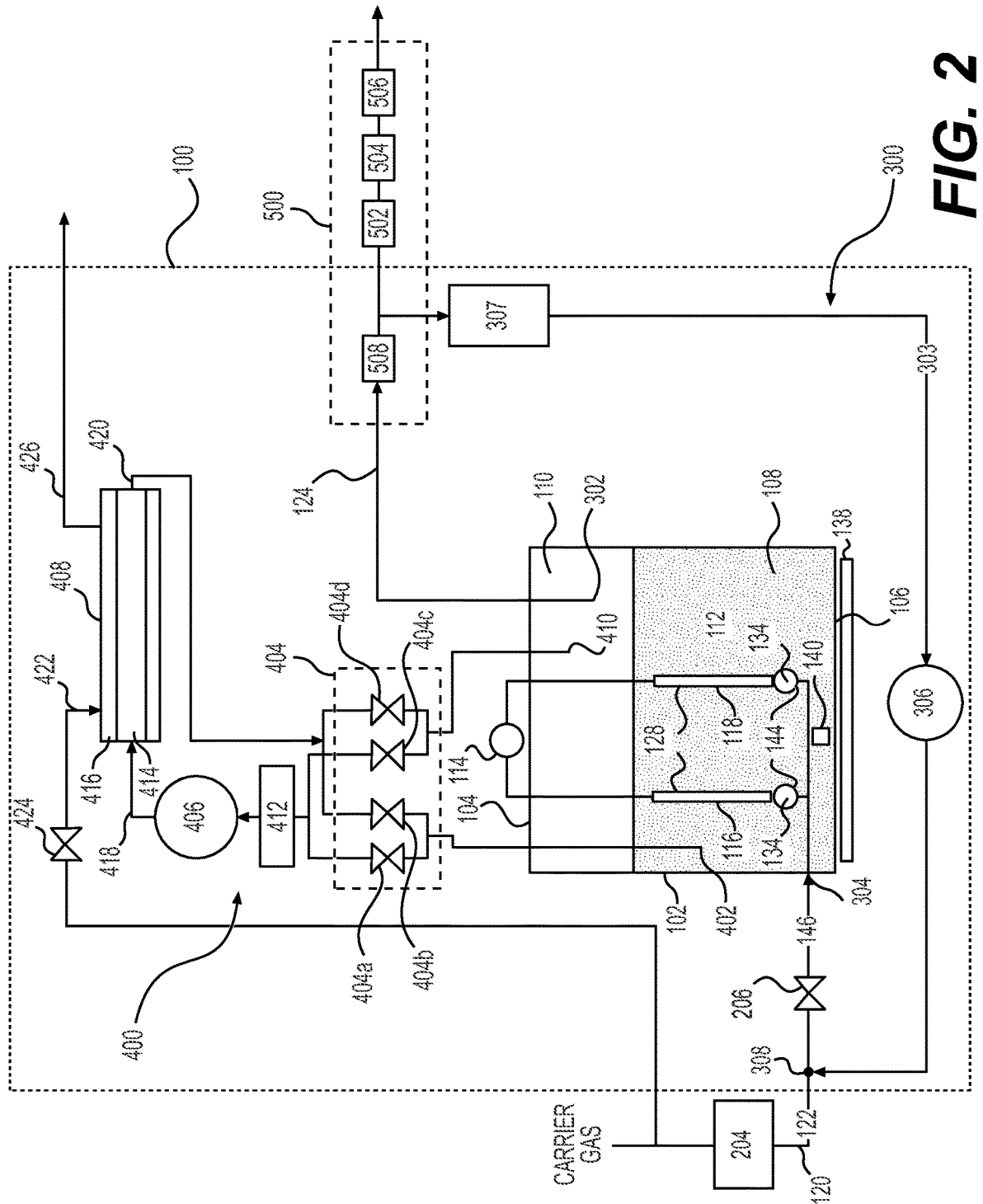
FIG. 2 is a schematic representation of an NO generation apparatus, according to some embodiments of the present disclosure.

FIG. 2 is a schematic representation of an NO generation apparatus 100, according to some embodiments of the present disclosure. NO generation apparatus 100 is configured to generate NO from one or more electrochemical reactions in a reaction medium 112. As shown in FIG. 2, in some embodiments, NO generation apparatus 100 includes a reaction chamber 102 and a plurality of electrodes. In some embodiments, reaction chamber 102 includes a liquid region 108 and a gas region 110. Liquid region 108 is configured to receive reaction medium 112. Gas region 110 is configured to receive gas generated in and/or transported from reaction medium 112.

In some embodiments, reaction chamber 102 has a first side 104 and a second side 106. First side 104 may be a top side of reaction chamber 102. Second side 106 may be a bottom side of reaction chamber 102. First side 104 and second side 106 may extend in parallel with each other. For example, first side 104 may have a surface that extends parallel to a surface of second side 106. Liquid region 108 may be disposed adjacent second side 106. Gas region 110 may be disposed adjacent first side 104.

As shown in FIG. 2, in some embodiments, NO generation apparatus 100 includes an inlet circuit 120 and an outlet circuit 124. Inlet circuit 120 is disposed downstream of and in fluid communication with carrier gas source 200. In some embodiments, inlet circuit 120 has at least one outlet 144, such as an opening, in liquid region 108. Inlet circuit 120 may receive carrier gas 122 and transport carrier gas 122 to liquid region 108. Outlet circuit 124 is disposed downstream of and in fluid communication with gas region 110 of reaction chamber 102. In some embodiments, outlet circuit 124 has at least one inlet, such as an opening, in gas region 110. NO generated may be transported out of in NO generation apparatus 100 from gas region 110 through outlet circuit 124, for example, by carrier gas 122.

In some embodiments, NO generation apparatus 100 may include one or more NO sensors (not shown) configured to detect a concentration of NO in the product gas. An NO sensor may be disposed at any suitable location. An NO sensor may be disposed in contact with the product gas in gas region 110, for example. In some embodiments, an NO sensor is disposed in or adjacent outlet circuit 124 of reaction chamber 102. For example, an NO sensor may be disposed at an opening of outlet circuit 124, such as at an inlet or an outlet of outlet circuit 124. For example, an NO sensor may be disposed within a conduit of outlet circuit 124. In some embodiments, an NO sensor may be disposed downstream of outlet circuit 124 or downstream of one or more filters or filtration devices downstream of outlet circuit 124. For example, as shown in FIGS. 1 and 2, an NO sensor 125 may be disposed downstream of a filter 506 of a filtration system 500 disposed downstream of outlet circuit 124.

In some embodiments, the plurality of electrodes of NO generation apparatus 100 include a first electrode 116 and a second electrode 118. First electrode 116 and second electrode 118 are disposed in reaction medium 112. In some embodiments, second electrode 118 is a counter electrode of first electrode 116. For example, first electrode 116 may be a cathode and second electrode 118 may be an anode, or vice versa. As described herein, although some embodiments in the present disclosure are described with respect to first electrode 116, similar embodiments with respect to second electrode 118 will be apparent to those skilled in the art. In some embodiments, the plurality of electrodes include a reference electrode. The reference electrode may be first electrode 116, second electrode 118, or a third electrode (not shown). The reference electrode may be disposed in or outside of reaction medium 112.

In some embodiments, as shown in FIG. 2, first electrode 116 and second electrode 118 are electrically connected to an energy source 114. In some embodiments, energy source 114 is configured to apply a voltage to first electrode 116 or to create an electric potential difference between first electrode 116 and second electrode 118. In some embodiments, energy source 114 is configured to apply a current to first electrode 116 or to create a current flow from second electrode 118 to first electrode 116, or vice versa. The voltage or current applied to an electrode may be predetermined and/or adjusted based on one or more conditions, such as a desired concentration and/or flow rate of NO in the product gas.

In some embodiments, a voltage applied to first electrode 116 may be measured as an electric potential difference between first electrode 116 and second electrode 118 or between second electrode 118 and first electrode 116. In some embodiments, a current applied to first electrode 116 may be measured as a current passing through first electrode 116. In some embodiments, a voltage applied to first electrode 116 may be measured as an electric potential difference between first electrode 116 and a reference electrode or between the reference electrode and first electrode 116.

In some embodiments, reaction medium 112 is a liquid. For example, reaction medium 112 may include an aqueous solution or an organic solution. In some embodiments, reaction medium 112 includes a source of nitrite ions. In some embodiments, NO generation apparatus 100 generates NO by electrochemically reducing nitrite ions in reaction medium 112 to NO adjacent and/or at a surface of an electrode, such as first electrode 116. In some embodiments, the electrochemical reduction of nitrite ions to NO is facilitated or enabled by one or more catalysts. In some embodiments, one or more catalysts are dissolved or dispersed in reaction medium 112. One or more catalysts may be adjacent and/or in contact with a surface of an electrode, such as first electrode 116, to separately or collectively function as electron transfer mediators between the surface of the electrode and the nitrite ions in reaction medium 112.

In some embodiments, a catalyst can be immobilized on a surface of an electrode, such as first electrode 116. In some embodiments, a catalyst includes one or more compounds selected from a group including cystine, cysteine, methionine, thiophene, and derivatives thereof. For example, the one or more catalysts may be covalently attached to, adsorbed to, or doped in or covalently attached to a material, such as a polymer, thin film, or hydrogel, deposited on the electrode. Some examples of the material that may be deposited on the electrode can be found in PCT/US2018/027081. As described herein, PCT/US2018/027081 is incorporated herein by reference for the relevant subject matter discussed in the present disclosure.

A catalyst may facilitate electrochemically reducing nitrite ions in reaction medium 112 to NO at and/or near a surface of an electrode, e.g., first electrode 116. In some embodiments, a catalyst includes a metal-containing compound, such as a metal-ligand complex. In some embodiments, a metal-containing compound may facilitate the electrochemical reduction of nitrite ions to NO in reaction medium 112 in accordance with the following reactions:

$$M(\text{first valence})(l) + e^- \rightarrow M(\text{second valence})(l) \qquad \text{Reaction 1}$$

$$M(\text{second valence})(l) + NO_2^- + 2H^+ \rightarrow \qquad \text{Reaction 2}$$

$$M(\text{first valence})(l) + NO + H_2O$$

where M(l) represents a metal-ligand complex, M represents at least one metal ion, l represents at least one surrounding ligand or complexing agent, and $NO_2^-$ represents nitrite ions. NO can be generated by reducing the at least one metal ion in the metal-ligand complex from a first valence to a second valence, the second valence being lower than the first valence. The reduced metal-ligand complex functions as an intermediate that reduces nitrite ions in reaction medium 112 to NO while being oxidized to the original metal-ligand complex.

The at least one metal ion may, for example, include one or more metal ions selected from copper, iron, titanium, chromium, manganese, cobalt, and nickel ions. The at least one surrounding ligand or complexing agent may include, for example, one or more selected from tris(2-pyridylmethyl)amine (TPA or TPMA), 1,4,7-triazacyclononane, 1,4, 7-trimethyl-1,4,7-triazacyclononane (Me₃TACN), tris(2-aminoethyl)amine, 3-((2-aminoethyl)amino)propanoic acid, and Bis(2-aminothypridine)propionic acid. Some other examples of a metal ion or a surrounding ligand or complexing agent can be found in PCT/US2018/027081.

In some embodiments, using a metal-ligand complex as a catalyst allows for using a cathodic voltage or a cathodic current to generate NO and/or modulate NO generation. In some embodiments, controlling the magnitude of the voltage or current applied to an electrode, such as first electrode 116, allows for controlling the ratio of the metal-ligand complex in reduced form to its oxidized form, for example, at and/or near the surface of the electrode. This may allow for controlling the amount and/or rate of NO generated under given concentrations of nitrite ions and metal-ligand complex in reaction medium 112.

In some embodiments, an electrode, such as first electrode 116, may have any suitable shape that includes one or more surfaces. For example, first electrode 116 may include a plate, a sheet, or a mesh. In some embodiments, when a cathodic voltage is applied to first electrode 116, or when a cathodic current is applied to first electrode 116, NO is electrochemically generated from one or more electrochemical reactions that occur at and/or near one or more surfaces of first electrode 116. Some or all NO generated from the electrochemical reactions at and/or near a surface of first electrode 116 in reaction medium 112 may be transported out of reaction medium 112 to gas region 110 of reaction chamber 102. For example, carrier gas 122 may be used to sweep, purge, and/or entrain some or all of the NO generated from reaction medium 112.

Energy source 114 may include one or more suitable power devices or circuits that allow for applying a voltage or current to an electrode, such as an electrical outlet, a power circuit, a DC power supply, an AC power supply, a generator, or an energy storage device. An energy storage device may include, for example, one or more batteries or fuel cells. In some embodiments, energy source 114 includes one or more electric circuits for controlling or adjusting the voltage or current applied to an electrode. In some embodiments, the one or more electric circuits may include a potentiostat to control or adjust the voltage applied to an electrode. In some embodiments, the one or more electric circuits may include a galvanostat to control or adjust the current passing through an electrode.

In some embodiments, the polarity of first electrode 116 and second electrode 118 can be switched. For example, the polarity of first electrode 116 and second electrode 118 may be switched by reversing the polarity of energy source 114, such as by inverting the polarity of the voltage or current from a DC power supply using a reversing switch circuit, for example, or by using an AC power supply. For example, energy source 114 is an AC power supply configured to apply periodic alternating current or alternating voltage to the electrodes.

Switching of the polarity of the electrodes may be automatically controlled by a control circuit according to a software program, for example. Additionally or alternatively, switching of the polarity of the electrodes may be manually controlled by a user, for example, by using a switch. The polarity of the electrodes may be switched during NO generation, between two operating periods, or between two sessions. NO in reaction medium 112 in contact with or adjacent an electrode may result in degradation of the electrode and may negatively impact NO generation efficiency. Switching the polarity of the electrodes may increase an effective surface area for NO generation and may increase the lifespan of the electrodes and/or of NO generation apparatus 100.

An electrode of NO generation apparatus 100, such first electrode 116, second electrode 118, or a reference electrode, may be made of one or more materials. One or more electrodes of NO generation apparatus 100 may be made of the same material or of different materials. In some embodiments, an electrode of NO generation apparatus 100 includes at least one electrically conductive material. The at least one electrically conductive material may be a metallic or non-metallic material. The at least one electrically conductive material may be selected, for example, from a group of electrically conductive materials including platinum, palladium, gold, copper, brass, silver, carbon, glassy carbon, boron doped diamond (BDD), graphite, stainless steel, titanium, iridium, ruthenium, and one or more alloys thereof, such as ruthenium-iridium alloy.

In some embodiments, an electrode of NO generation apparatus 100 includes at least one base material. The at least one base material may be a metallic or non-metallic material. The at least one base material may be selected, for example, from a group of materials, including silicon dioxide, conductive glass, tin-doped indium oxide, fluorine-doped indium oxide, conductive plastic, platinum, gold, copper, brass, silver, carbon, glassy carbon, boron doped diamond (BDD), graphite, stainless steel, titanium, iridium, ruthenium, and one or more alloys thereof, such as ruthenium-iridium alloy. In some embodiments, an electrode of NO generation apparatus 100 includes at least one electrically conductive material coated over at least one base material. The at least one electrically conductive material may be coated on the at least one base material using any suitable plating method, such as electroplating, physical vapor deposition (PVD), chemical vapor deposition (CVD), or plasma enhanced chemical vapor deposition (PECVD).

An electrode of NO generation apparatus 100, such first electrode 116, may have any shape, structure, and/or size. In some embodiments, first electrode 116 provides a surface at and/or adjacent to which NO is electrochemically generated. For example, the shape of first electrode 116 may be in the form of a plate, a sheet, a mesh, or a rod. A surface of first electrode 116 may have a surface area. The surface area may be positively related to a rate of generating NO at the surface. First electrode 116 may have a structure that allows for higher surface area, such as a porous structure.

Figure 3B:
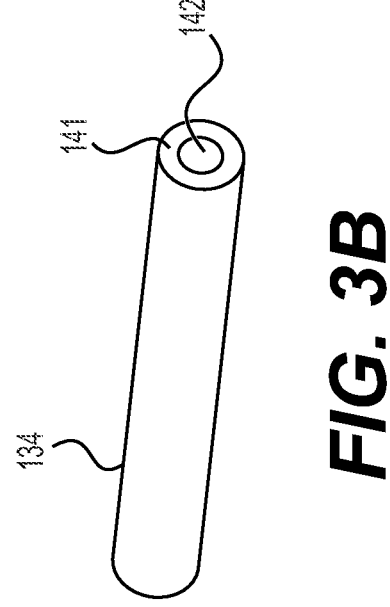
FIG. 3B is a perspective view of a sparger, according to some embodiments of the present disclosure.
Figure 3A:
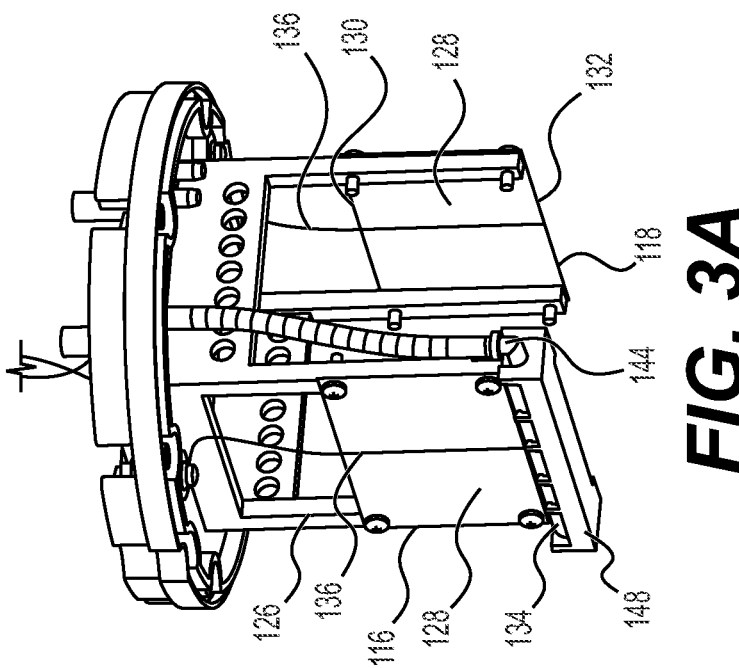
FIG. 3A is a schematic representation of a first electrode, a second electrode, and a sparger, according to some embodiments of the present disclosure.

FIG. 3A is a schematic representation of first electrode 116 and second electrode 118 of NO generation apparatus 100, according to some embodiments of the present disclosure. First electrode 116 and second electrode 118 may be placed in reaction chamber 102 using suitable means such that their surfaces are disposed in reaction medium 112. For example, as shown in FIG. 3A, a frame 126 may be used to place first electrode 116 and second electrode 118 in reaction chamber 102. Frame 126 may have a top side connected to first side 104 of reaction chamber 102. First electrode 116 and second electrode 118 may be attached to a frame 126 in any suitable way, such as by using screw, snap, wire, clip fasteners, or any other suitable fastening means.

In some embodiments, as shown in FIG. 3A, first electrode 116 and second electrode 118 include two rectangular plates having one or more surfaces 128. First electrode 116 and second electrode 118 may have the same size or similar sizes. In some embodiments, first electrode 116 and/or second electrode 118 have a length from about 3 cm to about 15 cm. In some embodiments, first electrode 116 and/or second electrode 118 have a width from about 2 cm to about 10 cm. First electrode 116 and second electrode 118 may be disposed apart by any suitable distance, such as from about 0.2 cm to about 10 cm apart. First electrode 116 and second electrode 118 may be disposed such that at least a portion of a surface 128 of first electrode 116 extends along, such as in parallel with, at least a portion of a surface 128 of second electrode 118.

In some embodiments, as shown in FIGS. 1-2, first electrode 116 and second electrode 118 are vertically positioned. For example, first electrode 116 and second electrode may be disposed perpendicular to second side 106 of reaction chamber 102. In some embodiments, each electrode includes a top edge 130 and a bottom edge 132. Top edge 130 may extend along, such as in parallel with, first side 104 of reaction chamber 102. Bottom edge 132 may extend along, such as in parallel with, the second side of reaction chamber 102.

Electrical wires may be used to electrically connect the electrodes to energy source 114. For example, as shown in FIG. 3A, an electric wire 136 is connected to energy source 114 (not shown) at a first end and is connected to an electrode, such as first electrode 116 or second electrode 118, at a second end. Electric wire 136 may be soldered or brazed to an electrode, such as first electrode 116 and second electrode 118. Electrical wire 136 may be made of one or more electrically conductive materials, such as copper, aluminum, steel, or silver, and may be treated for anti-corrosion purposes. In some embodiments, electric wire 136 is fastened to frame 126.

In some embodiments, the voltage applied to an electrode, such as first electrode 116, is a DC voltage. In some embodiments, the voltage applied to an electrode, such as first electrode 116, ranges from about 1.0 V to about 5.0 V, such as from about 1.0 V to about 2.0 V, from about 2.0 V to about 3.0 V, from about 3.0 V to about 4.0 V, from about 4.0 V to about 5.0 V, or a combination thereof.

In some embodiments, energy source 114 is configured to apply a stimulation voltage to an electrode, such as first electrode 116. In some embodiments, the stimulation voltage is from about 2 to about 8 times of a predetermined voltage, such as about 2 times, about 3 times, about 4 times, about 5 times, about 6 times, 7 about times, or 8 about times.

In some embodiments, the current applied to an electrode, such as first electrode 116, is a DC current. In some embodiments, the current applied to an electrode, such as first electrode 116, ranges from about 0 mA to about 600 mA, such as from about 0 mA to about 10 mA, from about 10 mA to about 50 mA, from about 50 mA to about 100 mA, from about 100 mA to about 200 mA, from about 200 mA to about 300 mA, from about 300 mA to about 400 mA, from about 400 mA to about 500 mA, from about 500 mA to about 600 mA, or a combination thereof.

In some embodiments, energy source 114 is configured to apply a stimulation current to the first electrode 116. In some embodiments, the stimulation current is about 2 to about 8 times of a predetermined current, e.g., about 2 times, about 3 times, about 4 times, about 5 times, about 6 times, about 7 times, or about 8 times.

A person skilled in the art may recognize that the stimulation voltage or stimulation current does not need to be at an integer times of a predetermined voltage or current. Any number within the range could be satisfactory for the purposes disclosed in this disclosure.

The polarity of the voltage or current can be switched manually or by software and/or hardware control, therefore swapping the polarity of first electrode 116 and second electrode 118. In some embodiments, the polarity of first electrode 116 and second electrode 118 are switched periodically. For example, the polarity of first electrode 116 and second electrode 118 may be switched about every 10 min to about every 10 hours, e.g., about, every 5 min to about every 10 min, about every 10 min to about every 30 min, about 30 min to about every 1 hour, about every 1 hour to about every 2 hours, about every 2 hours to about every 3 hours, about every 3 hours to about every 4 hours, about every 4 hours to about every 5 hours, about every 5 hours to about every 6 hours, about every 6 hours to about every 7 hours, about every 7 hours to about every 8 hours, about every 8 hours to about every 9 hours, about every 9 hours to about every 10 hours, or a combination thereof.

In some embodiments, reaction medium 112 includes at least one buffer or buffer component to regulate or to resist the change of pH of reaction medium 112. For example, the at least one buffer or buffer component may include one or more organic or inorganic buffer or buffer components selected from a group including sodium hydroxide (NaOH), 4-(2-hydroxyethyl)-1-piperazineethanesulfonic acid (HEPES), 3-(N-morpholino)propanesulfonic acid (MOPS), citric acid, sodium citrate, tris(hydroxymethyl)aminomethane (Tris), phosphate buffered saline (PBS), boric acid, borax, and boric acid-borax buffer. Some other examples of a buffer or buffer component that may be used in reaction medium 112 can be found in PCT/US2018/027081.

The at least one buffer or buffer component in reaction medium 112 may have any suitable concentration. For example, the concentration of the at least one buffer or buffer component in reaction medium 112 may range from about 0.01 mol/L to about 0.5 mol/L, from about 0.5 mol/L to about 1.0 mol/L, from about 1.0 mol/L to about 1.5 mol/L, from about 1.5 mol/L to about 2.0 mol/L, from about 2.0 mol/L to about 2.5 mol/L, from about 2.5 mol/L to about 3.0 mol/L, or a combination thereof.

The source of nitrite ions in reaction medium 112 may include one or more nitrite salts. The nitrite salt may be an organic nitrite salt or an inorganic nitrite salt. Examples of organic nitrite salts include organic ammonium nitrite salts, such as tetramethylammonium nitrite and tetraethylammonium nitrite. Examples of inorganic nitrite salts include metal nitrite salts, such as nitrite salts of Li, Na, K, Rb, Ca, Mg, Al, and Fe. Some other examples of the source of nitrite ions can be found in PCT/US2018/027081. The concentration of the one or more nitrite salts in reaction medium 112 may range from about 0.01 mol/L to about 0.5 mol/L, from about 0.5 mol/L to about 1.0 mol/L, from about 1.0 mol/L to about 1.5 mol/L, from about 1.5 mol/L to about 2.0 mol/L, from about 2.0 mol/L to about 2.5 mol/L, from about 2.5 mol/L to about 3.0 mol/L, from about 3.0 mol/L to about 3.5 mol/L, from about 3.5 mol/L to about 4.0 mol/L, from about 4.5 mol/L to about 5.0 mol/L, or a combination thereof.

When a catalyst is dissolved in reaction medium 112, the concentration of the catalyst in the reaction medium 112 may range from about 1 mmol/L to about 5 mmol/L, from about 1 mmol/L to about 10 mmol/L, from about 1 mmol/L to about 15 mmol/L, from about 5 mmol/L to about 10 mmol/L, from about 5 mmol/L to about 15 mmol/L, or from about 10 mmol/L to about 15 mmol/L.

Reaction medium 112 may include one or more other components. For example, reaction medium 112 may include one or more additives, such as ethylenediaminetetraacetic acid (EDTA) that may facilitate one or more of the electrochemical reactions for generating NO.

Embodiments of NO generation apparatus 100 may include one or more features described below to improve the performance of NO generation apparatus 100, such as to increase the reaction rate and/or Faraday efficiency of NO generation apparatus 100, to increase concentration of NO in the product gas, or to increase an amount or concentration of NO generated using a given amount of reaction medium 112. The Faraday efficiency of NO generation apparatus 100 may, for example, range from about 70% to about 80%, or higher.

Temperature Control of the Reaction Medium

In some embodiments, reaction medium 112 is maintained at or around a reaction temperature or within a temperature range. An electrochemical reaction in reaction chamber 102 may have a highest, desired, or optimized reaction rate and/or Faraday efficiency at or around the reaction temperature or within the temperature range. The reaction temperature or temperature range may be determined based on one or more conditions, such as the buffer and/or catalyst components and concentrations in reaction medium 112. In some embodiments, the reaction temperate or temperature range may range from about 5° C. to about 10° C., from about 10° C. to about 15° C., from about 15° C. to about 20° C., from about 20° C. to about 25° C., from about 25° C. to about 30° C., from about 20° C. to about 30° C., from about 30° C. to about 35° C., from about 35° C. to about 40° C., from about 40° C. to about 45° C., or a combination thereof.

In some embodiments, NO generation apparatus 100 includes a temperature maintaining device 138 to control the temperature of reaction medium 112. For example, as shown in FIGS. 1-2, temperature maintaining device 138 may be disposed adjacent reaction chamber 102, such as disposed under, next to, or around reaction chamber 102. In some embodiments, temperature maintaining device 138 includes one or more temperature control apparatus, such as a temperature control water bath, a temperature control oil bath, an air agitating device (e.g., a fan), a thermal radiator, a thermoelectric heating and/or cooling device (e.g., a p-n junction device).

In some embodiments, NO generation apparatus 100 includes a temperature sensor 140 disposed in reaction medium 112 and in communication with temperature maintaining device 138. Temperature maintaining device 138 may monitor the temperature of reaction medium 112 based on signals from temperature sensor 140. Temperature maintaining device 138 may heat or cool reaction medium 112 in response to the signals. In some embodiments, a voltage or current applied to an electrode, such as first electrode 116, may be adjusted by energy source 114 based on signals from temperature sensor 140. For example, a control circuit of energy source 114 may be in communication with temperature sensor 140 and may adjust the amplitude and/or polarity of the voltage or current applied to first electrode 116.

Transporting NO from Reaction Medium

Some or all of the NO generated in reaction medium 112 may be transported from reaction medium 112. For example, NO generated in reaction medium 112 may be transported, such as by being swept, purged, and/or entrained from reaction medium 112 to gas region 110 using carrier gas 122

In some embodiments, as shown in FIG. 2, carrier gas 122 is used to sweep surface 128 of an electrode, such as first electrode 116. The sweeping of the surface of the electrode may increase the Faraday efficiency and/or reaction rate the electrochemical reactions at and/or adjacent the surface of the electrode and/or may increase the NO concentration of the product gas. For example, in some instances, one or more metal ions of a catalyst in reaction medium 112, such as M (first valence) generated from the Electrochemical Reaction 2, may precipitate into an insoluble form. For example, a metal ion of a catalyst may be $Cu^{2+}$. In some instances, $Cu^{2+}$ may be precipitated from the following reaction:

$$Cu^{2+}+2OH^-\rightarrow Cu(OH)_2\downarrow\rightarrow CuO+H_2O$$

The precipitation of the metal ions of a catalyst in reaction medium 112 may reduce the concentration of the catalyst in reaction medium 112 and may reduce the rate of the electrochemical reactions for generating NO. The precipitation of the metal ions may cause the insoluble form of the metal ions, such as $Cu(OH)_2$, to be deposited on a surface of an electrode. This may reduce the surface area for generating NO and may also reduce the lifespan of the electrode. Sweeping the surface of an electrode may increase movement of substances, such as the metal ions, at and/or adjacent the surface of the electrode. This may reduce or inhibit deposition of the metal ions on the surface and thus may increase NO generation rate and/or NO concentration of the product gas.

Carrier gas 122 may be introduced into reaction medium 112 through one or more flow control devices. For example, as shown in FIG. 2, carrier gas source 200 may include a flow control device 204 that may measure and control the mass or volumetric flow rate of a flow of carrier gas 122 introduced into reaction medium 112. A value 206 may be disposed downstream of flow control device 204 to protect flow control device 204. For example, valve 206 may be a one-way valve configured to prevent reaction medium 112 from flowing back to flow control device 204 from inlet circuit 120. Embodiments for supplying carrier gas 122 from carrier gas source 200 to NO generation apparatus 100 is described further below.

In some embodiments, carrier gas 122 is introduced into reaction medium 112 in the form of bubbles configured to propagate along a bubble path. The bubble path may extend along a surface of an electrode, such as surface 128 of first electrode 116, to sweep the surface. The carrier gas bubbles may entrain, sweep, and/or purge NO generated adjacent and/or at surface 128 of first electrode 116 when rising to the surface of reaction medium 112. The carrier gas bubbles may mix or disturb reaction medium 112 adjacent surface 128 of first electrode 116, and may increase movement of substances, such as the metal ions, adjacent the surface. The carrier gas bubbles may purge NO dissolved in reaction medium 112 from reaction medium 112 to gas region 110.

In some embodiments, NO generation apparatus 100 includes one or more spargers to generate bubbles form carrier gas 122. As used herein, a sparger may include a device or system configured to emanate gas bubbles into a liquid. In some instances, a sparger may be referred to as a bubbler. The one or more spargers may be disposed at any suitable place in reaction medium 112 to emanate bubbles of carrier gas 122 to transport, such as sweep, purge, and/or entrain, NO out of reaction medium 112. For example, one or more spargers may be disposed above or adjacent second side 106 of reaction chamber 102.

In some embodiments, as shown in FIG. 2, NO generation apparatus 100 includes a first sparger 134 disposed in reaction medium 112 adjacent first electrode 116. In some embodiments, as shown in FIG. 2, NO generation apparatus 100 includes a second sparger 134 disposed adjacent second electrode 118. In some embodiments, sparger 134 is configured to receive carrier gas 122 and emanates bubbles of the carrier gas to sweep one or more surfaces 128 of first electrode 116 or second electrode 118. FIG. 3B is a perspective view of a sparger 134, according to some embodiments of the present disclosure. As shown in FIG. 3B, sparger 134 may have an elongated shape, such as an elongated cylindrical shape.

In some embodiments, as shown in FIG. 3A, sparger 134 may be disposed along first electrode 116 or second electrode 118 such that bubbles emanated from sparger 134 may rise and propagate along one or more surfaces 128 of first electrode 116 or second electrode 118. For example, as shown in FIGS. 2 and 3A, sparger 134 may be disposed between bottom edge 132 of first electrode 116 or second electrode 118 and second side 106 of reaction chamber 102. Bubbles emanated from sparger 134 may propagate along a bubble path that extends from bottom edge 132, across surface 128, to top edge 130 of first electrode 116 or second electrode 118. In some embodiments, sparger 134 may extend along the length of bottom edge 132 such that bubbles may sweep an entire surface 128 of first electrode 116.

In some embodiments, the distance between sparger 134 and first electrode 116 or second electrode 118 may be selected to increase the coverage and/or efficiency of the sweeping of one or more surfaces of the electrode. Sparger 134 may be disposed from an electrode at a distance that is, for example, less than about 1 cm, less than about 5 mm, less than about 2 mm, less than about 1 mm, or less than about 0.5 mm.

Sparger 134 may have any suitable structure to receive a gas and emanate bubbles of the gas. In some embodiments, sparger 134 includes a porous structure 141 that provides a plurality of pores for emanating bubbles. For example, as shown in FIG. 3B, sparger 134 may include an inner cavity 142 surrounded by a porous structure 141. A gas may flow through inner cavity 142 and bubbles through pores in porous structure 141. Inner cavity 142 may have a tubular shape extending from a first opening to a second opening. Inner cavity 142 may or may not extend along a center line of sparger 134. Inner cavity 142 may have a diameter selected based on one or more conditions, such as a flow rate of a received gas and a desired density and/size of bubbles. For example, inner cavity 142 may have a diameter ranging from about 1 mm to about 9 mm, such as from about 1 mm to about 2 mm, from about 2 mm to about 3 mm, from about 3 mm to about 4 mm, from about 4 mm to about 5 mm, from about 5 mm to about 6 mm, from about 6 mm to about 7 mm, from about 7 mm to about 8 mm, from about 8 mm to about 9 mm, or a combination thereof.

In some embodiments, as shown in FIGS. 2 and 3A, outlet 144 of inlet circuit 120 is fluidly connected to sparger 134, such as inner cavity 142 of sparger 134. Carrier gas 122 may flow from carrier gas source 200 through inlet circuit 120 to sparger 134 via outlet 144. In some embodiments, sparger 134 is attached to a sparger seat 148. In some embodiments, sparger seat 148 is attached to frame 126. Sparger seat 148 may allow sparger 134 to be disposed at a desired position.

In some embodiments, sparger seat 148 may include one or more structures for directing the flow of the bubbles. For example, sparger seat 148 may include a casing with one or more openings configured to direct bubbles emanated from sparger 134 to one or more surfaces 128 of an electrode. For example, as shown in FIG. 3A, sparger seat 148 may include an opening at a top and/or an upper portion of sparger 134 such that bubbles may emanate from the upper portion of sparger 134 and propagate along surface 128 of first electrode 116. Sparger seat 148 may include one or more blocking or sealing means to prevent one or more portions of sparger 134 from emanating gas or bubbles. For example, sparger seat 148 may have a portion configured to block gas from directly flowing out of inner cavity 142 without passing through porous structure 141. For example, sparger seat 148 may have a portion blocking or sealing a first end of inner cavity 142 opposite to a second end connected to outlet 144.

In some embodiments, sparger 134 includes at least one porous material providing porous structure 141. The density and/or sizes of the bubbles may depend on one or more conditions, such as gas pressure, the flow rate of the gas, and the density and/or sizes of the pores of the at least one porous material. Under a given flow rate of gas, smaller pores may allow for generating smaller bubbles by sparger 134 with higher density. The at least one porous material may include a metallic material, such as stainless steel. The at least one porous material may include a non-metallic material. The non-metallic material may be a polymeric material, such as polyethylene (PE), polycarbonate (PC), polyvinylidene fluoride (PVDF), ceramic, quartz, or silicon carbide.

The sizes of the pores of the at least one porous material of sparger 134 may be selected based on a desired density, sizes, and/or flow rates of the bubbles. For example, the sizes of the pores may range from about 0.1 μm to about 0.5 μm, from about 0.1 μm to about 0.2 μm, from about 0.2 μm to about 0.5 μm, from about 0.5 μm to about 1 μm, from about 1.0 μm to about 10 μm, from about 10 μm to about 20 μm, from about 20 μm to about 50 μm, from about 50 μm to about 100 μm, from about 100 μm to about 150 μm, from about 150 μm to about 200 μm, from about 200 μm to about 300 μm, from about 300 μm to about 400 μm, from about 400 μm to about 500 μm, from about 500 μm to about 600 μm, from about 600 μm to about 700 μm, from about 700 μm to about 800 μm, from about 800 μm to about 900 μm, from about 900 μm to about 1 mm, or a combination thereof.

A porous material of sparger 134 may have a thickness through which a gas flow passes through to create bubbles. The thickness of the porous material may be measured from an inner surface to an outer surface of the porous material. Increasing the thickness of the porous material may increase gas flow resistance and reduce bubbling efficiency. Decreasing the thickness of the porous material may reduce the density and/or velocity of the bubbles. The thickness of the porous material may be selected to obtain any suitable density and/or size of bubbles for sweeping the electrode surfaces. For example, a thickness of the porous material may range from about 0.5 mm to about 1 mm, from about 1 mm to about 2 mm, from about 2 mm to about 3 mm, from about 3 mm to about 4 mm, from about 4 mm to about 5 mm, from about 5 mm to about 6 mm, from about 6 mm to about 7 mm, from about 7 mm to about 8 mm, from about 8 mm to about 9 mm, from about 9 mm to about 10 mm, or a combination thereof.

Carrier Gas Generation

In some embodiments, carrier gas 122 is generated or supplied by carrier gas source 200. Carrier gas 122 may include any suitable gas, such as air, nitrogen, helium, argon, and oxygen. In some embodiments, carrier gas 122 includes nitrogen. In some embodiments, the concentration of nitrogen in carrier gas 122 is about or higher than 99.0% by volume. For example, the concentration of nitrogen in carrier gas 122 may be about or higher than 99.10%, 99.20%, 99.30%, 99.40%, 99.50%, 99.60%, 99.70%, 99.80%, 99.90%, 99.95%, 99.98%, or 99.99% by volume. Carrier gas 122 may contain oxygen. For example, the concentration of oxygen in carrier gas 122 may be less than about 1%, 0.5%, or 0.1%.

In some embodiments, as shown in FIG. 1, carrier gas source 200 includes a nitrogen generating apparatus 202 configured to generate carrier gas 122 from compressed air. In some embodiments, the compressed air is supplied to carrier gas source 200 from an air compressor system or repository. In some embodiments, the compressed air is filtered before being supplied to carrier gas source 200. For example, carrier gas source 200 may include a filtration apparatus disposed upstream of and configured to be in fluid communication with nitrogen generating apparatus 202. The filtration apparatus may include one or more filters, such as a dust filter and a moisture filter. In some embodiments, carrier gas source 200 includes a pressure sensor and a pressure control, such as a pressure regulator or a pressure control valve. The pressure control may regulate the pressure and/or flow rate of the compressed air entering nitrogen generating apparatus 202 based on a response or signal from the pressure sensor.

Nitrogen generating apparatus 202 may include one or more suitable devices for generating nitrogen from compressed air. In some embodiments, nitrogen generating apparatus 202 includes at least one carbon molecular sieve (CMS). The carbon molecular sieve may have a pore size distribution allowing for separating nitrogen from air. In some embodiments, nitrogen generating apparatus 202 includes at least one nitrogen separation membrane. The nitrogen separation membrane may separate nitrogen from air based on permeation rates of nitrogen and oxygen across the membrane wall. The nitrogen separation membrane may have any suitable configuration. In some embodiments, the nitrogen separation membrane includes at least one bundle of selectively permeable hollow fibers.

The nitrogen separation membrane may include one or more materials selected from a group including poly(4-methyl-1-pentene), brominated polycarbonate, polypropylene, polyimide, and polydimethylsiloxane. In some embodiments, the nitrogen separation membrane has a plurality of pores with an average pore size ranging from about 0.005 μm to about 0.007 μm, from about 0.007 μm to about 0.01 μm, from about 0.01 μm to about 0.013 μm, from about 0.013 μm to about 0.015 μm, from about 0.015 μm to about 0.017 μm, from about 0.017 μm to about 0.019 μm, from about 0.019 μm to about 0.02 μm, or a combination thereof.

As described herein, the description of nitrogen generating apparatus 202 is generally applicable and would be readily apparent to a skilled artisan to an apparatus for generating other carrier gases, such as helium, argon, and oxygen.

In some embodiments, nitrogen generating apparatus 202 is disposed upstream of and in fluid communication with inlet circuit 120. In some embodiments, as shown in FIG. 1, carrier gas source 200 further includes flow control device 204 disposed downstream of nitrogen generation apparatus 202 and upstream of inlet circuit 120. Flow control device 204 may be configured to control the flow rate of carrier gas 122 entering NO generation apparatus 100. Increasing the flow rate of carrier gas 122 may increase NO generation rate and/or concentration of NO in the product gas. For example, increasing the flow rate of carrier gas 122 may increase the sweeping of a surface of first electrode 116, and may increase the rate of transporting generated NO from reaction medium 112. In some embodiments, the flow rate of the product gas of NO generation apparatus 100 output from outlet circuit 124 is proportional to the flow rate of carrier gas 122.

Recirculation of Product Gas Relative to the Reaction Chamber

In some embodiments, as shown in FIG. 2, NO generation apparatus 100 includes a gas circulation circuit 300. In some embodiments, gas circulation circuit 300 includes a circulation inlet 302 and a circulation outlet 304. In some embodiments, circulation inlet 302 is in fluid communication with gas region 110 of reaction chamber 102. For example, circulation inlet 302 may include an opening disposed inside or on a wall of gas region 110. In some embodiments, circulation outlet 304 is in fluid communication with liquid region 108 of reaction chamber 102. For example, circulation outlet 304 may be in fluid communication with inlet circuit 120. Circulation outlet 304 may include an opening disposed inside or on a wall of liquid region 108, for example.

In some embodiments, the product gas in gas region 110 is recirculated relative to the reaction chamber 102 from circulation inlet 302 to circulation outlet 304. For example, a recirculated product gas 303 may flow from circulation inlet 302 to circulation outlet 304. In some embodiments, gas circulation circuit 300 includes a gas pump 306 configured to generate a flow of recirculated product gas 303. Gas pump 306 may be disposed downstream of circulation inlet 302 and upstream of circulation outlet 304.

In some embodiments, as shown in FIG. 2, gas circulation circuit 300 is in fluid communication with outlet circuit 124 of NO generation apparatus 100. For example, circulation inlet 302 of gas circulation circuit 300 may be in fluid communication with outlet circuit 124. Gas circulation circuit 300 and outlet circuit 124 may have a common inlet, such as circulation inlet 302. Gas circulation circuit 300 and outlet circuit 124 may have a common fluid path. In some embodiments, gas circulation circuit 300 includes a first filtration device 508 disposed downstream of circulation inlet 302. The common fluid path may extend from the common inlet to first filtration device 508.

In some embodiments, first filtration device 508 is disposed upstream of gas pump 306. Filtration device 508 may reduce or remove liquid and/or solid matter from recirculated product gas 303. In some embodiments, gas circulation circuit 300 includes a second filtration device 307. Second filtration device 307 may include a capsule filter or a membrane filter. Second filtration device 307 may remove one or more impurities in recirculated product gas 303, such as liquid and solid matter, and thus protect gas pump 306.

Recirculated product gas 303 may be introduced to a surface of an electrode to sweep the surface of the electrode. In some embodiments, circulation outlet 304 is in fluid communication with sparger 134. For example, circulation outlet 304 may be fluidly connected with inner cavity 142 of sparger 134. Gas pump 306 may be disposed downstream of circulation inlet 302 and upstream of sparger 134 and recirculated product gas 303 may flow from circulation inlet 302 to inner cavity 142 of sparger 134.

In some embodiments, as shown in FIG. 2, recirculated product gas 303 is combined with carrier gas 122 into a gas stream 146. For example, gas circulation circuit 300 may include a three-way connector 308. Three-way connector 308 may be fluidly connected with circulation outlet 304 and configured to receive recirculated product gas 303. Three-way connector 308 may be fluidly connected with carrier gas source 200 and/or inlet circuit 120 and configured to receive carrier gas 122. Three-way connector 308 may combine the received recirculated product gas 303 and carrier gas 122 into gas stream 146. Three-way connector 308 may include any suitable structure, such as a three-way fitting or a three-way valve. Gas stream 146 may be supplied to sparger 134 to generate bubbles for sweeping a surface of an electrode.

In some embodiments, gas circulation circuit 300 may include valve 206. Valve 206 may be disposed upstream of circulation outlet 304. Valve 206 may be disposed downstream of gas pump 306 and may be disposed downstream of three-way connector 308. Valve 206 may prevent backflow of gas stream 146 and/or back flow of reaction medium 112 from reaction chamber 102 to gas pump 306. Gas stream 146 may flow through valve 206 towards circulation outlet 304 and outlet 144 and be supplied to one or more spargers 134. One or more spargers 134 may also emanate bubbles from gas stream 146 to transport, such as sweep, purge, and/or entrain, NO generated in reaction medium 112 to gas region 110. For example, in some embodiments, sparger 134 emanates bubbles from gas stream 146 to sweep a surface of an electrode, such as first electrode 116.

The product gas in gas region 110 may include carrier gas 122 and generated NO. In some embodiments, recirculating the product gas in gas region 110 allows for recirculating carrier gas 122 in the product gas to a surface of an electrode. Recirculating the carrier gas may reduce the amount of carrier gas needed to support NO generation, for example, for sweeping first electrode 116 and/or transporting generated NO. Recirculating the product gas may allow NO to accumulate in the product gas in gas region 110 of reaction chamber 102, allowing for a higher concentration of NO in the product gas in gas region 110. This may allow for a higher and/or more stable concentration of NO in the product gas transported from gas region 110 of NO generation apparatus 100.

Figure 4A:
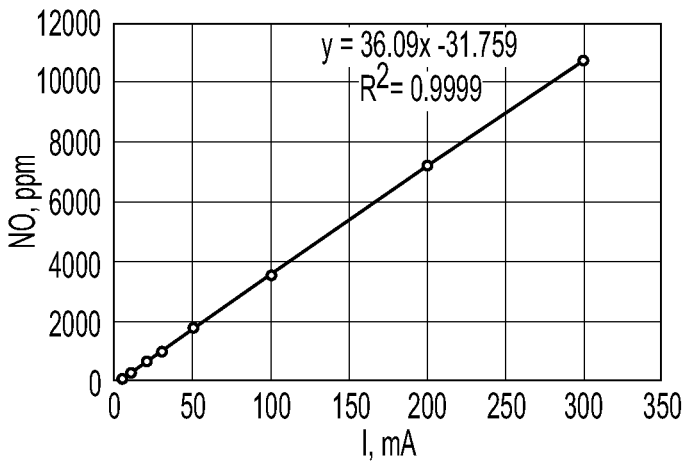
FIG. 4A is a graphical representation of concentrations of NO in a product gas generated by an NO generation apparatus versus current applied to an electrode, according to some embodiments of the present disclosure.

FIG. 4A is a graphical representation of concentrations of NO in the product gas versus a current applied to first electrode 116, according to some embodiments of the present disclosure. In this example, NO generation apparatus 100 can include a reaction chamber 102 having a gas region and a liquid region, a reaction medium 112 contained in the liquid region, a first electrode 116 and a second electrode 118 disposed in the reaction medium 112, a sparger 134 for sweeping a surface of the first electrode 116, a gas circulation circuit 300 for recirculating a product gas, and a sparger 134 for sweeping a first electrode 116. The electrodes can each be made of stainless steel and can each include a plate having a surface area of about 5 cm by about 6 cm. The reaction medium 112 can include about 1.0 mol/L NaNO$_2$, about 7 mmol/L CuSO$_4$, about 7 mmol/L Me$_3$TACN, and about 0.5 mol/L HEPES buffer. A suitable base solution, such as a NaOH solution can be used to titrate the HEPES buffer such that the reaction medium 112 can have a pH anywhere from about 6 to about 8, such as a pH of about 7.2. The sparger 134 can have a cylindrical shape having a length of about 7 cm, an inner diameter of about 5 mm, and an outer diameter of about 10 mm, and can have an average pore size of about 20 μm. A carrier gas 122 containing N$_2$ at a concentration of about 99.7% by volume can be introduced to the sparger 134 at a flow rate of about 300 mL/min. The gas circulation circuit 300 can recirculate the product gas at a flow rate of about 3 L/min. As shown in FIG. 4A, the concentration of NO in the product gas can increase by increasing the current applied to the first electrode 116 from about 0 mA to about 300 mA. In this example, fitting the data to a linear regression model indicates that the concentration of NO in the product gas can increase by about 36.1 ppm for every 1 mA of applied current and NO generation apparatus 100 can have a Faraday efficiency of 70.7%. Reducing the sweeping of first electrode 116 may reduce the increase of NO concentration per unit of applied current and may reduce the Faraday efficiency.

Figure 4B:
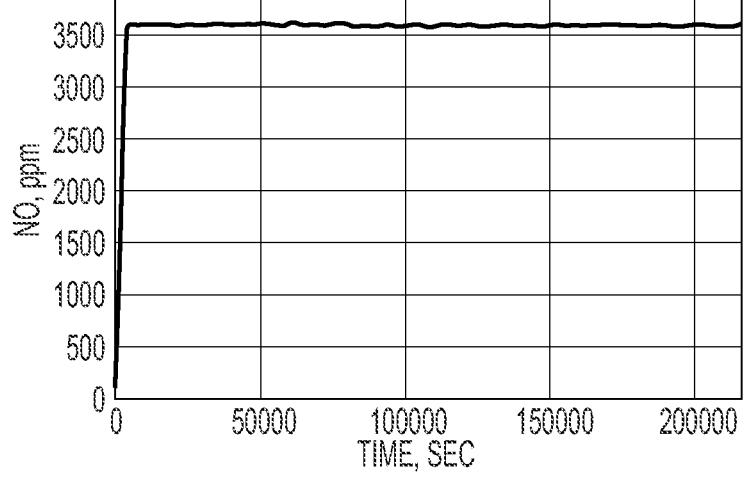
FIG. 4B is a graphical representation of concentrations of NO in a product gas generated by an NO generation apparatus over time, according to some embodiments of the present disclosure.

FIG. 4B is a graphical representation of concentrations of NO in a product gas generated by an NO generation apparatus 100 over time, according to some embodiments of the present disclosure. In this example, an NO generation apparatus 100 can have the same reaction conditions as described in the example above with reference to FIG. 4A except that a current of 100 mA can be applied to first electrode 116 for about 60 hours after an initial application of a current of about 300 mA over a ramp period of about 2 minutes. The concentration of NO in the product gas of the NO generation apparatus 100 increased to about 3600 ppm after the ramp period and remained at a steady state concentration at or around 3600 ppm for about 60 hours. Generating this amount of NO would typically require about 4 to 5 gas tanks storing about 8 L of compressed NO having an NO concentration of about 800 ppm at a pressure of about 13.8 MPa. The use of sparger 134 for sweeping the surface of first electrode 116 and the recirculation of the product gas by gas circulation circuit 300 allowed for generating NO at a steady concentration over a long period of time. The amount of NO that can be generated by NO generation apparatus 100, such as having a product gas having an NO concentration of about 3600 ppm for about 60 hours.

Separation of NO from the Reaction Medium

Reaction medium 112 of NO generation apparatus 100 may be reused to generate NO before being disposed, replaced, or replenished. For example, reaction medium 112 of NO generation apparatus 100 may be used to generate NO over a plurality of operating periods in a session or over a plurality of sessions. Some generated NO may dissolve in reaction medium 112 after an operating period or a session. NO dissolved in reaction medium 112 may reduce the concentration and/or amount of NO that can be generated from reusing reaction medium 112, and may increase wait time between sessions or operating periods.

For example, NO dissolved in reaction medium 112 may interact with a metal-ligand complex catalyst, such as Cu(II)-1,4,7-trimethyl-1,4,7-triazacyclononane (Cu (Me$_3$TACN)). NO dissolved in reaction medium 112 may bind to the central copper ion of Cu(Me$_3$TACN), for example, during a wait time between two sessions. This may reduce the concentration of the metal-ligand complex in reaction medium 112 for catalyzing the electrochemical reactions for generating NO in the next session, and may reduce the reaction rate and/or the concentration of NO in the product gas of the next session. In some instances, the concentration of NO in the product gas of a session may be lower than that of a previous session, such as by about 10% to about 30%.

In some embodiments, one or more spargers 134 disposed in reaction medium 112 may generate gas bubbles to purge dissolved NO out of reaction medium 112 to gas region 110 and thus reduce NO dissolved in reaction medium 112. In some embodiments, sweeping a surface of an electrode may reduce NO dissolved in reaction medium 112. For example, sparger 134 may generate gas bubbles to propagate along and sweep surface 128 of first electrode 116. The gas bubbles may entrain and/or sweep NO generated at and/or near the surface of first electrode 116 out of reaction medium 112, which may reduce or prevent generated NO from being dissolved in reaction medium 112.

In some embodiments, as shown in FIGS. 1 and 2, NO generation apparatus 100 includes a liquid-gas separation circuit 400 to reduce or remove NO dissolved in reaction medium 112. Liquid-gas separation circuit 400 is configured to circulate a fluid flow, such as a liquid flow or a gas flow, relative to reaction chamber 102. Liquid-gas separation circuit 400 may be used before, during, and/or after reusing reaction medium 112 for generating NO.

In some embodiments, as shown in FIG. 2, liquid-gas separation circuit 400 includes a first port 402 and a second port 410. In some embodiments, first port 402 is in fluid communication with liquid region 108. First port 402 may include an opening in liquid region 108 of reaction chamber 102, for example, below the level of reaction medium 112. In some embodiments, second port 410 is in fluid communication with gas region 110. Second port 410 may have an opening in gas region 110 of reaction chamber 102, for example, above the level of reaction medium 112. In some embodiments, liquid-gas separation circuit 400 is configured to circulate a flow of reaction medium 112 relative to reaction chamber 102 from first port 402 to second port 410. In some embodiments, liquid-gas separation circuit 400 is configured to circulate a flow of product gas relative to reaction chamber 102 from second port 410 to first port 402.

In some embodiments, liquid-gas separation circuit 400 includes a pump 406. In some embodiments, pump 406 is a liquid-gas dual purpose pump. In some embodiments, pump 406 is a reversible pump. Pump 406 may create a fluid flow from first port 402 to second port 410 or from second port 410 to first port 402. In some embodiments, the fluid flow is a liquid flow. For example, pump 406 may create a flow of reaction medium 112 from first port 402 to second port 410. In some embodiments, the fluid flow is a gas flow. For example, pump 406 may create a flow of product gas from second port 410 to first port 402.

Pump 406 may create a fluid flow at any suitable flow rate. For example, pump 406 may create a fluid flow, such as a flow of the reaction medium, at a flow rate from about 0.25 L/min to about 10 L/min, such as from about 0.5 L/min to about 1.0 L/min, from about 1.0 L/min to about 1.5 L/min, from about 1.5 L/min to about 2.0 L/min, from about 2.0 L/min to about 2.5 L/min, from about 2.5 L/min to about 3.0 L/min, from about 3.0 L/min to about 3.5 L/min, from about 3.5 L/min to about 4.0 L/min, from about 4.0 L/min to about 4.5 L/min, from about 4.5 L/min to about 5.0 L/min, from about 5.0 L/min to about 5.5 L/min, from about 5.5 L/min to about 6.0 L/min, from about 6.0 L/min to about 6.5 L/min, from about 6.5 L/min to about 7.0 L/min, from about 7.0 L/min to about 7.5 L/min, from about 7.5 L/min to about 8.0 L/min, from about 8.0 L/min to about 8.5 L/min, from about 8.5 L/min to about 9 L/min, from about 9.0 L/min to about 9.5 L/min, from about 9.5 L/min to about 10 L/min, or a combination of thereof.

In some embodiments, as shown in FIGS. 1 and 2, liquid-gas separation circuit 400 includes a liquid-gas separation device 408. In some embodiments, liquid-gas separation device 408 is disposed between first port 402 and second port 410. Liquid-gas separation device 408 may be disposed downstream or upstream of pump 406. In some embodiments, liquid-gas separation device 408 includes at least one first chamber 414 and at least one second chamber 416. First chamber 414 and/or second chamber 416 may have any suitable shapes and sizes. For example, first chamber 414 and/or second chamber 416 may have a tubular structure. First chamber 414 may be received in second chamber 416, or vice versa. In some embodiments, liquid-gas separation device 408 includes a shell or housing configured to enclose first chamber 414 and second chamber 416.

In some embodiments, first chamber 414 and second chamber 416 are separated by a separation membrane. The separation membrane may include a material permeable to NO. For example, the separation membrane may include a material, such as polydimethylsiloxane (PDMS), silicone, or polypropylene. NO may diffuse from a liquid in first chamber 414, through the separation membrane, to a gas in second chamber 416. The separation membrane may have any suitable configuration. For example, a plurality of hollow fibers having walls formed by the separation membrane.

The separation membrane may be selected to have any suitable area that allows for reducing or removing NO dissolved in reaction medium 112 over a certain period and/or amount of circulation. In some embodiments, the separation membrane of liquid-gas separation device 408 has a surface area ranging from about 500 cm$^2$ to about 50000 cm$^2$, such as from about 500 cm$^2$ to about 1000 cm$^2$, from about 1000 cm$^2$ to about 5000 cm$^2$, from about 5000 cm$^2$ to about 10000 cm$^2$, from about 10000 cm$^2$ to about 15000 cm$^2$, from about 15000 cm$^2$ to about 20000 cm$^2$, from about 20000 cm$^2$ to about 25000 cm$^2$ from about 25000 cm$^2$ to about 30000 cm$^2$, from about 30000 cm$^2$ to about 35000 cm$^2$, from about 35000 cm$^2$ to about 40000 cm$^2$, from about 40000 cm$^2$ to about 45000 cm$^2$, from about 45000 cm$^2$ to about 50000 cm$^2$, or a combination thereof.

In some embodiments, first chamber 414 includes an inlet 418 and an outlet 420. Pump 406 may drive reaction medium 112 from inlet 418, through first chamber 414, to outlet 420. NO dissolved in reaction medium 112 may diffuse through the separation membrane into second chamber 416 as reaction medium 112 flow through first chamber 414. In some embodiments, second chamber 416 includes an inlet 422 and an outlet 426. A sweep gas may flow from inlet 422, through second chamber 416, to outlet 426. The sweep gas may transport NO diffused into second chamber 416 out of outlet 426 as a mixed gas. The mixed gas may be transported to a waste gas treatment device 700 as described further below.

The sweep gas may include any suitable gas, such as air, oxygen, and nitrogen, or a combination thereof. The sweep gas may be supplied to inlet 422 from a gas source, such as carrier gas source 200. In some embodiments, carrier gas 122 is used as the sweep gas. For example, a fluid control 424 may be used to control the flow of carrier gas 122 from carrier gas source 200 to inlet 422. Fluid control 424 may include a pressure control, such as a pressure control valve or a pressure regulator.

In some embodiments, as shown in FIG. 2, NO generation apparatus 100 includes a filtration device 412. In some embodiments, filtration device 412 is disposed upstream of liquid-gas separation device 408. Filtration device 412 may include one or more filters configured to filter one or more impurities, such as solid matter, from reaction medium 112. Filtration device 412 may protect the separation membrane of liquid-gas separation device 408 from being damaged by the impurities in reaction medium 112 as reaction medium 112 flows therethrough.

In some embodiments, liquid-gas separation circuit 400 has a working mode and a cleaning mode. In the working mode, liquid-gas separation circuit 400 may reduce or remove NO dissolved in reaction medium 112 by circulating reaction medium 112 from first port 402, through liquid-gas separation device 408, to second port 410. In the cleaning mode, gas in gas region 110 of reaction chamber 102 may be circulated from second port 410, through liquid-gas separation device 408, to first port 402. Circulating gas through liquid-gas separation device 408 may transport residual reaction medium 112 in liquid-gas separation device 408 after the working mode back to reaction chamber 102. For example, pump 406 may create a fluid flow, such as a flow of the gas in gas region 110, at a flow rate from about 0.25 L/min to about 5 L/min, such as from about 0.25 L/min to about 0.5 L/min, from about 0.5 L/min to about 1.0 L/min, from about 1.0 L/min to about 1.5 L/min, from about 1.5 L/min to about 2.0 L/min, from about 2.0 L/min to about 2.5 L/min, from about 2.5 L/min to about 3.0 L/min, from about 3.0 L/min to about 3.5 L/min, from about 3.5 L/min to about 4.0 L/min, from about 4.0 L/min to about 4.5 L/min, from about 4.5 L/min to about 5.0 L/min, or a combination thereof. The cleaning mode may reduce loss of reaction medium 112 and may extend the life of reaction medium 112 and/or of NO generation apparatus 100. The cleaning mode may dry the separation membrane and prepare it for the next working mode.

In some embodiments, as shown in FIG. 2, liquid-gas separation circuit 400 includes a switching valve 404 for switching liquid-gas separation circuit 400 between the working mode and cleaning mode. In some embodiments, switching valve 404 includes one or more valves configured to control the direction of a fluid flow of liquid-gas separation circuit 400. For example, switching valve 404 may include a set of normally closed valves, and may change the direction of the fluid flow in liquid-gas separation circuit 400 by turning different subsets of valves open. In such instances, pump 406 may not need to be a reversible pump to operate in the working mode and cleaning mode.

For example, as shown in FIG. 2, switching valve 404 may include a set of four valves 404a-404d. In some instances, valve 404a is disposed between first port 402 and pump 406; valve 404b is disposed between first port 402 and fluid outlet 420 of first chamber 414; valve 404c is disposed between second port 410 and pump 406; and valve 404d is disposed between second port 410 and fluid outlet 420 of first chamber 414. In the working mode, for example, valves 404a and 404d are open, and valves 404b and 404c are closed. Reaction medium 112 may flow from first port 402, through valve 404a, pump 406, fluid inlet 418 and fluid outlet 420 of liquid-gas separation device 408, and valve 404d, and to second port 410. In the cleaning mode, for example, valves 404a and 404d are closed, and valves 404b and 404c are open. Gas in gas region 110 of reaction chamber 102 may flow from second port 410, through valve 404c, pump 406, fluid inlet 418 and fluid outlet 420 of liquid-gas separation device 408, and valve 404b, and to first port 402.

In some embodiments, liquid-gas separation circuit 400 includes an electromagnetic valve (not shown). The electromagnetic valve may be disposed upstream of liquid-gas separation device 408. The electromagnetic valve may prevent reaction medium 112 from entering liquid-gas separation device 408 due to pressure that may be accumulated in reaction medium 112 during electrochemical generation of NO.

Figure 4C:
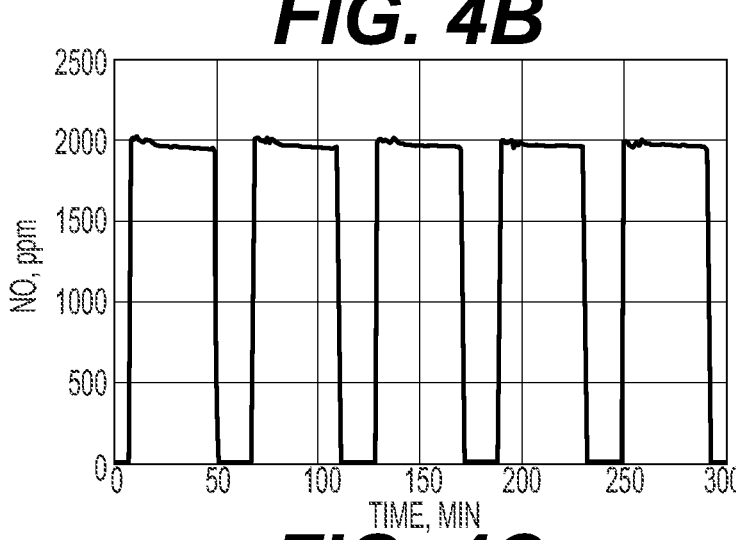
FIG. 4C is a graphical representation of concentrations of NO in a product gas generated by an NO generation apparatus over a plurality of sessions, according to some embodiments of the present disclosure.

FIG. 4C is a graphical representation of concentrations of NO in a product gas generated by an NO generation apparatus 100 over a plurality of sessions, according to some embodiments of the present disclosure. In this example, the NO generation apparatus 100 can have the same reaction conditions as described in the example above with reference to FIG. 4A except that a current of 50 mA can be applied to first electrode 116 after an initial application of a current of about 150 mA over a ramp period of about 2 minutes over a plurality of sessions. The NO generation apparatus 100 can also include a liquid-gas separation circuit 400. After terminating the current applied to the first electrode 116 in each session, the liquid-gas separation circuit 400 can operate in the working mode and circulate the reaction medium 112 through the liquid-gas separation device 408 at a flow rate of about 0.5 L/min for about 10 minutes to reduce or remove NO dissolved in the given reaction medium 112. The liquid-gas separation circuit 400 can then can operate in the cleaning mode and circulate the gas in the gas region 110 through the liquid-gas separation device 408 at a flow rate of about 1 L/min for about 0.5 min. As shown in FIG. 4C, NO generation apparatus 100, using the reaction medium 112, can generate a product gas having a concentration of NO around 2000 ppm over five consecutive sessions.

Some examples of NO system are provided below. In some examples, NO system 10 can include an NO generation apparatus 100 and a carrier gas source 200. The NO generation apparatus 100 can include a reaction chamber 102 having a gas region and a liquid region, a reaction medium 112 contained in the liquid region, a cathode and an anode disposed in the reaction medium 112, two spargers 134, a gas circulation circuit 300, and a liquid-gas separation circuit 400. The spargers 134 can be disposed adjacent the two electrodes respectively and configured to emanate bubbles to propagate across the surface of the electrodes. The carrier gas source 200 can generate a carrier gas 122 from compressed air. The carrier gas source 200 can include a moisture filter and a dust filter to reduce or remove moisture and solid matter from the compressed air. The carrier gas source 200 can further include a nitrogen generating apparatus 202 having a nitrogen separation membrane to separate $N_2$ from the compressed air. The cathode and the anode can be electrically connected to a power supply. The power supply can apply a current or a voltage to the cathode and NO can be generated at or adjacent the surface of the cathode and be swept or entrained by the carrier gas 122 to the gas region to generate a product gas. The gas circulation circuit 300 can recirculate the product gas from the gas region to the spargers. The recirculated gas can be combined with the carrier gas 122 to be introduced to the spargers. The liquid-gas separation circuit 400 can include a liquid-gas separation device 408 to separate NO dissolved in the reaction medium after terminating applying the voltage or current to the cathode while the current or voltage is being applied to the cathode. The liquid-gas separation device 408 can include a separation membrane having a surface area. The liquid-gas separation circuit 400 can operate in a working mode for a first period and can operate in a cleaning mode for a second period after the first period.

For example, the cathode and anode can be made of platinum. The reaction medium can include about 0.01 mol/L HEPES buffer, about 0.01 mol/L sodium nitrite, and about 1 mmol/L Cu-tris(2-pyridylmethyl)amine (CuTPMA).

A suitable base solution, such as a NaOH solution can be used to titrate the HEPES buffer such that the reaction medium can have a pH anywhere from about 6 to about 8, such as a pH of about 7.2. A stimulation current of about 20 mA can be applied to the cathode for about 0.5 minute before applying a current of about 10 mA to the cathode. The nitrogen separation membrane of the nitrogen generating apparatus 202 can be made of poly(4-methyl-1-pentene) and can have an average pore size of about 0.01 μm. The nitrogen generating apparatus 202 can generate, from the compressed air, a carrier gas 122 containing $N_2$ at a concentration of about 99.0% by volume. The carrier gas 122 can be introduced to the spargers 134 at a flow rate of about 50 mL/min. The gas circulation circuit 300 can recirculate the product gas at a flow rate of about 0.5 L/min. After applying the current to the cathode for a ramp period of about 10 minutes, the NO generation apparatus 100 may output a product gas having an NO concentration of about 200 ppm. After terminating applying the current to the cathode, the liquid-gas separation circuit 400 can operate in a working mode for about 10 minutes and can operate in a cleaning mode for about 1 minute thereafter. The separation membrane of the liquid-gas separation device 408 can have a surface area of about 25000 cm².

For another example, the cathode and anode can be made of gold. The reaction medium can include about 1 mol/L MOPS buffer, about 1 mol/L sodium nitrite, and about 3 mmol/L Fe-1,4,7-triazacyclononane. A suitable base solution, such as a NaOH solution can be used to titrate the MOPS buffer such that the reaction medium can have a pH anywhere from about 6 to about 8, such as a pH of about 7.2. A stimulation voltage of about 4.2 V can be applied to the cathode for about 1 minute before applying a voltage of about 1.4 V to the cathode. The nitrogen separation membrane of the nitrogen generating apparatus 202 can be made of brominated polycarbonate and can have an average pore size of about 0.02 μm. The nitrogen generating apparatus 202 can generate, from the compressed air, a carrier gas 122 containing $N_2$ at a concentration of about 99.6% by volume. The carrier gas 122 can be introduced to the spargers 134 at a flow rate of about 100 mL/min. The gas circulation circuit 300 can recirculate the product gas at a flow rate of about 1 L/min. After applying the voltage to the cathode for a ramp period of about 9 minutes, the NO generation apparatus 100 may output a product gas having an NO concentration of about 1200 ppm. After terminating applying the voltage to the cathode, liquid-gas separation circuit 400 can operate in a working mode for about 5 minutes and can operate in a cleaning mode for about 0.5 minute thereafter. The separation membrane of the liquid-gas separation device 408 can have a surface area of about 1000 cm².

For another example, the cathode and anode can be made of carbon. The reaction medium can include about 1.5 mol/L Tris buffer, about 2 mol/L potassium nitrite, and about 4 mmol/L Ti(Me₃TACN). A suitable base solution, such as a NaOH solution can be used to titrate the Tris buffer such that the reaction medium can have a pH anywhere from about 6 to about 8, such as a pH of about 7.2. A stimulation current of about 500 mA can be applied to the cathode for about 1.5 minutes before applying a current of about 100 mA to the cathode. The nitrogen separation membrane of the nitrogen generating apparatus 202 can be made of polypropylene, and can have an average pore size of about 0.012 μm. The nitrogen generating apparatus 202 can generate, from the compressed air, a carrier gas 122 containing $N_2$ at a concentration of about 99.7% by volume. The carrier gas 122 can be introduced to the spargers 134 at a flow rate of about 200 mL/min. The gas circulation circuit 300 can recirculate the product gas at a flow rate of about 1.5 L/min. After applying the current to the cathode for a ramp period of about 6 minutes, the NO generation apparatus 100 may output a product gas having an NO concentration of about 3000 ppm. After terminating applying the current to the cathode, liquid-gas separation circuit 400 can operate in a working mode for about 12 minutes and can operate in a cleaning mode for about 0.9 minute thereafter. The separation membrane of the liquid-gas separation device 408 can have a surface area from about 1000 cm$^2$ to about 50000 cm$^2$, such as about 50000 cm$^2$.

For another example, the cathode and anode can be made of SiO$_2$ coated with glassy carbon. The reaction medium can include about 2 mol/L MOPS buffer, about 3 mol/L sodium nitrite, and about 5 mmol/L Cr-tris(2-pyridylmethyl)amine (CrTPMA). A suitable base solution, such as a NaOH solution can be used to titrate the MOPS buffer such that the reaction medium can have a pH anywhere from about 6 to about 8, such as a pH of about 7.2. A stimulation voltage of about 12 V can be applied to the cathode for about 2 minutes before applying a voltage of about 2 V to the cathode. The nitrogen separation membrane of the nitrogen generating apparatus 202 can be made of polyimide and can have an average pore size of about 0.005 μm. The nitrogen generating apparatus 202 can generate, from the compressed air, a carrier gas 122 containing N$_2$ at a concentration of about 99.99% by volume. The carrier gas 122 can be introduced to the spargers 134 at a flow rate of about 300 mL/min. The gas circulation circuit 300 can recirculate the product gas at a flow rate of about 2 L/min. After applying the voltage to the cathode for a ramp period of about 5 minutes, the NO generation apparatus 100 may output a product gas having an NO concentration of about 4200 ppm. After terminating applying the voltage to the cathode, liquid-gas separation circuit 400 can operate in a working mode for about 5 minutes and can operate in a cleaning mode for about 1.5 minutes thereafter. The separation membrane of the liquid-gas separation device 408 can have a surface area from about 1000 cm$^2$ to about 5000 cm$^2$, such as about 37500 cm$^2$.

For another example, the cathode and anode can be made of conductive glass coated with stainless steel. The reaction medium can include about 2.5 mol/L phosphate buffer, about 4 mol/L sodium nitrite, and about 6 mmol/L Mn-tris(2-pyridylmethyl)amine (MnTPMA). A suitable base solution, such as a NaOH solution can be used to titrate the phosphate buffer such that the reaction medium can have a pH anywhere from about 6 to about 8, such as a pH of about 7.2. A stimulation current of about 1.4 A can be applied to the cathode for about 2.5 minutes before applying a current of about 200 mA to the cathode. The nitrogen separation membrane of the nitrogen generating apparatus 202 can be made of polydimethylsiloxane (PDMS) and can have an average pore size of about 0.008 μm. The nitrogen generating apparatus 202 can generate, from the compressed air, a carrier gas 122 containing N$_2$ at a concentration of about 99.8% by volume. The carrier gas 122 can be introduced to the spargers 134 at a flow rate of about 400 mL/min. The gas circulation circuit 300 can recirculate the product gas at a flow rate of about 2.5 L/min. After applying the current to the cathode for a ramp period of about 4.6 minutes, the NO generation apparatus 100 may output a product gas having an NO concentration of about 6300 ppm. After terminating applying the current to the cathode, liquid-gas separation circuit 400 can operate in a working mode for about 20 minutes and can operate in a cleaning mode for about 2 minutes thereafter. The separation membrane of the liquid-gas separation device 408 can have a surface area from about 1000 cm$^2$ to about 5000 cm$^2$, such as about 12500 cm$^2$.

For another example, the cathode and anode can be made of stainless steel coated with iridium-ruthenium alloy. The reaction medium can include about 3 mol/L boric acid-borax buffer, about 5 mol/L potassium nitrite, and about 7 mmol/L Co-(Bis(2-aminothypridine)propionic acid. A suitable base solution, such as a NaOH solution can be used to titrate the boric acid-borax buffer such that the reaction medium can have a pH anywhere from about 6 to about 8, such as a pH of about 7.2. A stimulation voltage of about 24 V can be applied to the cathode for about 3 minutes before applying a voltage of about 3 V to the cathode. The nitrogen separation membrane of the nitrogen generating apparatus 202 can be made of brominated polycarbonate and can have an average pore size of about 0.015 μm. The nitrogen generating apparatus 202 can generate, from the compressed air, a carrier gas 122 containing N$_2$ at a concentration of about 99.9% by volume. The carrier gas 122 can be introduced to the spargers 134 at a flow rate of about 600 mL/min. The gas circulation circuit 300 can recirculate the product gas at a flow rate of about 3 L/min. After applying the voltage to the cathode for a ramp period of about 5 minutes, the NO generation apparatus 100 may output a product gas having an NO concentration of about 10400 ppm. After terminating applying the current to the cathode, liquid-gas separation circuit 400 can operate in a working mode for about 18 minutes and can operate in a cleaning mode for about 1.6 minutes thereafter. The separation membrane of the liquid-gas separation device 408 can have a surface area from about 1000 cm$^2$ to about 5000 cm$^2$, such as about 5000 cm$^2$.

Product Gas Filtration

System 10 may include one or more filtration systems or devices to reduce or remove one or more impurities in the product gas. In some embodiments, as shown in FIG. 1, system 10 includes a filtration system 500 disposed downstream of NO generation apparatus 100. For example, filtration system 500 may be disposed downstream of and in fluid communication with gas region 110 and/or outlet circuit 124 of NO generation apparatus 100. Filtration system 500 may reduce or remove one or more impurities in the product gas from NO generation apparatus 100, such as moisture and/or solid matter. As described herein, moisture may include any liquid, in vapor phase or in liquid phase, that may be present in the product gas, such as water vapor, water droplets, solvent vapor, and solvent droplets.

Filtration system 500 may include one or more filtration devices or filters. In some embodiments, filtration system 500 includes one or more solid matter filters 502. It is contemplated that solid matter filter 502 may be configured to filter any type of solid matter by, for example, modifying or selecting the filter material and/or pore size. In one embodiment, solid filter 502 may be a salt aerosol filter. In some embodiments, solid matter filter 502 includes a membrane filter. The membrane filter may include a polymeric material that has a porous structure. For example, the polymeric material may include one or more selected from polytetrafluoroethylene (PTEF), polyvinylidene fluoride, polyethersulfone, mixed cellulose ester, polyamide (nylon), nylon 6, and nylon 66. The porous structure may have an average pore size ranging from about 0.01 μm to about 2 μm, such as from about 0.1 μm to about 0.2 μm, from about 0.2 μm to about 0.4 μm, from about 0.4 μm to about 0.6 μm, from about 0.6 μm to about 0.8 μm, from about 0.8 μm to about 1.0 μm, from about 1.0 μm to about 1.2 μm, from about 1.2 μm to about 1.4 μm, from about 1.4 μm to about 1.6 µm, from about 1.6 µm to about 1.8 µm, from about 1.8 µm to about 2.0 µm, or a combination thereof.

In one example, solid matter filter 502 can include a member filter made of PTEF having an average pore size of about 1.0 µm. In another example, solid matter filter 502 can include a member filter made of polyvinylidene fluoride having an average pore size of about 0.1 µm. In another example, solid matter filter 502 can include a member filter made of polyethersulfone having an average pore size of about 2.0 µm. In another example, solid matter filter 502 can include a member filter made of nylon 6 having an average pore size of about 0.1 µm. In another example, solid matter filter 502 can include a member filter made of nylon 66 having an average pore size of about 0.8 µm. In another example, solid matter filter 502 can include a member filter made of mixed cellulose ester having an average pore size of about 1.6 µm.

In some embodiments, filtration system 500 includes one or more moisture filters 504. Moisture filter 504 may reduce or remove liquid, such as water, in the vapor phase and/or the liquid phase. In some embodiments, moisture filter 504 includes a membrane filter. In some embodiments, the membrane filter includes a polymeric material. The polymeric material may have a porous structure. The polymeric material may absorb liquid vapor and/or liquid droplets. Additionally or alternatively, the polymeric material may be at least partially permeable to liquid vapor and/or liquid droplets. For example, the membrane filter may include a Nafion™ membrane.

In some embodiments, filtration system 500 includes one or more additional filter 506. Filter 506 may be disposed downstream of solid matter filter 502 and/or moisture filter 504 to further remove or reduce impurities, such as moisture and/or solid matter, from the product gas. In some embodiments, filter 506 includes a membrane filter. In some embodiments, the membrane filter includes a polymeric material. In some embodiments, the membrane filter has a porous structure. For example, a polymeric material of the membrane filter may have a porous structure. The porous structure may have an average pore size ranging from about 0.01 µm to about 2 µm, such as from about 0.01 µm to about 0.1 µm, from about 0.1 µm to about 0.2 µm, from about 0.2 µm to about 0.3 µm, from about 0.3 µm to about 0.4 µm, from about 0.4 µm to about 0.5 µm, from about 0.5 µm to about 1.0 µm, from about 1.0 µm to about 2 µm, or a combination thereof. In some embodiments, the average pore size of filter 506 is equal to or smaller than the average pore size of solid matter filter 502.

As described herein, a membrane filter used in some embodiments of the present disclosure may include at least one membrane that may have any suitable configuration for filtering or separating gas, liquid, and/or solid. For example, a membrane of a membrane filter may be configured for dead-end filtration in which a fluid may pass through the membrane, and components to be separated out from the fluid may be blocked or trapped by the membrane. Alternatively, a membrane of a membrane filter may be configured for cross-flow filtration in which a fluid may pass across the surface of the membrane on a feed side, and components to be separated out from the fluid may be retained on the feed side or permeate through the membrane to the permeate side. An example configuration for cross-flow filtration is one or more hollow fibers formed by the membrane.

The product gas output from gas region 110 of NO generation apparatus 100, for example, may include an amount of liquid or solid impurities, such as water and salt aerosol. Such amount of impurities may damage and/or affect the life of downstream devices, such as pump 306 and one or more of filters 502-506. In some embodiments, filtration system 500 includes a filtration device 508 disposed downstream of NO generation apparatus 100. In some embodiments, filtration device 508 is disposed upstream of pump 306 to reduce or remove liquid and/or solid impurities from recirculated product gas 303. For example, the product gas output from gas region 110 of NO generation apparatus 100 may include one or more impurities, such as droplets or vapor of water or reaction medium 112. In some embodiments, filtration device 508 is disposed upstream of solid matter filter 502 and/or moisture filter 504. Filtration device 508 may reduce or remove liquid and/or solid impurities from the product gas before product gas flows through one or more of filters 502-506.

Figure 5A:
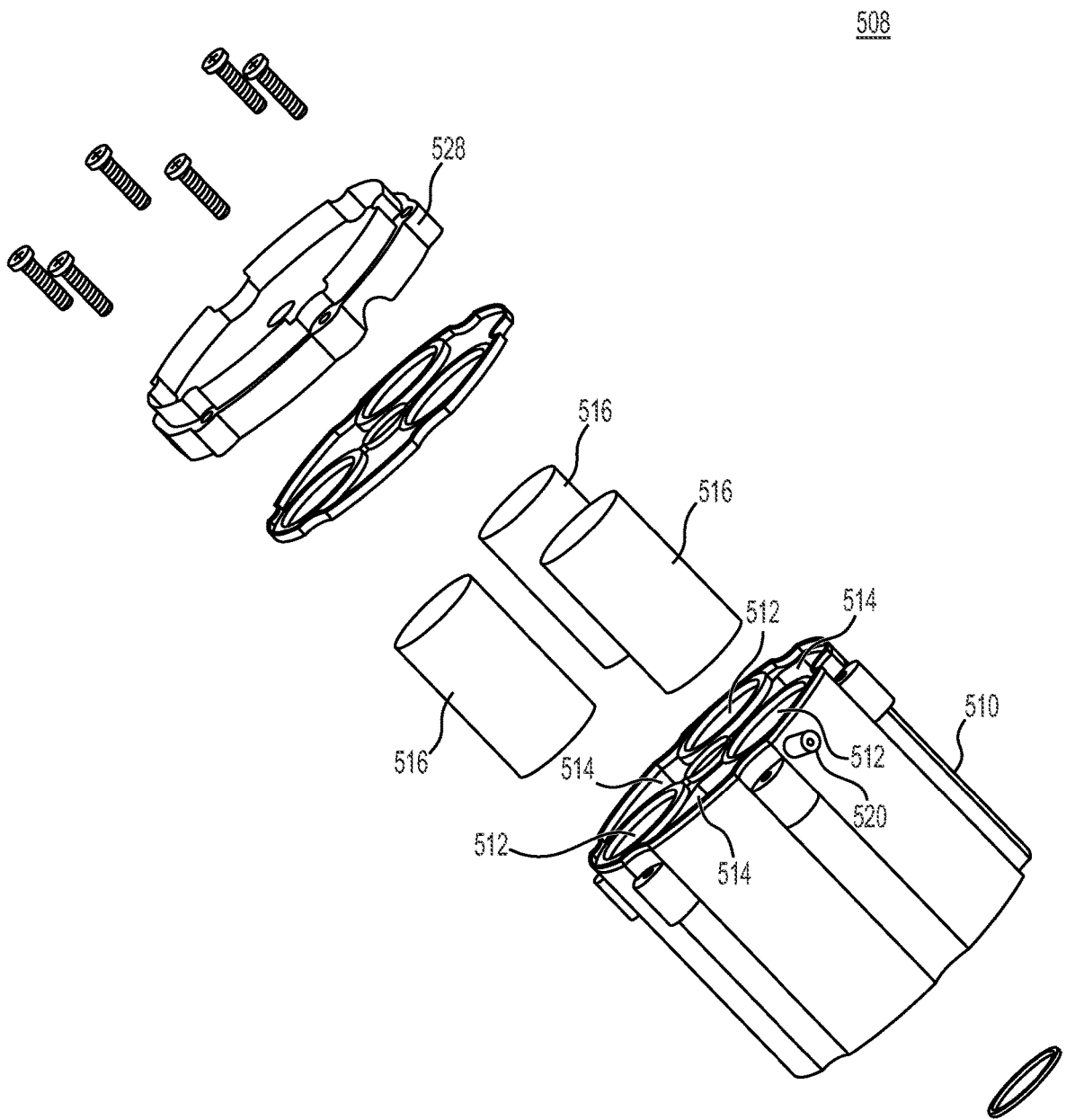
FIG. 5A is an exploded view of a filtration device, according to some embodiments of the present disclosure.
Figure 5C:
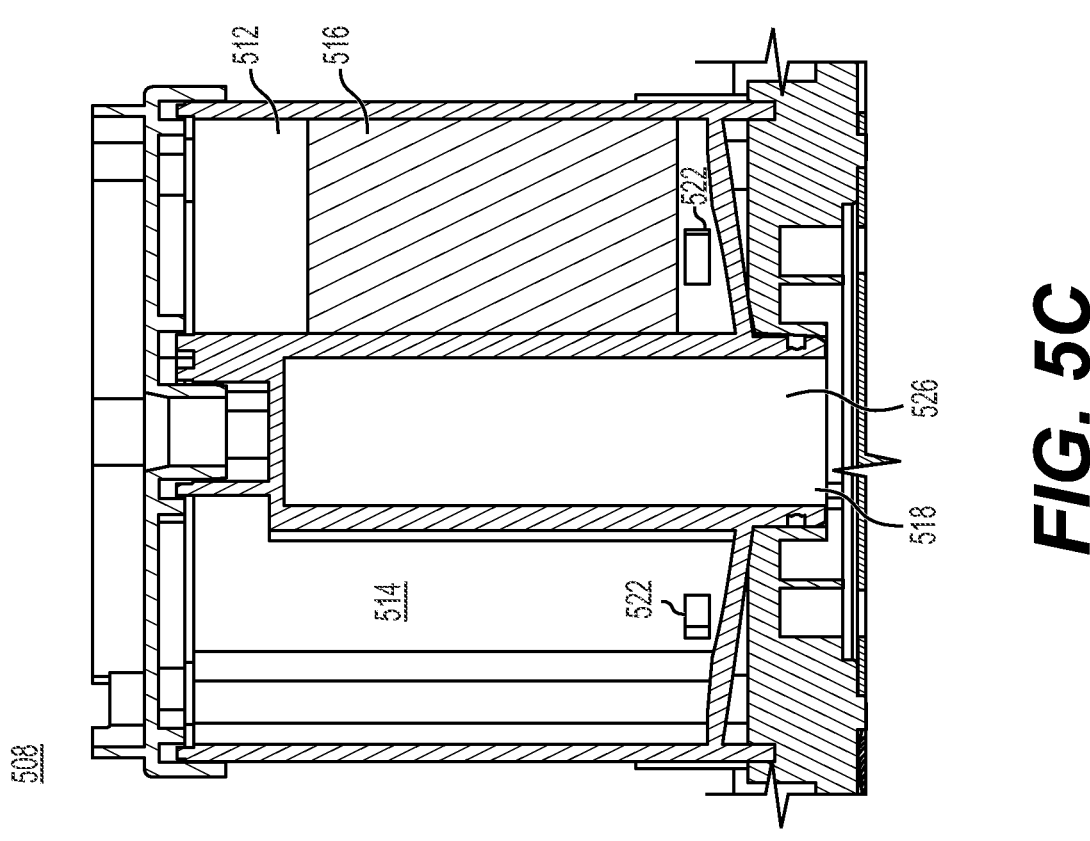
FIG. 5C is a cross-sectional view of the filtration device of FIG. 5A.
Figure 5B:
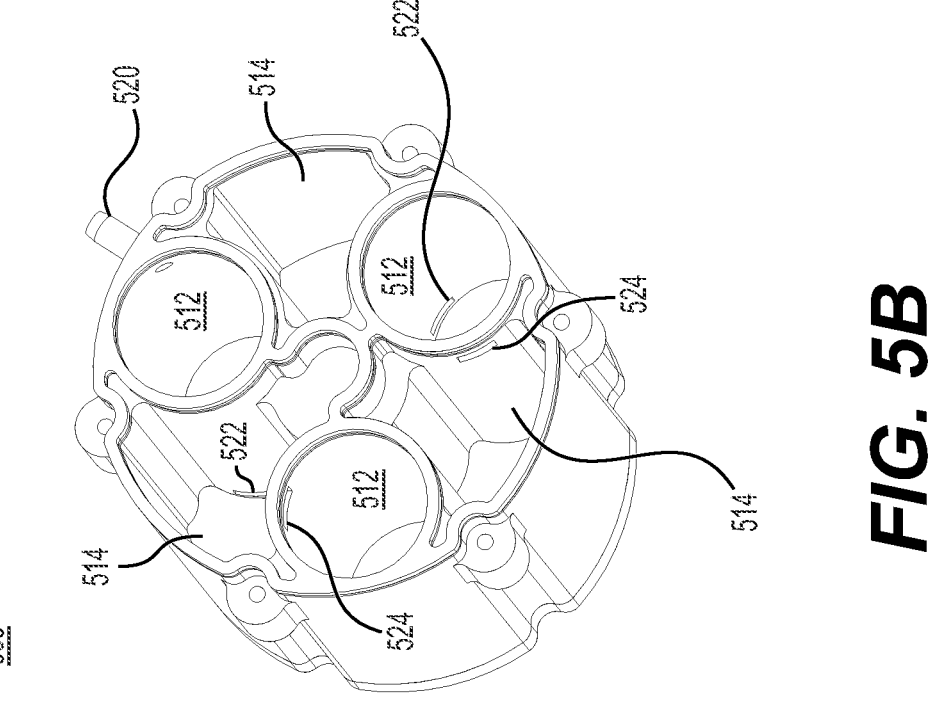
FIG. 5B is a cross-sectional perspective view of the filtration device of FIG. 5A.

FIGS. 5A-5C illustrate a filtration device 508, according to some embodiments of the present disclosure. As shown in FIGS. 5A-5C, in some embodiments, filtration device 508 includes a housing 510, an inlet 518, and an outlet 520. In some embodiments, filtration device 508 includes at least one chamber disposed in housing 510. Inlet 518 and/or outlet 520 may be in fluid communication with at least one chamber in housing 510. Housing 510 may have any suitable shape, such as a cylindrical shape. As shown in FIG. 5C, inlet 518 may be disposed at a bottom portion of housing 510 in fluid communication with a chamber. Outlet 520 may be disposed at a top portion of housing 510 in fluid communication with a chamber.

In some embodiments, as shown in FIG. 5B, filtration device 508 includes one or more filter chambers 512. Filter chamber 512 may have any suitable shape, such as a cylindrical shape. Filter chambers 512 may be arranged around the longitudinal axis of housing 510, and may be equally or unequally spaced. Filtration device 508 may include any suitable number of filter chambers 512, such as 2 to 5. For example, three filter chambers 512 may be equally spaced about 120 degrees apart around the longitudinal axis of housing 510.

Each filter chamber 512 may have an inlet 522 and an outlet 524. The inlets and outlets of one or more filter chambers 512 may define a flow path. One or more filter chambers 512, such as a first filter chamber 512, may have an inlet 522 in fluid communication with inlet 518 of housing 510. One or more filter chambers 512, such as a last filter chamber 512, may have an outlet 524 in fluid communication with outlet 520 of housing 510. In some embodiments, a filter chamber 512 includes a filter material 516 configured to reduce or remove one or more impurities in a fluid that passes therethrough. Filter material 516 may fill at least a portion of filter chamber 512, such as a middle portion of filter chamber 512. Filter material 516 may include any suitable material, such as silica gel, sponge, cotton, polypropylene (e.g., PP cotton filter), foam, and foam resin.

In some embodiments, filtration device 508 includes a feed chamber 526. Feed chamber 526 may be in fluid communication with inlet 518 for receiving a fluid, such as a gas flow, to be filtered. Feed chamber 526 may be in fluid communication with one or more filter chambers 512. For example, feed chamber 526 may have an outlet in fluid communication with inlet 522 of a filter chamber 512. In some embodiments, feed chamber 526 extends through a middle portion of housing 510 such that a cavity is formed between feed chamber 526 and an inner surface of housing 510.

For example, as shown in FIGS. 5A-5C, housing 510 may have a cylindrical shape. Feed chamber 526 may have a cylindrical shape extending along at least a portion of a longitudinal axis of housing 510. An annular space formed between feed chamber 526 and housing 510 may form a cavity. In some embodiments, one or more chambers, such as filter chamber 512, are disposed in the cavity between feed chamber 526 and housing 510.

Filtration device 508 may be configured to allow at least some liquid and/or solid impurities in a gas, such as the product gas output from gas region 110, to separate from the gas based on, for example, gravity settling or segregation. In some embodiments, inlet 522 of filter chamber 512 is disposed in a position vertically lower than outlet 524 such that liquid and/or solid particles suspended in the gas flowing from inlet 522 to outlet 524 may settle out of the gas and may settle to the bottom of filter chamber 512.

For example, filter chamber 512 may have an elongated shape, such as a cylindrical shape, and may be disposed in a vertical position along its longitudinal axis. In such a configuration, inlet 522 may be disposed at a bottom or lower portion of filter chamber 512 and outlet 524 may be disposed at a top or upper portion of filter chamber 512. A gas flow may enter filter chamber 512 from inlet 522, move or rise through at least a portion of filter chamber 512, to outlet 524. While moving or rising in filter chamber 512, the gas flow may pass through filter material 516, and liquid and/or solid impurities suspended in the gas flow may settle out and separate from the gas flow.

In some embodiments, filtration device 508 includes a buffer chamber 514 in in fluid communication with filter chamber 512. For example, buffer chamber 514 may be fluidly connected to filter chamber 512 via an opening or a port, at a bottom portion of filter chamber 512. A gas to be filtered, such as a gas flow, may flow from buffer chamber 514 to filter chamber 512 via the opening or port, rise in filter chamber 512, and exit from outlet 524. Liquid and/or solid matter settled out of the gas in filter chamber 512 may settle to a bottom portion of filter chamber 512. The settled liquid and/or solid may flow to and accumulate in buffer chamber 514.

Liquid and/or solid matter accumulated in buffer chamber 514 may be transported out of filtration device 508 by any suitable means, such as by gravity or by pump. The liquid and/or solid matter transported out of filtration device 508 may be disposed or reused. For example, reaction medium 112 settled out of the product gas from NO generation apparatus 100 may be transported from buffer chamber 514 back to liquid region 108 of reaction chamber 102 and reused.

In some embodiments, as shown in FIG. 5C, buffer chamber 514 is fluidly connected to feed chamber 526. A fluid may flow from feed chamber 526 to buffer chamber 514 and from buffer chamber 514 to filter chamber 512. For example, a fluid to be filtered, such as a gas flow, may flow from inlet 518, though feed chamber 526, buffer chamber 514, and filter chamber 512, and to outlet 520.

In some embodiments, as shown in FIGS. 5A-5C, filtration device 508 includes two or more fluidly connected filter chambers 512 to allow for more than one settling processes. For example, outlet 524 of a first filter chamber 512 may be fluidly connected to inlet 522 of a second filter chamber 512. A gas may flow through two or more filter chambers 512 to allow liquid and/or solid impurities to settle out of the gas flow as the gas flow rise from inlet 522 to outlet 524 of each of the filter chambers.

In some embodiments, as shown in FIGS. 5A and 5B, buffer chamber 514 fluidly connects two filter chambers 512. Buffer chamber 514 may have openings or conduits configured to connect to the two filter chambers 512 such that a fluid may flow from inlet 522 to outlet 524 in each of two filter chambers 512. For example, as shown in FIG. 5B, outlet 524 of a first filter chamber 512 may be an inlet of buffer chamber 514 and inlet 522 of a second filter chamber 512 may be the outlet of buffer chamber 514. A fluid may flow from outlet 524 of a first filter chamber 512 to buffer chamber 514 and from buffer chamber 514 to inlet 522 of a second filter chamber 512. In such instances, as shown in FIG. 5B, outlet 524 of a first filter chamber 512 may be disposed at a top portion of buffer chamber 514 and inlet 522 of a second filter chamber 512 may be disposed at a bottom portion of buffer chamber 514.

Filtration device 508 may include one or more other components, such as components for covering or sealing one or more inlets, outlets, and/or chambers in housing 510. In some embodiments, as shown in FIG. 5A, filtration device 508 includes a seal configured to cover a top side of buffer chamber 514 to allow gas in buffer chamber 514 to flow from buffer chamber 514 to one or more of the filter chambers 512. In some embodiments, as shown in FIG. 5A, filtration device 508 includes a cover 528. Cover 528 may cover a top side of housing 510, and may cover a top side of filter chambers 512 to allow gas in filter chambers 512 to exit at outlet 524. Cover 528 may be secured to housing 510 via any suitable connection, such as by pressing fitting or using suitable fastening means, for example, screw fasteners. In some embodiments, as shown in FIG. 5A, filtration device 508 includes a sealing ring configured to form a seal around inlet 518.

Pressure Vessel

The flow rate and/or NO concentration of the product gas generated by NO generation apparatus 100 may vary due to variations of one or more conditions, such as temperature, the current or voltage applied to the electrode, side reactions, electrode degradation, or changes of concentrations of nitrite source and catalyst in reaction medium 112. System 10 may include one or more devices or systems, such as a pressure vessel, to stabilize the flow rate and/or NO concentration of the product gas generated by NO generation apparatus 100. Such devices or systems may allow system 10 to provide a steady supply of NO.

In some embodiments, as shown in FIG. 1, system 10 includes a pressure vessel 600. Pressure vessel 600 may be disposed downstream of and fluidly connected with NO generation apparatus 100. In some embodiments, pressure vessel 600 receives the product gas from outlet circuit 124 of NO generation apparatus 100. One or more filters of filtration system 500 may be disposed downstream of NO generation apparatus 100 and upstream of pressure vessel 600. The product gas from NO generation apparatus 100 may flow from outlet circuit 124, through one or more filters of filtration system 500, to pressure vessel 600. Filtration system 500 may reduce or remove one or more impurities, such as moisture and/or solid matter (e.g., salt aerosols), in the product gas before the product gas enters pressure vessel 600.

Figure 6A:
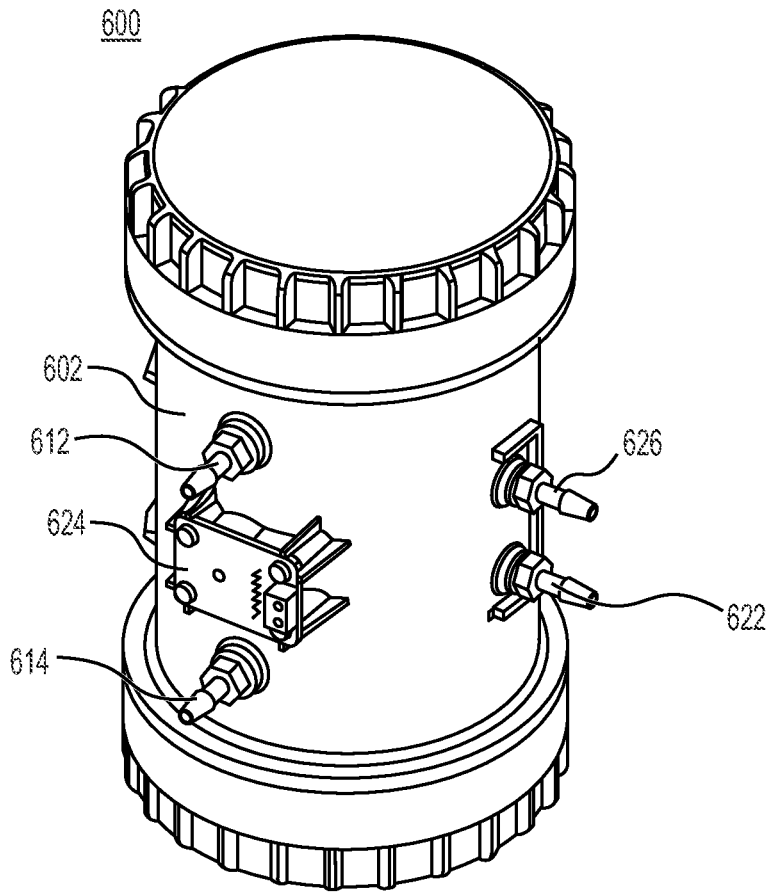
FIG. 6A is a perspective view of a pressure vessel, according to some embodiments of the present disclosure.

In some embodiments, as shown in FIG. 6A, pressure vessel 600 includes a body 602, a gas inlet 612, and a gas outlet 614. Body 602 may have any suitable shape, such as a cylindrical shape, configured to enclose an interior cavity. Gas inlet 612 and gas outlet 614 are fluidly connected with the interior cavity of body 602. For example, as shown in FIG. 6A, gas inlet 612 and/or gas outlet 614 may each have an opening or port disposed on body 602.

Pressure vessel 600 may receive and store the product gas from NO generation apparatus 100 for a pressure-holding period. The pressure in pressure vessel 600 may increase to a predetermined level or a predetermined range at the end of the pressure-holding period. Additionally, or alternatively, the concentration of NO in the product gas held in pressure vessel 600 may increase to a predetermined level or a predetermined range at the end of the pressure-holding period. The pressure-holding period may be predetermined and/or adjusted. In some embodiments, after a pressure-holding period, the product gas may be released from pressure vessel 600. NO concentration of the product gas released from pressure vessel 600 may increase over a ramp period, and may reach a steady state at the end of or after the ramp period.

In some embodiments, pressure vessel 600 is configured to reduce the pressure-holding period and the ramp period to allow for a more rapid or immediate provision of a steady supply of NO. For example, pressure vessel 600 may include one or more flow paths in the interior cavity of body 602. The one or more flow paths may include a circuitous flow path, such as a serpentine flow path. The one or more flow paths may allow the pressure and/or NO concentration of the product gas in at least one portion of the interior cavity of body 602 to quickly reach a steady state. For example, the one or more flow paths may allow for a new gas, such as the product gas, entering the interior cavity to quickly purge or deplete an old gas that preexists in at least a portion of the interior cavity, such as air or nitrogen. Additionally or alternatively, the one or more flow paths may reduce or eliminate uneven mixing of the new gas with the old gas.

As described herein, a circuitous flow path, such as a serpentine flow path, may refer to a non-direct flow path extending from a first point to a second point in any direction in a three-dimensional space. For example, a circuitous flow path may refer to a non-direct flow path extending from a first point to a second point across a cross-sectional plane and/or a longitudinal plane of pressure vessel 600.

Pressure vessel 600 may, for example, allow for a pressure-holding period less than about 60 min, such as less than about 1 min, less than about 5 min, less than about 10 min, less than about 20 min, less than about 30 min, less than about 40 min, or less than about 50 min. Pressure vessel 600 may, for example, allow for a ramp period less than about 20 min, such as less than about 1 min, less than about 2 min, less than about 3 min, less than about 4 min, less than about 5 min, less than about 8 min, or less than about 10 min.

Figure 6B:
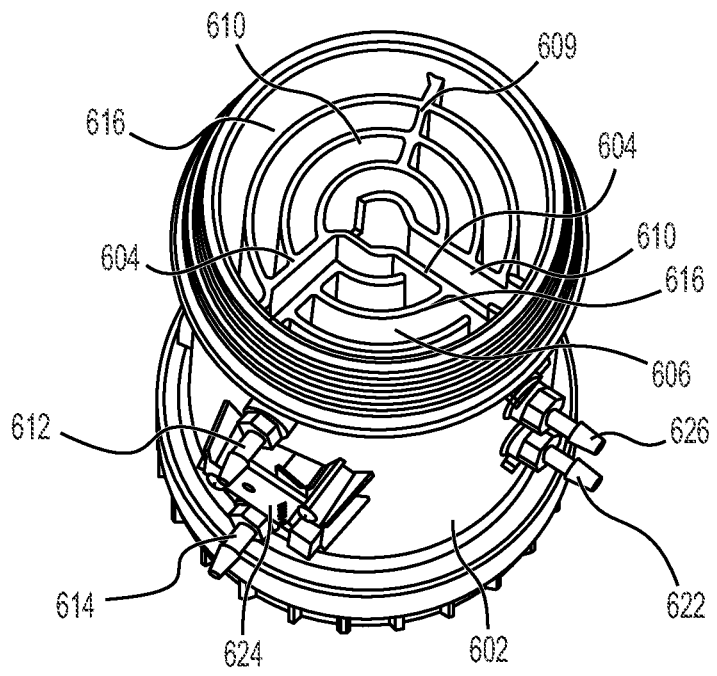
FIG. 6B is a cross-sectional perspective view of the pressure vessel of FIG. 6A.
Figure 6C:
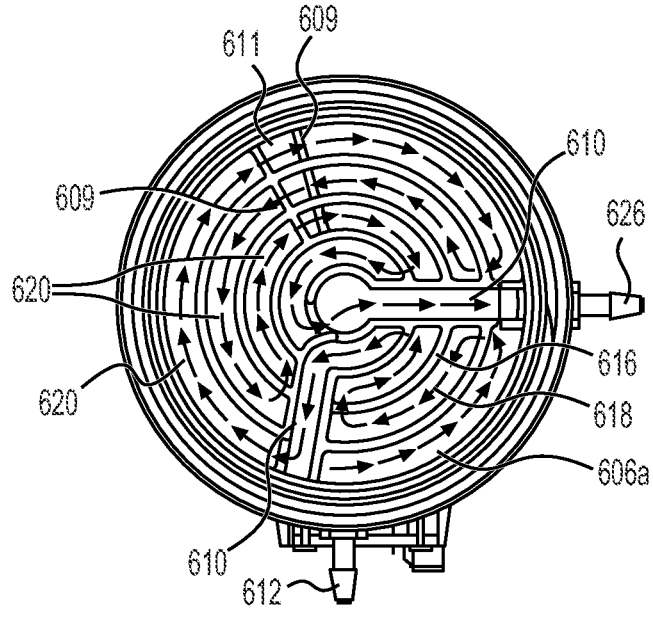
FIG. 6C is another cross-sectional view of the pressure vessel of FIG. 6A.

FIGS. 6A-6C are various views of a pressure vessel 600, according to some embodiments of the present disclosure. In some embodiments, pressure vessel 600 includes one or more panels or baffles 604 defining a plurality of fluidly connected regions in the interior cavity. The fluidly connected regions may form, in various configurations, a circuitous flow path, such as a serpentine flow path, through pressure vessel 600. For example, a plurality of panels 604 may divide the interior cavity to a first region 606 and a second region 608. First region 606 and second region 608 may be fluidly connected via, for example, an opening, port, or conduit. A fluid entering pressure vessel 600, such as the product gas, may enter first region 606 and may flow from first region 606 to second region 608 through the circuitous flow path. Alternatively, a fluid entering pressure vessel 600, such as the product gas, may enter first region 606 and may exit pressure vessel without flowing into or through second region 608, i.e., may bypass second region 608. The circuitous flow path may allow a new gas entering pressure vessel 600 to efficiently purge or deplete an old gas that preexists in the pressure vessel. The circuitous flow path may also allow the pressure in one or more regions of pressure vessel 600 to reach a steady state in a period that is less than the time needed to allow the pressure in the entire pressure vessel to reach a steady state.

In some embodiments, first region 606 is fluidly connected to gas inlet 612 and gas outlet 614. For example, gas inlet 612 may be fluidly connected to a first opening or port disposed in first region 606. Gas outlet 614 may be fluidly connected to a second opening or port disposed in first region 606. A gas may flow from gas inlet 612 to gas outlet 614 via at least a portion of first region 606.

First region 606 may be configured to allow a gas entering gas inlet 612 to quickly fill at least one portion of first region 606. In some embodiments, first region 606 is divided to a plurality of chambers defining a first flow path 618. For example, one or more panels 616 may be disposed in and divide first region 606 into a plurality of chambers. First flow path 618 may be a circuitous flow path, such as a serpentine flow path. The circuitous flow path may allow a new gas entering first region 606 to quickly purge or deplete an old gas that preexists in one or more chambers of first region 606. This may allow the pressure in the one or more chambers of first region 606 to reach a steady state in a period that is less than the time needed to allow the pressure in the one or more chambers in first region 606 and second region 608 to reach a steady state. For example, it may take less than about 5 minutes for one or more chambers of first region 606 to reach a steady state pressure but it may take about 20 to about 30 minutes for the interior cavity of body 602 of pressure vessel 600 to reach a steady state pressure.

For example, as shown in FIGS. 6B and 6C, gas inlet 612 and gas outlet 614 may be fluidly connected to a first chamber 606a. The product gas may flow from gas inlet 612 to gas outlet 614 via at least a portion of first chamber 606a. The product gas received by gas inlet 612 may enter and quickly fill first chamber 606a of first region 606, allowing the pressure in first chamber 606a to reach a steady state over a short period. This may reduce a pressure-holding period before releasing the product gas from gas outlet 614.

First chamber 606a may have any suitable shape and/or dimensions that allow the pressure of the product gas in that chamber to reach a steady state within a short pressure-holding period. For example, first chamber 606a may have an elongated shape extending along a longitudinal dimension of body 602 and a narrow cross-section. First chamber 606a may have any suitable dimensions or volume. For example, first chamber 606a may have a volume that is 50% or less of the interior cavity of body 602. For example, a pressure vessel 600 may have an internal volume of about 800 mL and a first chamber 606a may have a volume of about 10 mL to about 200 mL. In one example, after receiving and holding a product gas for a pressure-holding period of about 20 minutes, the pressure vessel 600 can release the product gas at gas outlet 614 and the NO concentration in the released product gas can reach a steady state within about 10 minutes.

In some embodiments, second region 608 is fluidly connected to first region 606 via a channel 610. Second region 608 may receive and store gas flowing from first region 606. Second region 608 may include a circuitous flow path, such as a serpentine flow path. For example, second region 608 may be configured to allow gas from first region 606 to fill at least one portion of second region 608.

In some embodiments, second region 608 is divided to a plurality of chambers defining a second flow path 620. For example, one or more panels 616 may be disposed in and divide second region 616 into a plurality of chambers. Second flow path 620 may be in fluid communication with first flow path 618, for example, via channel 610. Second flow path 620 and first flow path 618 may form one continuous flow path. Second flow path 620 may be a circuitous flow path, such as a serpentine flow path. The circuitous flow path may allow a new gas entering second region 608 from first region 606 to purge or deplete an old gas that preexists in one or more chambers of second region 608. This may also allow pressure in the one or more chambers of second region 608 to reach a steady state before the pressure in the entire second region 608 reaches a steady state.

A chamber of second region 608 may be referred to as a gas storage unit. One or more of the plurality of chambers of second region 608 may be further divided into one or more subchambers to further reduce the volume in each gas storage unit. This may reduce or eliminate uneven mixing of a new gas with the old gas in second region 608, and may reduce the time needed for the pressure in second region 608 to reach steady state. For example, a chamber of second region 608 may each be divided to two or more fluidly connected subchambers by one or more dividers 609. Divider 609 may have any suitable structure for directing gas flow in a chamber, such as a panel or a board. For example, as shown in FIGS. 6B and 6C, two or more dividers 609 may each extend along at least a portion of the longitudinal axis of pressure vessel 600 and may be radially spaced apart such that the subchambers are fluidly connected via spaces 611 between the dividers.

As described herein, fluidically connected chambers in first region 606 or second region 608 may have any suitable configuration to define a flow path that allows a new gas to purge or deplete an old gas that preexists in one or more chambers of the region. For example, as shown in FIG. 6C, an inlet and an outlet of a chamber, such as first chamber 606a, may be disposed apart along at least one dimension, such as a horizontal and/or longitudinal dimension. Such configuration may allow the new gas entering the chamber to flow from the inlet, across the chamber along at least one dimension, to the outlet to purge or deplete the old gas that preexists in the chamber.

Second region 608 may serve as a repository for storing the product gas. For example, when a flow rate of the product gas received at gas inlet 612 is higher than a flow rate of the product gas released at gas outlet 614, extra product gas may flow from first region 606 to second region 608 to be stored. When the flow rate of the product gas received at gas inlet 612 is lower than the flow rate of the product gas released at gas outlet 614, the product gas stored in second region 608 may flow from second region 608 to first region 606 to supplement the product gas flow. In such instances, pressure vessel 600 may reduce variation in the pressure, flow rate, and/or NO concentration of the product gas released at gas outlet 614. This may be beneficial for providing a steady supply of NO, such as in situations where NO generation may vary due to various conditions. It may also be beneficial for providing a supply of NO at a desired pressure, flow rate, and/or concentration on demand. Second region 608 may also serve as a back-up source of NO. For example, in response to abnormality in NO generation by NO generation apparatus 100 and/or in the transportation of NO in system 10, the product gas stored in second region 608 may be released to continue or supplement the supply of NO.

In some embodiments, pressure vessel 600 includes a pressure relief valve 622. Pressure relief valve 622 is configured to control the pressure in pressure vessel 600 not to exceed a threshold. The threshold may be a predetermined safety threshold. Pressure relief valve 622 may be normally closed, for example, by a force of a spring. Pressure relief valve 622 may open when the pressure in one or more regions in pressure vessel 600 exceeds a threshold. In some embodiments, pressure relief valve 622 is in fluid communication with second region 608. As shown in FIG. 1, the product gas released from pressure relief valve 622 may be transported from pressure vessel 600 to waste gas treatment device 700.

In some embodiments, system 10 includes one or more pressure sensors to measure the pressure in one or more regions or chambers in pressure vessel 600. In some embodiments, a pressure sensor 624 may be configured to measure pressure in first region 606, such as in first chamber 606a of first region 606. The measurement of pressure sensor 624 may indicate the pressure of the product gas released from gas outlet 614 to downstream systems or devices. In some embodiments, one or more pressure sensors (not shown) may be configured to measure pressure in second region 608. The measurement of such pressure sensor may indicate the amount of product gas stored in second region 608.

In some embodiments, pressure vessel 600 includes a purge valve 626. Purge valve 626 may be used to purge or deplete gas, such as the product gas, in one or more regions in the interior cavity of pressure vessel 600. For example, purge valve 626 may be in fluid communication with first region 606 or second region 608. As shown in FIG. 1, the product gas released from purge valve 626 may be transported from pressure vessel 600 to waste gas treatment device 700. In some embodiments, as shown in FIG. 1, an NO sensor 628 is disposed downstream of purge valve 626 and configured to measure NO concentration of the product gas released from purge valve 626. Measurement of NO sensor 628 may indicate whether the product gas has been purged or depleted from one or more regions of pressure vessel 600.

In some embodiments, as shown in FIG. 1, system 10 includes one or more flow control devices 630 to control the flow rate of the product gas released from pressure vessel 600. Flow control device 630 may be disposed downstream of and in fluid communication with gas outlet 614. Flow control device 630 may include a flow meter and/or a flow controller, such as a flow control valve. In some embodiments, system 10 includes a first flow control device 630 and a second flow control device 630. First flow control device 630 may be selected to measure and/or adjust the flow rate in a first range and second flow control device 630 may be selected to measure and/or adjust the flow rate in a second range lower than the first range. Flow control device 630 may be in communication with and/or controlled by one or more other components of system 10, such as ventilation circuit 900, as described below.

Waste Gas Treatment

System 10 may generate waste gas before, during, and/or after NO generation and/or transportation. For example, waste gas may be generated during the separation of NO from reaction medium 112 by liquid-gas separation device 408. Also, for example, waste gas may be generated from releasing the product gas from pressure relief valve 622 of pressure vessel 600. Waste gas of system 10 may include one or more components, such as NO, the carrier gas, moisture, and other nitrogen oxides that may be generated during NO generation and/or transportation. For example, NO may be oxidized to nitrogen dioxide ($NO_2$) during NO generation or transportation in system 10.

Nitrogen oxides (also referred to as $NO_x$), such as NO and $NO_2$, may contribute to air pollution and/or pose health risks if directly released from system 10 to the ambient. In some embodiments, as shown in FIG. 1, system 10 includes one or more waste gas treatment device 700 to treat the waste gas before the waste gas is released from system 10. Waste gas treatment device 700 may reduce or remove one or more nitrogen oxides in the waste gas, thereby reducing or eliminating potential air pollution and/or risk of exposure to nitrogen oxides.

In some embodiments, waste gas treatment device 700 is disposed downstream of and in fluid communication with liquid-gas separation device 408. Waste gas treatment device 700 may receive a mixed gas from outlet 426 of liquid-gas separation device 408. The mixed gas may include the sweep gas and one or more nitrogen oxides, such as NO and $NO_2$. In some embodiments, waste gas treatment device 700 is disposed downstream of pressure vessel 600 and in fluid communication with pressure relief valve 622. Waste gas treatment device 700 may receive the product gas released from pressure relief valve 622 when the pressure in pressure vessel 600 reaches or exceeds a threshold. The product gas may include the carrier gas and one or more nitrogen oxides, such as NO and $NO_2$.

In some embodiments, waste gas from both pressure vessel 600 and liquid-gas separation device 408 may be treated by the same waste gas treatment device 700. For example, system 10 may include a three-way connector 702 disposed upstream of a waste gas treatment device 700 and downstream of both pressure vessel 600 and liquid-gas separation device 408. Waste gas from both pressure vessel 600 and liquid-gas separation device 408 may combine at three-way connector 702 and flow to the same waste gas treatment device 700. Three-way connector 702 may include any suitable structure, such as a three-way fitting or a three-way valve.

In some embodiments, waste gas treatment device 700 reduces or removes one or more nitrogen oxides in the waste gas as the waste gas passes through waste gas treatment device 700. In some embodiments, waste gas treatment device 700 includes a body, an inlet, and an outlet. The inlet and outlet are in fluid communication with a cavity defined by the body. In some embodiments, at least a portion of the cavity is filled with a filter material that may reduce or remove one or more nitrogen oxides as the waste gas passes through the filter material. The filter material may, for example, include one or more absorbing materials configured to absorb one or more nitrogen oxides $NO_x$, such as NO and $NO_2$.

In some embodiments, an absorbing material includes a base material prepared with an absorbing agent that may react with one or more nitrogen oxides. For example, the base material may be coated with an oxidizing agent. The base material may have any suitable configuration for providing a surface area for the absorbing agent to react with one or more nitrogen oxides. The base material may include, for example, one or more selected from a molecular sieve, silica gel, aluminum oxide, sponge, cotton, foam resin, silicon dioxide, and active charcoal. The absorbing agent may include, for example, one or more selected from permanganate, persulfate, chromate, and dichromate salts.

In some embodiments, waste gas treatment device 700 includes a plurality of baffles configured to define a flow path. In some embodiments, at least a portion of the flow path is filled with the filter material. The flow path may be a circuitous flow path, such as a serpentine flow path. For example, a plurality of baffles may extend from walls of the cavity in a staggered fashion to define a serpentine flow path. The circuitous flow path may extend along one or more dimensions. The circuitous flow path may increase the contact between the waste gas and the filter material to allow more nitrogen oxides to be reduced or removed as the waste gas passes through the device.

Figure 7A:
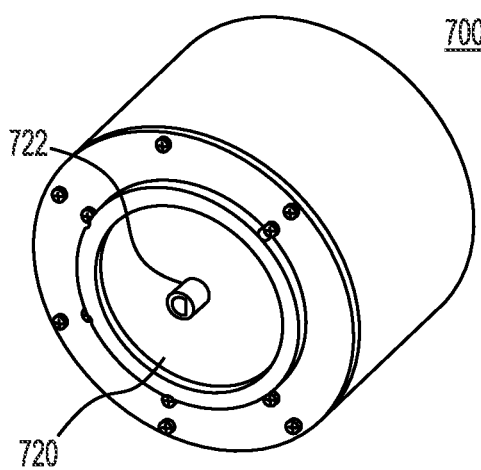
FIG. 7A is a top perspective view of a waste gas treatment device, according to some embodiments of the present disclosure.
Figure 7B:
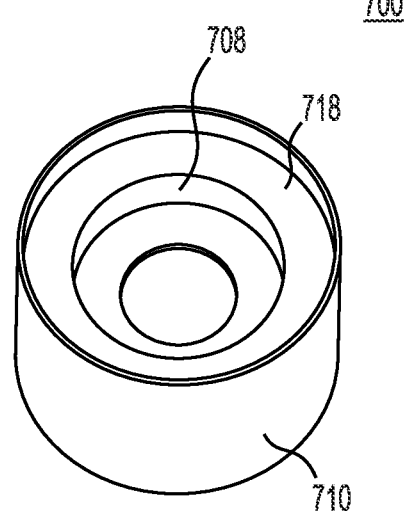
FIG. 7B is a bottom perspective view of the waste gas treatment device of FIG. 7A.
Figure 7C:
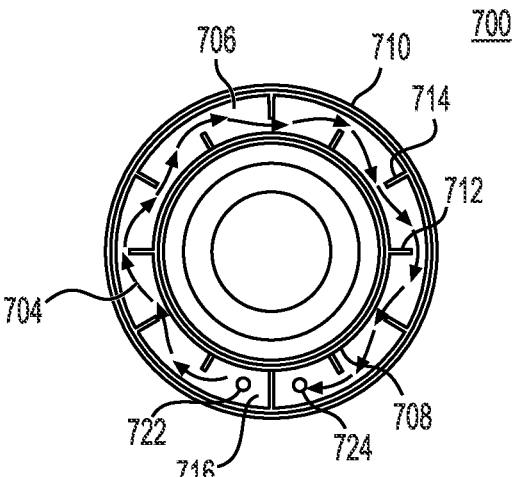
FIG. 7C is a cross-sectional view of the waste gas treatment device of FIG. 7A.

FIGS. 7A-7C are various views of a waste gas treatment device 700, according to some embodiments of the present disclosure. As shown in FIGS. 7A-7C, in some embodiments, waste gas treatment device 700 includes a body 703, an inlet 722, and an outlet 724. Inlet 722 and outlet 724 are in fluid communication with a cavity 706 defined by body 703. Body 703 may have any suitable shape, configuration, and/or dimension. For example, body 703 may have a cylindrical shape.

In some embodiments, body 703 has a first side 718 and a second side 720. Inlet 722 and outlet 724 may be disposed on opposites sides or on the same side of body 703. For example, inlet 722 may be disposed on first side 718 and outlet 724 may be disposed on second side 720. Alternatively, inlet 722 and outlet 724 may both be disposed on first side 718 or second side 720. In some embodiments, body 703 includes an inner shell 708 and an outer shell 710 extending from first side 718 to second side 720. Inner shell 708 and outer shell 710 may define an annular cavity 706. Inner shell 708 and outer shell 710 may have any suitable dimensions. For example, the diameter of the outer shell 710 may range from 120 mm to 160 mm, and the diameter of inner shell 708 may range from 80 mm to 120 mm.

In some embodiments, as shown in FIG. 7C, cavity 706 is divided by a wall 716 extending between inner shell 708 and outer shell 710 and extending from first side 718 to second side 720. Inlet 722 and outlet 724 may be disposed adjacent opposite sides of wall 716. At least a portion of cavity 706 may be filled with a filter material (not shown). Waste gas passing through waste gas treatment device 700 may flow from inlet 722, through cavity 706, to outlet 724.

In some embodiments, waste gas treatment device 700 includes a plurality of baffles. The plurality of baffles may have any configuration to define a circuitous flow path 704 in cavity 706, such as a serpentine flow path. In some embodiments, as shown in FIG. 7C, a first set of baffles 712 may extend between first side 718 and second side 720 and from inner shell 708 towards outer shell 710, and a second set of baffles 714 may extend between first side 718 and second side 720 and extend from outer shell 710 towards inner shell 708. Baffles 712 and 714 may extend over any suitable distance between inner shell 708 and outer shell 710 to direct the flow of waste gas. For example, the distance between baffle 712 and outer shell 710 and/or the distance between baffle 714 and inner shell 708 may range from 2 mm to 8 mm.

In some embodiments, first set of baffles 712 and second set of baffles 714 may be disposed in a staggered manner. For example, as shown in FIG. 7C, first set of baffles 712 may be evenly distributed around the circumference of inner shell 708 and second set of baffles 714 may be evenly distributed around the circumference of outer shell 710 with an offset from first set of baffles 712. Waste gas treatment device 700 may include any suitable number of baffles, such as from 2 to 16 baffles. For example, the number of first set of baffles 712 and/or of second set of baffles 714 may range from 2 to 8. The number of first set of baffles 712 and second set of baffles 714 may or may not be the same. It is contemplated that waste gas treatment device 700 may include any suitable number of baffles, with or without a suitable filter material provided.

Waste gas may flow from inlet 722, through circuitous flow path 704, to outlet 724. Circuitous flow path 704 may be filled with a filter material. One or more nitrogen oxides in the waste gas may be absorbed as the waste gas passes through the filter material in flow path 704. Waste gas may exit waste gas treatment device 700 from outlet 724, and may be released to the ambient with or without further treatment.

Reduction and/or Removal of Toxic Nitrogen Oxides

NO may be oxidized to one or more toxic nitrogen oxides, such as $NO_2$, which may impose health risks if delivered with NO to a patient. In some embodiments, system 10 includes a gas converter 800. Gas converter 800 may convert some or all potential toxic nitrogen oxides, such as $NO_2$, that may be present in the product gas to NO as the product gas passes through it. Gas converter 800 may reduce the potential risk of exposure to toxic nitrogen oxides, and may improve NO yield by converting other nitrogen oxides in the product gas back to NO.

Figure 8A:
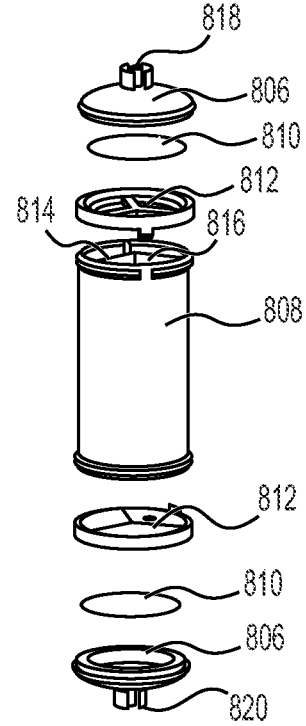
FIG. 8A is an exploded view of a gas converter, according to some embodiments of the present disclosure.

In some embodiments, gas converter 800 is disposed downstream of and in fluid communication with NO generation apparatus 100. In some embodiments, gas converter 800 is disposed downstream of and in fluid communication with filtration system 500. In some embodiments, gas converter 800 is disposed downstream of and in fluid communication with pressure vessel 600. FIG. 8A is an exploded view of a gas converter, according to some embodiments of the present disclosure. In some embodiments, as shown in FIG. 8A, gas converter 800 includes a body 808, an inlet 818, and an outlet 820. Inlet 818 and outlet 820 are in fluid communication with a cavity defined by body 808. Body 808 may have any suitable shape. In some embodiments, body 808 has a cylindrical shape extending between a first side and a second side. Two end covers 806 may cover the first and second sides of body 808. Inlet 818 and outlet 820 may be disposed at the same end cover 806 or at different end covers 806.

In some embodiments, gas converter 800 includes one or more membrane filters 810 and filter holders 812. Filter holders 812 may be configured to dispose a membrane filter 810 between an end cover 806 and body 808. Membrane filter 810 may reduce or remove one or more impurities in the product gas entering and/or exiting gas converter 800, such as moisture and solid matter.

In some embodiments, at least a portion of the cavity is filled with a filter material that may absorb one or more toxic nitrogen oxides, such as $NO_2$, as the product gas passes through the filter material. For example, the filter material may include soda lime particles. In some embodiments, at least a portion of the cavity is filled with a filter material that may convert one or more toxic nitrogen oxides, such as $NO_2$, to NO as the product gas passes through the filter material. In some embodiments, the filter material includes a base material configured to carry a reducing agent. For example, the surface of the base material may be prepared, such as applied, treated, or coated, with a reducing agent. The reducing agent may react with and reduce one or more nitrogen oxides to NO. The base material may have any suitable configuration for providing a surface area for carrying the reducing agent. The base material may include, for example, one or more selected from a molecular sieve, silica gel, aluminum oxide, sponge, cotton, foam resin. The reducing agent may include, for example, one or more antioxidants, such as vitamin A, vitamin E, and vitamin C. As used herein, vitamin C may also be referred to as ascorbic acid or ascorbate.

The filter material may be prepared using any suitable method or process. For example, an amount of one or more reducing agents may be prepared into a solution. The solution may be an aqueous solution or an organic solution, and may be a saturated solution of the one or more reducing agents. An amount of the base material may be added to the solution and mixed evenly. The base material may then be removed from the solution and dried under a drying temperature over a drying period to allow the solvent to evaporate. Any suitable amounts of reducing agents and base materials may be selected based on one or more conditions, such as the type of materials used and a desired reducing capacity. For example, an amount of reducing agents ranging from about 5 g to about 50 g may be used for preparing each amount of about 100 g of base material.

In one example, an amount of about 25 g vitamin C can be used for coating each amount of about 100 g aluminum oxide particles. In another example, an amount of about 5 g vitamin A can be used for preparing each amount of about 100 g cotton. In another example, an amount of about 5 g vitamin E can be used for preparing each amount of about 100 g foam resin. In another example, an amount of about 30 g vitamin C can be used for preparing each amount of about 100 g molecular sieve. In another example, an amount of about 20 g vitamin A can be used for preparing each amount of about 100 g sponge material. In another example, an amount of about 15 g vitamin E can be used for preparing each amount of about 100 g silica gel.

The drying temperature may range from about 40° C. to about 150° C., such as from about 40° C. to about 50° C., from about 50° C. to about 60° C., from about 60° C. to about 70° C., from about 70° C. to about 80° C., from about 80° C. to 90° C., from about 90° C. to about 100° C., from about 100° C. to about 110° C., from about 110° C. to about 120° C., from about 120° C. to about 130° C., from about 130° C. to about 140° C., from about 140° C. to about 150° C., or a combination thereof. The drying period may range from about 0.1 h to about 10 h, such as from about 0.1 h to about 0.2 h, from about 0.2 h to about 0.5 h, from about 0.5 h to about 1 h, from about 1 h to about 2 h, from about 2 h to about 3 h, from about 3 h to about 4 h, from about 4 h to about 5 h, from about 5 h to about 6 h, from about 6 h to about 7 h, from about 7 h to about 8 h, from about 8 h to about 9 h, from about 9 h to about 10 h, or a combination thereof.

Figure 8B:
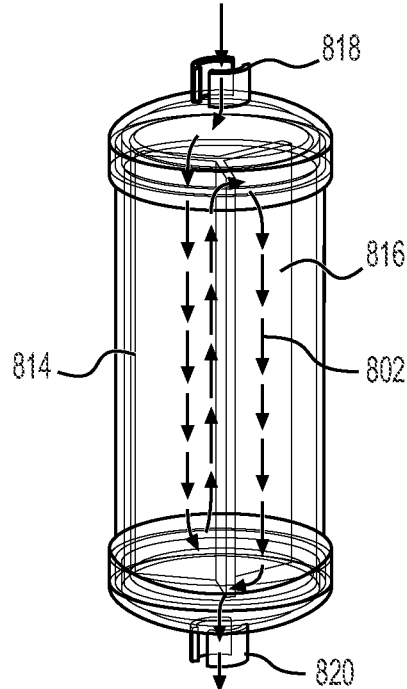
FIG. 8B is a schematic illustration of a gas converter, according to some embodiments of the present disclosure.

In some embodiments, as shown in FIGS. 8A-8B, the cavity of gas converter 800 is divided into a plurality of chambers 816, each having an inlet and an outlet. An inlet of a first chamber may be fluidly connected with inlet 818, and an outlet of the last chamber may be fluidly connected with outlet 820. The inlets and outlets of chambers 816 may be fluidly connected to define a flow path 802. A filter material may fill at least a portion of each chamber, such as from the inlet to the outlet of the chamber. The inlet and outlet of each chamber may be disposed at opposite ends such that a gas passing through the chamber may flow from the inlet, across the chamber through the filter material, to the outlet.

Flow path 802 may be a circuitous flow path, such as a serpentine flow path. A circuitous flow path in the cavity of body 808 may increase the contact between the product gas and the filter material to allow more nitrogen oxides to be reduced to NO as the product gas passes through the device under a given volume of the cavity.

The chambers in the cavity of gas converter 800 may have any suitable configurations. For example, one or more panels 814 may be disposed in and extend between the two sides of body 808. Panels 814 may be arranged around, equally or unequally spaced, the longitudinal axis of body 808. Panels 814 may each radially extend from the longitudinal axis to an inner wall of body 808. For example, panels 814 may evenly divide the cavity into a plurality of elongated chambers 816 extending between the two sides of body 808 and arranged around a longitudinal axis of body 808. Any suitable number of panels 814 may be used. For example, if panels 814 are arranged around the longitudinal axis of body 808, an odd number of panels 814 may divide the cavity into an odd number of chambers, and inlet 818 and outlet 820 may be disposed at opposite end covers 806. Alternatively, an even number of panels 814 may divide the cavity into an even number of chambers, and inlet 818 and outlet 820 may be disposed at the same end cover 806.

In one example, the cavity of a gas converter 800 can be evenly divided into three elongated chambers as shown in FIGS. 8A-8B. Each of the chambers can be filled with a filter material. For example, a filter material can be prepared with aluminum silica gel particles having an average dimeter of about 0.2 mm and vitamin C. First, about 5 grams of vitamin C can be dissolved in 100 grams of water to prepare a saturated aqueous solution of vitamin C. An amount of 100 grams of aluminum silica gel particles can be added to and mixed evenly in the solution. The aluminum silica gel particles can be dried under about 100° C. for about 0.5 hours. This gas converter 800 can be used to treat a gas flow containing 100 ppm $NO_2$ at a flow rate of 1.0 L/min for a continuous period of about 90 hours. About 100% of the $NO_2$ in the gas flow can be converted to NO.

Alternatively, the filter material can be prepared with silica gel particles having an average diameter of about 3 mm and vitamin E. First, about 15 grams of vitamin E can be prepared into a saturated solution. About 100 grams of silica gel particles can be added to and mixed evenly in the solution. The silica gel particles can be dried under about 50° C. for about 5 hours. This gas converter 800 can be used to treat a gas flow containing 500 ppm $NO_2$ at a flow rate of 4.0 L/min for a continuous period of about 5 hours. About 100% of the $NO_2$ in the gas flow can be converted to NO.

In another example, the cavity of a gas converter 800 can be evenly divided into four elongated chambers similar to the embodiments as shown in FIGS. 8A-8B. Each of the chambers can be filled with a filter material. The filter material can be prepared with molecular sieve particles having an average diameter of about 5 mm and vitamin A. First, about 25 grams of vitamin A can be prepared into a saturated solution. About 100 grams of molecular sieve particles can be added to and mixed evenly in the solution. The molecular sieve particles can be dried under about 80° C. for about 2 hours. This gas converter 800 can be used to treat a gas flow containing 200 ppm $NO_2$ at a flow rate of 2.0 L/min for a continuous period of about 70 hours. About 100% of the $NO_2$ in the gas flow can be converted to NO. Alternatively, filter material can be prepared with aluminum oxide particles having an average diameter of about 6 mm and vitamin C. About 35 grams of vitamin C can be prepared into a saturated solution. The aluminum oxide particles can be added to and mixed evenly in the solution. The aluminum oxide particles can be dried under about 120° C. for about 0.25 hours. This gas converter 800 can be used to treat a gas flow containing 500 ppm $NO_2$ at a flow rate of 1.0 L/min for a continuous period of about 125 hours. About 100% of the $NO_2$ in the gas flow can be converted to NO.

In another example, the cavity of a gas converter 800 can be evenly divided into five elongated chambers similar to the embodiments as shown in FIGS. 8A-8B. Each of the chambers can be filled with a filter material. The filter material can be prepared with sponge and vitamin E. About 40 grams of vitamin E can be prepared into a saturated solution. About 100 grams of sponge can be submerged in the solution. The sponge can be dried under about 150° C. for about 0.2 hours. This gas converter 800 can be used to treat a gas flow containing 800 ppm $NO_2$ at a flow rate of 3.0 L/min for a continuous period of about 12 hours. About 100% of the $NO_2$ in the gas flow can be converted to NO. Alternatively, the filter material can be prepared with cotton and vitamin A. About 50 grams of vitamin A can be prepared into a saturated solution. About 100 grams of cotton can be submerged in the solution. The cotton can be dried under about 70° C. for about 3 hours. This gas converter 800 can be used to treat a gas flow containing 400 ppm $NO_2$ at a flow rate of 4.0 L/min for a continuous period of 35 hours. About 100% of the $NO_2$ in the gas flow can be converted to NO.

In some embodiments, the product gas released from gas converter 800 may be an output gas of system 10. The quality and/or flow rate of the output gas of system may be monitored. For example, concentrations of NO, $NO_2$, and moisture may be monitored. In some embodiments, a flow rate meter is utilized to monitor the flow rate of the output gas of system 10.

NO Delivery and/or Monitoring

NO generated by system 10 may be used for various NO-based therapies. For example, NO generated by system 10 may be used for NO inhalation therapies. NO generated by system 10 may be delivered to a patient with or without another gas, such as oxygen. For example, NO generated by system 10 may be delivered to a patient with an air flow or an oxygen flow provided by a ventilator.

In some embodiments, as shown in FIG. 1, system 10 includes a ventilation circuit 900 for delivering inhaled NO to a patient. In some embodiments, ventilation circuit 900 is disposed downstream of and in fluid communication with pressure vessel 600. Ventilation circuit 900 may also be disposed downstream of and in fluid communication with gas converter 800. Ventilation circuit 900 may be configured to connect system 10 to a respiratory device or system to deliver NO in any suitable form. For example, ventilation circuit 900 may connect system 10 to a ventilator, a nebulizer, a positive airway pressure machine, an oxygen supply, or the like.

Figure 9:
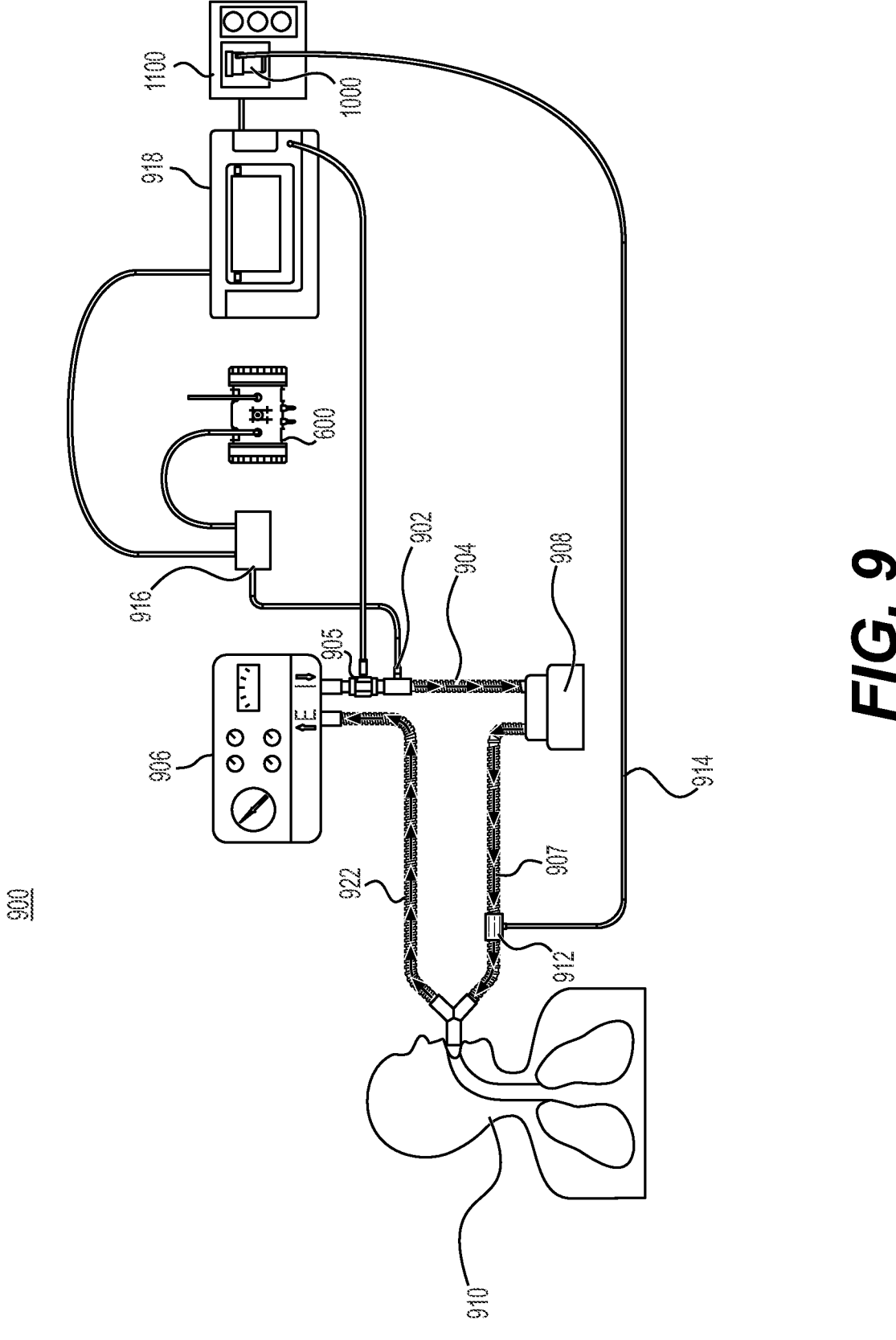
FIG. 9 is a schematic representation of a ventilation circuit for delivering NO to a patient, according to some embodiments of the present disclosure.

FIG. 9 is a schematic representation of a ventilation circuit 900 of system 10, according to some embodiments of the present disclosure. In some embodiments, ventilation circuit 900 includes an inspiratory circuit 904 and an expiratory circuit 922. Inspiratory circuit 904 may be configured to fluidly connect a ventilator 906 and deliver a gas flow, such as an air flow or an oxygen flow, from ventilator 906 to a patient 910 via a mask or tube. Expiratory circuit 922 may convey exhaled gas from patient 910 to ventilator 906.

In some embodiments, as shown in FIG. 9, ventilation circuit 900 includes a port 902 configured to receive a supply of NO. For example, port 902 may be disposed along and in fluid communication with inspiratory circuit 904. In some embodiments, port 902 is disposed downstream of and in fluid communication pressure vessel 600 and/or gas converter 800. NO supplied from pressure vessel 600 may be mixed with and/or entrained by oxygen or air flowing through inspiratory circuit 904 to form a gas mixture 907 to deliver to a patient 910. In some embodiments, a humidifier 908 is disposed downstream of port 902, and gas mixture 907 may be moisturized by humidifier 908 before being delivered to patient 910.

In some embodiments, ventilation circuit 900 includes a flow controller 916. Flow controller 916 may be disposed upstream of port 902 and configured to control the flow rate of a gas flow entering port 902, such as a product gas containing NO from pressure vessel 600 or gas converter

800. Flow controller 916 may include an inlet port, and outlet port, a flow sensor, and a control valve. In some embodiments, flow controller 916 is a mass flow controller.

In some embodiments, ventilation circuit 900 includes a control device 918. Control device 918 may be in communication with flow controller 916 via a wired or wireless connection. Control device 918 may send control signals to flow controller 916 to adjust the flow rate of the gas flow entering port 902. For example, control device 918 may receive sensor signals from flow controller 916 indicating the flow rate of a product gas entering port 902, and may generate control signals in response to the received sensor signals. The control signals may be sent from control device 918 to flow controller 916 to adjust the flow rate of the gas flow entering port 902.

In some embodiments, ventilation circuit 900 includes a flow rate sensor 905 configured to measure a flow rate of an air flow or an oxygen flow output from ventilator 906. Flow rate sensor 905 may be disposed along inhalation circuit 904, such as upstream of port 902. Control device 918 may be in communication with flow rate sensor 905 via a wired or wireless connection. Control device 918 may send control signals to flow controller 916 to adjust the flow rate of the gas flow entering port 902 based on sensor signals from flow rate sensor 905. For example, control device 918 may receive sensor signals from flow rate sensor 905 indicating the flow rate of an oxygen flow output by ventilator 906, and may generate control signals in response to the received sensor signals. The control signals may be sent to flow controller 916 to adjust the flow rate of a product gas entering port 902 to be mixed with the oxygen flow, allowing for the adjustment of concentration of NO in the mixed gas to be delivered to patient 910.

In some embodiments, ventilation circuit 900 includes one or more gas sensors. The gas sensors may be any suitable sensors configured to detect one or more types of gases, and may measure the concentrations of one or more components in gas mixture 907, such as NO, $NO_2$, $O_2$, and moisture. For example, the gas sensors may be electrochemical gas sensors, infrared gas sensors, or thermal conductivity gas sensors, In some embodiments, ventilation circuit 900 includes a sampling port 912. Sampling port 912 may be disposed along and in fluid communication with inspiratory circuit 904, such as downstream of humidifier 908. Sampling port 912 may be disposed upstream of an applicator, such as a mask or an endotracheal tube. Sampled gas or a sample gas flow from sampling port 912 may be used for measuring the concentrations of various components of gas mixture 907.

In some embodiments, one or more gas sensors may be disposed adjacent sampling port 912 and may be in communication with control device 918 with via a wired or wireless connection. In some embodiments, the one or more gas sensors are disposed in a gas monitoring device 1100. A sample gas flow may flow from sampling port 912, though a sampling circuit 914, to gas monitoring device 1100. Gas monitoring device 1100 may be in communication with control device 918 with via a wired or wireless connection. Sensor signals indicating the concentrations of one or more components, such as NO, $NO_2$ and $O_2$, may be sent from the gas sensors or from gas monitoring device 1100 to control device 918. Control device 918 may generate control signals in response to the received sensor signals, and may send the control signals to one or more components of system to adjust the concentrations of one or more components of gas mixture 907. For example, control device 918 may send control signals to energy source 114 to adjust NO concentration, or to flow controller 916 to adjust the concentrations of NO, $NO_2$, and $O_2$ in gas mixture 907.

Gas monitoring device 1100 may include various features. For example, gas monitoring device 1100 may include an alarm device configured to provide one or more alarms, such as an audible alarm or a visible alarm, when one or more measured gas concentrations of gas mixture 907 exceed a predetermined threshold, such as 25 ppm for NO and 5 ppm for $NO_2$. Gas monitoring device 1100 may include a display to display an alarm and/or measured concentration values. Because gas mixture 907 may pass through humidifier 908, a sample gas flow from port 912 may have a high humidity. Reducing or removing moisture in a sample gas flow of gas mixture 907 may improve the accuracy of one or more gas sensors of gas monitoring device 1100.

In some embodiments, gas monitoring device 1100 includes a moisture collector 1000 configured to reduce or remove moisture in a sample gas flow of gas mixture 907. FIG. 10A is a perspective view of a moisture collector 1000, according to some embodiments of the present disclosure. FIG. 10B is a partial perspective view of moisture collector 1000. FIG. 10C is another partial perspective view of moisture collector 1000. As shown in FIGS. 10A-10C, in some embodiments, moisture collector 1000 includes one or more inlets, such as inlet 1008, and one or more outlets, such as first outlet 1010 and second outlet 1012. A gas flow 1009, such as a sample gas flow from port 912, may enter moisture collector 1000 via one or more inlets and may exit moisture collector 1000 via one or more outlets. For example, as shown in FIG. 10A, gas flow 1009 may enter moisture collector 1000 via inlet 1008 and may split into a first gas flow 1014 and a second gas flow 1016 that exit moisture collector 1000 via first outlet 1010 and second outlet 1012 respectively.

In some embodiments, moisture collector 1000 includes a cup 1002, a cover 1004, and a moisture filter 1006. In some embodiments, moisture filter 1006 is disposed between cup 1002 and cover 1004. Gas flow 1009 may flow from inlet 1008, through moisture filter 1006, and out of outlet 1010 and/or outlet 1012. Moisture filter 1006 may be permeable to gas and impermeable to moisture, such as water droplets or water vapor. For example, moisture filter 1006 may include a material having pores configured to allow gas molecules to pass through but not larger particles, such as water molecules or solid particles. In some embodiments, moisture filter 1006 includes a porous membrane. In some embodiments, the porous membrane is a gas permeable membrane. In some embodiments, the porous membrane is a hydrophobic membrane.

In some embodiments, moisture collector 1000 includes one or more flow paths configured to allow a gas flow to pass through from the inlet to the outlet. In some embodiments, moisture collector 1000 includes a first chamber 1018 and a second chamber 1020 defining a flow path. First chamber 1018 may be disposed downstream of and in fluid communication with inlet 1008. Second chamber 1020 may be disposed downstream of and in fluid communication with first chamber 1018 and disposed upstream of and in fluid communication outlet 1010. Moisture filter 1006 may be disposed between first chamber 1018 and second chamber 1020. A gas flow 1009 may flow from first chamber 1018, through moisture filter 1006, to second chamber 1020, and may become a first gas flow 1014 having a moisture level lower than gas flow 1009.

Moisture blocked by moisture filter 1006 may accumulate, for example, in first chamber 1018 and on moisture filter 1006. The accumulated moisture may form liquid droplets. The liquid droplets may accumulate on a side of moisture filter 1006 facing gas flow 1009 or first chamber 1018, may be collected in first chamber 1018, and may flow through an opening 1022 of first chamber 1018 to cup 1002. Liquid accumulated on moisture filter 1006 may reduce the throughput of gas flow 1009 passing therethrough, such as accumulated on the side of moisture filter 1006 facing first chamber 1018. Such liquid accumulation may block the pores of a gas permeable membrane of moisture filter 1006 and reduce gas throughput of moisture collector 1000. In some embodiments, moisture filter 1006 is disposed at an inclined angle to facilitate liquid to accumulate towards an edge of moisture filter 1006 due to gravity.

In some embodiments, moisture collector 1000 includes one or more additional flow paths to increase the throughput of gas flow through moisture collector 1000. For example, moisture filter 1006 may include a third chamber 1024 and a fourth chamber 1026. Third chamber 1024 may be disposed in fluid communication with cup 1002, such as via an opening. Fourth chamber 1026 may be disposed downstream of and in fluid communication with third chamber 1024 and disposed upstream of and in fluid communication outlet 1012. Moisture filter 1006 may be disposed between third chamber 1024 and fourth chamber 1026. As shown in FIG. 10A, second gas flow 1016 may be directed towards cup 1002 by moisture filter 1006 and may flow from cup 1002 to third chamber 1024, through moisture filter 1006, to fourth chamber 1026. Second gas flow 1016 may exit moisture collector 1000 via outlet 1012. Second gas flow 1016 may sweep off liquid, such as water, accumulated on moisture filter 1006, thereby improving the throughput of gas flowing through moisture filter 1006.

In some embodiments, as shown in FIGS. 11A-11D, one or more outlets of moisture collector 1000 are in fluid communication with a gas sensing circuit of gas monitoring device 1100. For example, outlets 1010 and 1012 may be in fluid communication with the gas sensing circuit. One or more gas flows from moisture collector 1000 may be used for measuring gas concentrations by the gas sensing circuit. In some embodiments, first gas flow 1014 from moisture collector 1000 is used by the gas sensing circuit for measuring gas concentrations.

The gas sensing circuit of gas monitoring device 1100 may include various components and features for measuring gas concentrations and/or improving measurement accuracy. In some embodiments, gas monitoring device 1100 includes a sensing module 1102. Sensing module 1102 may include one or more gas sensors, such as an $NO_2$ sensor 1102a, an NO sensor 1102b, and an $O_2$ sensor 1102c. The one or more gas sensors may be disposed in one or more chambers configured to receive least a portion of a gas flow circulated in the gas sensing circuit, such as first gas flow 1014. For example, as shown in FIGS. 11A-11D, the gas sensors may be disposed in one chamber to measure gas concentrations of a gas flowing therethrough. Gas monitoring device 1100 may include a computer-readable storage device and/or a processor (not shown) in wired or wireless communication with the sensors to receive and process sensing signals received from the sensors. Gas monitoring device 1100 may include a transmitter circuit (not shown) in wired or wireless communication with a processor, a computer-readable storage device, and/or the gas sensors to transmit the sensing signals or readings to a controller, such as control device 918 or an electronic device (e.g., a tablet, a computer, or a smart phone). The readings of the gas sensors may be obtained by the gas sensors or the processor based on the sensing signals.

In some embodiments, the gas sensing circuit of gas monitoring device 1100 includes a pump 1104. Pump 1104 is configured to generate or drive one or more gas flows in the gas sensing circuit. In some embodiments, the gas sensing circuit includes one or more valves configured to direct one or more gas flows in the gas sensing circuit. For example, the gas sensing circuit may include at least one one-way valve 1106, such as a ball check valve. One-way valve 1106 may be disposed at any suitable place to prevent back flow. For example, pump 1104 may be disposed at a downstream location of the gas sensing circuit such that a gas flow from the pump outlet may be released to the ambient. A one-way valve 1106 may be disposed downstream of pump 1104 to prevent back flow of ambient air into the gas sensing circuit.

In some embodiments, gas monitoring device 1100 includes one or more switching valves configured to change the direction or flow path of a gas flow in the gas sensing circuit. For example, gas monitoring device 1100 may include a first switching valve 1110 and a second switching valve 1112. A switching valve may have one or more positions, such as a first position and a second position, for selecting a gas flow path or a flow direction in the gas sensing circuit. The positions of the switching valves may be selected, manually or automatically, using a user interface. A user interface may be, for example, a graphical user interface or a panel of controls, such as switches or buttons.

In some embodiments, the one or more switching valves may be disposed in a control module 1114. As shown in FIGS. 11A-111D, control module 1114 may include one or more connection ports, such as connection ports 1116A-1116G. A switching valve may fluidly connect one or more of the connection ports. Such configuration of may improve assemblability and/or serviceability of gas monitoring device 1100. For example, first switching valve 1110 may have a first position to fluidly connect connection ports 1116A and 1116C, and may have a second position to fluidly connect connection ports 1116A and 1116D. For example, second switching valve 1112 may have a first position to fluidly connect connection ports 1116E and 1116G, and may have a second position to fluidly connect connection ports 1116F and 1116G. In some embodiments, selected connection ports may be fluidly connected to form one or more flow paths. For example, connection ports 1116B and 1116C may be fluidly connected. Various uses of the switching valves in one or more operating processes of gas monitoring device 1100 are described further below.

In some embodiments, gas monitoring device 1100 includes one or more pressure sensors. In some embodiments, gas monitoring device 1100 includes at least one an absolute pressure sensor 1118. In some embodiments, gas monitoring device 1100 includes at least one differential pressure sensor 1120. A differential pressure sensor may be used to measure the flow rate of a gas flow in the gas sensing circuit. For example, a flow rate of a gas flow may be calculated based on a differential pressure measured by differential pressure sensor 1120 and Bernoulli's equation.

In some embodiments, the gas sensing circuit of gas monitoring device 1100 includes one or more flow regulators, such as a first flow regulator 1122 and a second flow regulator 1124. A flow regulator may be a flow control, a flow limiter, or a flow restrictor. A flow regulator may be configured to control the flow rate of the gas flow flowing therethrough. For example, a flow regulator may be configured to restrict the flow rate of gas flow of a flow path to a specific range or value. In some embodiments, first flow regulator 1122 is configured to regulate first gas flow 1014 from moisture collector 1000. In some embodiments, second flow regulator 1124 is configured to regulate second gas flow 1016 from moisture collector 1000. In some embodiments, differential pressure sensor 1120 is configured to measure a differential pressure across flow regulator 1122.

In some embodiments, gas monitoring device 1100 includes one or more filters. A filter may be disposed at any suitable position in the gas sensing circuit to reduce or remove one or more impurities in the gas flow, such as moisture and solid matter. Such filter may further reduce or remove moisture in the gas sensing module to improve the measurement accuracy of gas sensors. Additionally or alternatively, such filter may reduce or prevent solid matter from entering the valves and thus may improve the life of gas monitoring device 1100.

In some embodiments, a filter 1128 is disposed upstream of gas sensing module 1102. Filter 1128 may include a moisture filter configured to reduce or remove moisture, such as water, in the vapor phase and/or the liquid phase. Filter 1128 may include a membrane filter, such as a Nafion™ membrane filter. The gas sensing circuit of gas monitoring device 1100 may include one or more gas inlets, such as a first gas inlet 1127a and a second gas inlet 1127b, configured to receive an air flow from the ambient or a gas supply, such as a compressed air supply. A filter 1126 may be disposed downstream of a gas inlet to reduce or remove moisture and/or dust in the gas flow received by the gas inlet.

In some embodiments, the gas sensing circuit includes one or more $NO_x$ absorbers 1108. An $NO_x$ absorber 1108 may be configured to absorb one or more nitride oxides, such as $NO_2$ and NO. In some embodiments, an $NO_x$ absorber 1108 is disposed upstream of a gas inlet to remove or reduce one or more nitride oxides, such as $NO_2$ and NO, in an air flow entering the gas sensing circuit via a gas inlet. The gas sensing circuit may include one or more gas outlets, such as gas outlet 1129, configured to output a gas flow, such as second gas flow 1016 or first gas flow 1014, to the ambient. In some embodiments, an $NO_x$ absorber 1108 is disposed downstream of a gas outlet to remove or reduce one or more nitride oxides, such as $NO_2$ and NO, before the gas flow is released to the ambient.

$NO_x$ absorber 1108 may include one or more absorbing materials configured to absorb one or more nitrogen oxides $NO_x$, such as NO and $NO_2$. The absorbing materials in $NO_x$ absorber 1108 may be similar to the absorbing materials of waste gas treatment device 700. $NO_x$ absorber 1108 may have a similar structure as that of waste gas treatment device 700. For example, $NO_x$ absorber 1108 may include a circuitous flow path, at least a portion of which is filled with one or more absorbing materials.

Various components of gas monitoring device 1100 may be used in one or more operating processes, such as an initialization process, a calibration process, a sampling process, and a cleaning process. Such one or more operating processes may be automatically controlled by a processor and/or manually by a user via a user interface, such as a panel of controls or a graphical user interface. Embodiments of various processes performed by gas monitoring device 1100 are described below.

In some embodiments, gas monitoring device 1100 is configured to perform an initialization process. FIG. 11A is a schematic representation of an initialization process of a gas monitoring device 1000, according to some embodiments of the present disclosure. An initialization process may be performed to reduce or remove moisture in the gas sensing circuit and/or to purge preexisting gas out of the gas sensing circuit. For example, during an initialization process, ambient air may be introduced into and pass through at least a portion of the gas sensing circuit to dry and/or purge sensing module 1102 and/or one or more flow paths of the gas sensing circuit.

In some embodiments, as shown in FIG. 11A, during an initialization process, one or more switching valves may be switched to suitable positions to fluidly connect selected connection ports to direct one or more gas flows in the gas sensing circuit. For example, first switching valve 1110 may be switched to a second position to fluidly connect connection ports 1116A and 1116D. Second switching valve 1112 may be switched to its second position to fluidly connect connection ports 1116F and 1116G. As indicated by the arrows in FIG. 11A, during an initialization process, for example, pump 1104 may generate an air flow passing through the gas sensing circuit from gas inlet 1127a, through connection ports 1116D and 1116A, sensing module 1102, filter 1128, connection ports 1116G and 1116F, to outlet 1010. During an initialization process, the air flow may also flow through one or more of flow regulator 1122, filter 1126, flow regulator 1124, and one-way valve 1106. The air flow may flow through $NO_x$ absorber 1108 before exiting the sensing circuit via gas outlet 1129.

During an initialization process, as shown in FIG. 11A, pump 1104 may drive the air flow to outlet 1010, through cup 1002, outlet 1012, connection ports 1116B and 1116C, and to gas outlet 1129. The initialization process may be performed for any suitable duration, such as for less than about 1 minute, less than about 30 seconds, less than about 10 seconds, or less than about 1 second.

During an initialization process, it may be determined whether various components of gas monitoring device 1100 can operate in normal conditions. Additionally or alternatively, gas monitoring device 1100 may generate one or more alarms indicating one or more abnormal conditions of the gas sensing circuit. For example, the switching valves may be switched to different positions to determine whether the valves can operate in a normal condition. Pump 1104 may be set to a certain flow rate and a flow rate of a gas flow generated by pump 1104 may be measured to determine whether pump 1104 can operate in a normal condition. When there is no gas flow in the gas sensing circuit, a normal reading of absolute pressure sensor 1118 may not exceed a predetermined value, such as any value from about 600 mbar to about 1250 mbar, and a normal flow rate calculated based on the reading of differential pressure sensor 1120 may not exceed a flow rate range predetermined by the pump settings, such as from about 50 ml/min to about 1000 ml/min.

In some embodiments, gas monitoring device 1100 is configured to perform a calibration process to calibrate the one or more gas sensors in sensing module 1102. A calibration process may be performed regularly, such as periodically, on an as-needed basis, or prior to delivering gas mixture 907 to the patient. Air, such as ambient air or compressed air, or a standard gas with known concentrations of its gas components may be used to calibrate the sensors. FIG. 11B a schematic representation of a calibration process of a gas monitoring device 1100, according to some embodiments of the present disclosure. In some embodiments, as shown in FIG. 11B, ambient air is used in the calibration process. For example, first switching valve 1110 may be switched to its first position to fluidly connect connection ports 1116B and 1116C. Second switching valve 1112 may be switched to its first position to fluidly connect connection ports 1116E and 1116G. Pump 1104 may generate an air flow from gas inlet 1127b, through connection ports 1116E and 1116G, filter 1128, sensing module 1102, connection port 1116A, and connection port 1116C, to gas outlet 1129. An NO$_x$ absorber 1108 may be disposed downstream of gas inlet 1127$b$ to remove or reduce NO$_2$ and NO before the air flow passes through sensing module 1102. The air flow may also pass through one or more of a flow regulator 1122, a filter 1126, and a one-way valve 1106.

During a calibration process, pump 1114 may also drive gas flow 1016 from outlet 1012, through connection ports 1116B and 1116C, to gas outlet 1129. Gas flow 1016 may also flow through one or more of filter 1126, flow regulator 1124, one-way valve 1106, and NO$_x$ absorber 1108.

In some embodiments, the calibration process is performed to adjust a calibration curve of at least one sensor of sensing module 1102, such as adjusting the calibration curve with an offset value. The calibration process may include a zero calibration and/or a span calibration. For example, in a zero calibration, an air flow from the ambient after passing through NO$_x$ absorber 1108 may be predetermined to have about 21% O$_2$, about 0% or 0 ppm NO, and about 0% or 0 ppm NO$_2$. The sensors of sensing module may assume readings of the air flow correspond to these predetermined concentrations and may adjust their calibration curves with offset values.

In some embodiments, in a span calibration, one or more standard gases having known concentrations of O$_2$, NO, and/or NO$_2$ may be used in the calibration process. As shown in FIG. 11C, first switching valve 1110 may be switched to its first position to fluidly connect connection ports 1116A and 1116C. Second switching valve 1112 may be switched to its second position to fluidly connect connection ports 1116F and 1116G. Pump 1104 may drive a flow of a standard gas from outlet 1010, through connection port 1116F, connection port 1116G, filter 1128, sensing module 1102, connection port 1116A, and connection port 1116C, and to gas outlet 1129. The standard gas flow may also pass through one or more of a flow regulator 1122, a one-way valve 1106, and an NO$_x$ absorber 1108 before being released via gas outlet 1129. The sensors of sensing module may assume readings of the standard gas flow correspond to known concentrations of the standard gas and may adjust their calibration curves with offset values.

In some embodiments, gas monitoring device 1100 is configured to perform a sampling process to measure concentrations of one or more gas components of a sample gas flow. FIG. 11C is a schematic representation of a sampling process of a gas monitoring device 1100, according to some embodiments of the present disclosure. A sampling process may be performed on an as-needed basis or may be performed continuously or intermittently while delivering gas mixture 907 to patient 910. In some embodiments, in a sampling process, the gas sensing circuit may receive first gas flow 1014 from outlet 1010 of moisture collector 1000, and/or may receive second gas flow 1016 from outlet 1012 of moisture collector 1000. First flow regulator 1122 may regulate the flow rate of first gas flow 1014 to a first flow rate. Second flow regulator 1124 may regulate the flow rate of second gas flow 1016 to a second flow rate. The first and second flow rates may be predetermined and adjusted based on settings of pump 1104 and/or settings of flow regulators 1122 and 1124. The first flow rate and the second flow rate may add up to the flow rate of pump 1104. For example, a flow rate of pump 1104 may range from about 50 m/min to about 1000 mL/min, a first flow rate of first gas flow 1014 may range from about 40 mL/to about 800 mL/min, and a second flow rate of second gas flow 1016 may range from about 10 mL to about 200 mL/min.

In some embodiments, concentrations in first gas flow 1014 are measured in the sampling process. As shown in FIG. 11C, first switching valve 1110 may be switched to its first position to fluidly connect connection ports 1116A and 1116C. Second switching valve 1112 may be switched to its second position to fluidly connect connection ports 1116F and 1116G. Pump 1104 may drive first gas flow 1014 from outlet 1010, through connection port 1116F, connection port 1116G, filter 1128, sensing module 1102, connection port 1116A, and connection port 1116C, and to gas outlet 1129. First gas flow 1014 may also pass through one or more of a flow regulator 1122, a one-way valve 1106, and an NO$_x$ absorber 1108 before being released via gas outlet 1129. Pump 1104 may also drive second gas flow 1016 from outlet 1012, through connection port 1116B and connection port 1116C, to gas outlet 1129. Second gas flow 1016 may also pass through one or more of a flow regulator 1124, a one-way valve 1106, and NO$_x$ absorber 1108 before being released via gas outlet 1129.

In some embodiments, the one or more gas sensors of sensing module 1102 are configured to identify and measure concentrations of one or more gas components, such as NO$_2$, NO, and O$_2$, in first gas flow 1014 as it passes through gas sensing module 1102. Readings from these sensors may be transmitted to the processor and/or a computer-readable storage medium (not shown) of gas monitoring device 1100 by wired or wireless communication for further processing and/or transmitting to one or more other devices.

The accuracy of the one or more sensors in sensing module 1102 may be improved when first gas flow 1014 passes through the sensors at a predetermined flow rate or with in a predetermined flow rate range. In some embodiments, the flow rate of first gas flow 1014 is regulated by flow regulator 1122 and differential pressure sensor 1120 is used to measure the flow rate of first gas flow 1014 through flow regulator 1122. The predetermine flow rate or flow rate range may be any suitable value or range based on the type of sensors. For example, the one or more sensors may be electrochemical sensors and the predetermined flow rate range may be from about 50 ml/min to about 450 ml/min, such as from about 220 ml/min to about 240 ml/min. Pump 1104 may be used to adjust the flow rate of first gas flow 1014 passing through sensing module to the predetermined value or range.

In some embodiments, gas monitoring device 1100 is configured to perform a cleaning process to reduce or remove liquid accumulated on moisture filter 1006 of moisture collector 1000 and/or in the gas sensing circuit. FIG. 11D a schematic representation of a cleaning process of a gas monitoring device 1100, according to some embodiments of the present disclosure. As shown in FIG. 11D, first switching valve 1110 may be switched to its second position to disconnect connection ports 1116A and 1116C, thereby disconnecting first gas flow 1014. Second switching valve 1112 may be switched to its first position to fluidly connect connection ports 1116E and 1116G. Pump 1104 may drive second gas flow 1016 from outlet 1012, through connection port 1116B and connection port 1116C, and to gas outlet 1129. Second gas flow 1016 may also pass through one or more of a filter 1126, a flow regulator 1124, a one-way valve 1106, and an NO$_x$ absorber 1108 before being released via gas outlet 1129.

During the cleaning process, disconnecting first gas flow 1014 allows the flow rate of second gas flow 1016 to increase. As shown in FIG. 10A, before exiting outlet 1012, second gas flow 1016 may flow from first chamber 1018, to cup 1002, back to moisture filter 1006, such as the side of moisture filter 1006 facing gas flow 1009 or the side facing first chamber 1018 where liquid may accumulate. Increasing the flow rate of second gas flow 1016 may increase drying or sweeping off the liquid accumulated on moisture filter 1006.

Gas monitoring device 1100 may perform a cleaning process on an as-needed basis and/or when one or more abnormal conditions occur. The cleaning process may be performed for any suitable duration, such as for less than about 2 minutes, less than about 1 minute, less than about 30 seconds, less than about 10 seconds. A cleaning process may automatically start or be manually started. For example, a processor of gas monitoring device 1100 may start a cleaning process in response to one or more abnormal readings of absolute pressure sensor 1118 and/or of differential pressure sensor 1120 when liquid blocks at least a portion of moisture filter 1006 and/or a flow path in the gas sensing circuit. For example, during a sampling process, a normal absolute pressure measured by pressure sensor 1118 may be in a range from about 0.5 bar to about 1.25 bar. An absolute pressure outside this range may indicate that moisture filter 1006 and/or the gas sensing circuit are clogged by liquid. A normal flow rate calculated based on differential pressure measured by pressure sensor 1120 may range from about 20 ml/min to about 275 ml/min, such as from about 20 ml/min to about 50 ml/min, from about 50 ml/min to about 100 ml/min, from about 100 ml/min to about 150 ml/min, from about 150 ml/min to about 200 ml/min, from about 200 ml/min to about 250 ml/min, or from about 250 ml/min to about 275 ml/min. A flow rate lower than this range may indicate that moisture filter 1006 and/or the gas sensing circuit are clogged by liquid.

As described herein, system 10 may be modularized such that one or more of its components, such as reaction chamber 102, reaction medium 112, one or more of the electrodes (e.g., first electrode 116, second electrode 118), filtration system 500 or filters thereof, pressure vessel 600, waste gas treatment device 700, gas converter 800, and flow control devices, may be conveniently replaced, maintained, or serviced without substantially dissembling system 10. As such, maintenance cost of system 10 may be reduced, and operating life of system 10 may be extended.

In some embodiments, system 10 may include a user interface in communication with a control circuit. The user interface may include one or more controls for receiving instructions from a user to adjust system parameters, such as number of sessions, number of operating periods in each session, and a concentration and/or flow rate of NO in a session or an operating period. The control circuit may send control signals to various components to adjust these system parameters, such as energy source 114, carrier gas source 200, and flow controllers or control devices.

System 10 or one or more components thereof, such as NO generation apparatus 100, as described herein may be used in various methods for generating and/or delivering NO. For example, system 10 or NO generation apparatus 100 may be used to generate NO on-demand. In some embodiments, system 10 or NO generation apparatus 100 may be used to provide a steady supply of NO at a predetermined concentration within a ramp period. A ramp period may refer to a transient period during which NO concentration of the product gas may change from an initial concentration to a predetermined steady state concentration. For example, during a ramp period, NO concentration of the product gas increase from an initial concentration, such as zero, to a predetermined steady state concentration. System 10 or NO generation apparatus 100 may be used to provide a steady supply of NO over one or more sessions or over one or more operating periods. System 10 may be used to reduce or minimize potential air pollution and/or exposure to toxic gases, such as nitrogen dioxide, during the generation or delivery of NO. System 10 may be used to deliver NO with another treatment gas, such as oxygen or air, supplied by a respiratory device, such as a ventilator. System 10 may be used to monitor the concentration of one or more components of a gas mixture to be delivered to or inhaled by a patient.

As described herein, the steps of the disclosed methods may be modified in any manner, including by reordering steps, inserting, and/or deleting steps. One or more steps of the disclosed methods may be performed at the same time or in any suitable time sequence unless described otherwise.

FIG. 12 is a flow chart illustrating an NO generation method 1200, according to some embodiments of the present disclosure. In some embodiments, as shown in FIG. 12, method 1200 includes steps 1202-1210. In some embodiments, step 1202 includes applying, by an energy source, a voltage or a current to one or more of a plurality of electrodes disposed in a reaction medium to generate NO. The plurality of electrodes may include a cathode. In some embodiments, NO is generated at or adjacent one or more surfaces of the plurality of electrodes. The reaction medium may be contained in a reaction chamber of an NO generation apparatus. In some embodiments, the reaction chamber includes a gas region and a liquid region, and the reaction medium is disposed in the liquid region.

In some embodiments, in step 1202, the voltage or current applied to the plurality of electrodes may be predetermined and/or adjusted based on one or more conditions, such as a desired NO concentration in an output product gas. In some embodiments, the predetermined voltage ranges from about 1.4 V to about 5.0 V. In some embodiments, the predetermined current ranges from about 0 mA to about 300 mA. The rate of NO generation may increase with the increase of the voltage or current applied to the plurality of electrodes. In some cases, NO may be generated when a current of about 0 mA is applied to the plurality of electrodes. In some embodiments, step 1202 includes terminating the voltage or the current applied to the plurality of electrodes.

In some embodiments, step 1202 includes applying a stimulation voltage or a stimulation current to the plurality of electrodes for a stimulation period before applying the predetermined voltage or the predetermined current. The stimulation period may range from about 0.5 minutes to about 5 minutes, such as from about 0.5 minute to about 1 minute, from about 1 minute to about 2 minutes, from about 2 minutes to about 3 minutes, from about 3 minutes to about 4 minutes, from about 4 minutes to about 5 minutes, or a combination thereof. In some embodiments, the stimulation voltage is from about 2 to about 8 times of the predetermined voltage. In some embodiments, the stimulation current is from about 2 to about 8 times of the predetermined current.

In some embodiments, step 1202 includes switching the polarity of two electrodes, such as a cathode and an anode. For example, step 1202 may include reversing the polarity of the energy source, such as inverting the polarity of a DC power supply or by using an AC power supply. The polarity of the two electrodes may be switched on an as-needed basis or according to a predetermined schedule. For example, the polarity of the two electrodes may be switched periodically, such from about every 10 min to about every 10 hours.

In some embodiments, method 1200 includes step 1204. In some embodiments, step 1204 includes receiving, by an NO generation apparatus, a carrier gas through an inlet circuit of the NO generation apparatus. The inlet circuit may be in fluid communication with at least one sparger disposed in the reaction medium. The at least one sparger may be positioned adjacent one or more of the plurality of electrodes. In some embodiments, the carrier gas is received from a carrier gas source. In some embodiments, the carrier gas includes nitrogen. In some embodiments, step 1204 includes generating, by the carrier gas source, the carrier gas from compressed air. For example, the carrier gas may be generated from compressed air using a nitrogen generation apparatus.

In some embodiments, step 1204 includes controlling, by a flow control device, the flow rate of the carrier gas received through the inlet circuit. In some embodiments, step 1204 includes receiving the carrier gas at a flow rate ranging from about 50 mL/min to about 12 L/min, such as from about 0.5 L/min to about 1 L/min, from about 1 L/min to about 3 L/min, from about 3 L/min to about 5 L/min, from about 5 L/min to about 8 L/min, from about 8 L/min to about 10 L/min, from about 10 L/min to about 12 L/min, or a combination thereof.

In some embodiments, step 1204 includes purging system 10 using the carrier gas. For example, the carrier gas may be passed through some or all gas flow regions or paths of system, such as a gas region of reaction chamber, inlet and outlet circuits, circulation circuits, and a pressure vessel. Purging system 10 with the carrier gas may reduce the oxidation of generated NO to toxic nitrite oxides, such as $NO_2$, in the product gas. Purging system 10 may improve the life of a gas converter configured to reduce or remove $NO_2$.

In some embodiments, method 1200 includes step 1206. In some embodiments, step 1206 includes sweeping, using the carrier gas, a surface of one or more of the plurality of electrodes. Sweeping a surface of an electrode may sweep, purge, and/or entrain NO generated at or adjacent the surface of the electrode out of the reaction medium. This may generate a product gas that may include the generated NO and the carrier gas. In some embodiments, at least a portion of the product gas is received and/or accumulated in the gas region of the reaction chamber of the NO generation apparatus.

In some embodiments, step 1206 includes generating bubbles of the carrier gas to sweep a surface of one or more of the plurality of electrodes. For example, step 1206 may include receiving the carrier gas by a sparger, and may include emanating, by the sparger, bubbles of the carrier gas in the reaction medium to sweep a surface of one or more of the plurality of electrodes. The sparger may be in fluid communication with the inlet circuit and disposed in the reaction medium adjacent one or more of the plurality of electrodes. The bubbles emanated by the sparger may propagate along a bubble path that may extend along the surface of the least one electrode.

In some embodiments, method 1200 includes step 1208. In some embodiments, step 1208 includes circulating, using a first circulation circuit, a first fluid flow relative to the reaction chamber. In some embodiments, step 1208 includes creating, by a gas pump, the first fluid flow from an inlet to an outlet of the first circulation circuit. In some embodiments, the first fluid flow includes a flow of the product gas generated in step 1206. In some embodiments, step 1208 includes filtering the recirculated fluid flow using one or more filters disposed upstream of the gas pump. The one or more filters may reduce or remove liquid and/or solid matter in the recirculated fluid flow before it enters the gas pump.

In some embodiments, step 1208 may include circulating the first fluid flow at a flow rate from about 0.5 L/min to about 5.0 L/min, such as from about 0.5 L/min to about 1.0 L/min, from about 1.0 L/min to about 1.5 L/min, from about 1.5 L/min to about 2.0 L/min, from about 2.0 L/min to about 2.5 L/min, from about 2.5 L/min to about 3.0 L/min, from about 3.0 L/min to about 3.5 L/min, from about 3.5 L/min to about 4.0 L/min, from about 4.0 L/min to about 4.5 L/min, from about 4.5 L/min to about 5.0 L/min, or a combination thereof.

In some embodiments, method 1200 includes step 1210. In some embodiments, step 1210 includes conveying the product gas containing NO from the reaction chamber through an outlet circuit. In some embodiments, the outlet circuit is in fluid communication with the gas region of the reaction chamber. In some embodiments, NO concentration of the product gas conveyed from the reaction chamber may reach a steady state within a ramp period. The ramp period may range from about 2 to about 10 minutes, for example.

In some embodiments, method 1200 may include or more selected from steps 1212-1222 described below.

In some embodiments, method 1200 includes step 1212. In some embodiments, step 1212 includes measuring, using a NO concentration sensor, a concentration of NO in the product gas. In some embodiments, the NO concentration sensor may be disposed in contact with the product gas in the gas region to measure NO concentration in the gas region. In some embodiments, the NO concentration sensor may be disposed in, adjacent, or downstream of the outlet circuit of the reaction chamber to detect an NO concentration of the product gas exiting reaction chamber. For example, the NO sensor may be disposed at an opening of the outlet circuit, within a conduit of the outlet circuit, or downstream of a filter that is disposed downstream of the outlet circuit.

In some embodiments, method 1200 includes step 1214. Step 1214 may reduce or remove NO dissolved in the reaction medium after NO generation over a session or an operating period. Step 1214 may include separating at least some dissolved NO from the reaction medium. Step 1214 may further include treating the separated NO, such as using a waste gas treatment device.

In some embodiments, step 1214 includes circulating, using a second circulation circuit, a second fluid flow relative to the reaction chamber. In some embodiments, the second fluid flow in the second circulation circuit includes a liquid flow. In some embodiments, the second fluid flow in the second circulation circuit includes a gas flow. In some embodiments, step 1214 is performed before, during, and/or after the reaction medium is used for generating NO in step 1202. For example, step 1214 may be performed after terminating a voltage or current applied to the electrodes after generating NO over a session or an operating period. Step 1214 may be performed before starting to apply a voltage or a current to the electrodes to generate NO for the next session or operating period.

In some embodiments, step 1214 includes configuring and/or operating the second circulation circuit to operate in a working mode. In the working mode, the second fluid flow may include a flow of the reaction medium. In some embodiments, operating the second circulation circuit in the working mode includes circulating, using a pump, the second fluid flow from a first port of the second circulation circuit, through a liquid-gas separation device, and out of a second port of the second circulation circuit. The first port may be in fluid communication with the liquid region of the reaction chamber, and the second port may be in fluid communication with the gas region of the reaction chamber.

In the working mode, the second fluid flow may be circulated at any suitable flow rate, such as a flow rate ranging from about 0.1 L/min to about 0.5 L/min, from about 0.5 L/min to about 1.0 L/min, from about 1.0 L/min to about 3.0 L/min, from about 3.0 L/min to about 5.0 L/min, from 5.0 L/min to about 8.0 L/min, or a combination thereof. The second circulation circuit may be operated in the working mode for any suitable period, such as for less than about 0.5 minute, less than about 1 minute, less than about 2 minutes, less than about 5 minutes, less than about 10 minutes, or less than about 20 minutes.

In some embodiments, operating the second circulation circuit in the working mode includes separating NO from the reaction medium as the second fluid flow passes through the liquid-gas separation device. In some embodiments, operating the second circulation circuit in the working mode includes passing a sweep gas through the liquid-gas separation device to entrain NO separated from the second fluid flow out of the liquid-gas separation device as a mixed gas. In some embodiments, operating the second circulation circuit in the working mode includes transporting the mixed gas to a waste gas treatment device before releasing the mixed gas to the ambient.

In some embodiments, step 1214 includes configuring and/or operating the second circulation circuit in a cleaning mode. The cleaning mode may be operated after the working mode. In the cleaning mode, the second fluid flow may include a gas flow. In some embodiments, operating the second circulation circuit in the cleaning mode includes circulating, using the pump, the second fluid flow from the second port of the second circulation circuit, through the liquid-gas separation device, and out of the first port of the second circulation circuit. In some embodiments, operating the second circulation circuit in the cleaning mode includes transporting residual reaction medium in the liquid-gas separation device back to the reaction chamber. The cleaning mode may prepare the liquid-gas-separation device for the next working mode, such as by drying a separation membrane of the liquid-gas separation device.

In the cleaning mode, the second fluid flow may be circulated at any suitable flow rate, such as a flow rate ranging from about 0.25 L/min to about 0.5 L/min, from about 0.5 L/min to about 1.0 L/min, from about 1.0 L/min to about 3.0 L/min, from about 3.0 L/min to about 5.0 L/min, or a combination thereof. The second circulation circuit may be operated in the cleaning mode for any suitable period, such as for less than about 0.5 minute, less than about 1 minute, less than about 2 minutes, or less than about 5 minutes.

In some embodiments, step 1214 may include configuring a switch valve to a first position to allow the second circulation circuit to operate in the working mode, and may include configuring the switch valve to a second position to allow the second circulation circuit to operate in the cleaning mode.

In some embodiments, step 1214 includes purging the reaction chamber, such as the gas region of the reaction chamber, with the carrier gas. The carrier gas may accumulate in the gas region of the reaction chamber, and may be circulated in the second circulation circuit in the cleaning mode.

In some embodiments, method 1200 includes step 1216. In some embodiments, step 1216 includes conveying the product gas from the reaction chamber through a filtration system. Step 1216 may include, reducing or removing, by the filtration system, one or more impurities in the product gas, such as solid matter (e.g., salt aerosols) and moisture. The filtration system may include one or more filtration devices or filters.

In some embodiments, method 1200 includes step 1218. In some embodiments, step 1218 includes conveying the product gas to a pressure vessel. In some embodiments, step 1218 includes receiving and storing the product gas in the pressure vessel for a pressure-holding period. The pressure and/or NO concentration in the pressure vessel may increase to a predetermined level or a predetermined range at the end of the pressure-holding period. In some embodiments, the pressure vessel includes a first region and a second region. Step 1218 may include receiving the product gas through an inlet in fluid communication with a first region of the pressure vessel. Step 1218 may include storing the product gas in the first region of the pressure vessel. Step 1218 may include releasing the product gas from the pressure vessel, such as through an outlet in fluid communication with the first region. The concentration of NO in the product gas released from the pressure vessel may reach a steady state in a ramp period. A ramp period may refer to a transient period during which NO concentration of the product gas may change from an initial concentration to a predetermined steady state concentration. In some embodiments, step 1218 includes measuring and/or adjusting, using a flow control device, a flow rate of the product gas released from the pressure vessel. The flow control device may adjust the flow rate of the product gas in accordance with instructions received from a control device.

In some embodiments, step 1218 includes receiving and storing the product gas in a second region in fluid communication with the first region. Step 1218 may include storing the product gas in the second region at a pressure that is below or equal to a predetermined threshold. Step 1218 may include releasing the product gas stored in the second region from the second region to the first region, and may further include releasing the product gas out of the pressure vessel from the first region. In some embodiments, step 1218 includes releasing gas from the pressure vessel, such as from the second region of the pressure vessel, through a pressure relief valve when the pressure in one or more regions in the pressure vessel exceeds a predetermined threshold. In some embodiments, step 1218 includes treating the gas released through the pressure relief valve, for example by a waste gas treatment device.

In some embodiments, method 1200 includes step 1220. In some embodiments, step 1220 may include conveying the product gas through a gas converter to reduce or remove one or more toxic nitrogen oxides, such as $NO_2$, in the product gas. In some embodiments, step 1220 includes absorbing or converting, by the gas converter, some or all toxic nitrogen oxides, such as $NO_2$, as the product gas passes therethrough. The toxic nitrogen oxides may be converted to NO. Step 1220 may include conveying the product gas from an inlet, through a circuitous flow path, to an outlet of the gas converter, and may include conveying the product gas through a filter material in the circuitous flow path. Step 1220 may include absorbing, using the filter material, some or all toxic nitrogen oxides in the product gas. Additionally or alternatively, step 1220 may include converting, using the filter material, some or all toxic nitrogen oxides in the product gas to NO.

In some embodiments, method 1200 includes step 1222. In some embodiments, step 1222 includes delivering, using a ventilation circuit, NO or a gas mixture including NO to a patient. The gas mixture may include one or more gas components, such as air, oxygen, moisture. In some embodiments, step 1222 include delivering the NO or the gas mixture to the patient through an inspiratory circuit of the ventilation circuit. In some embodiments, step 1222 include receiving exhaled gas from the patient through an expiratory circuit of the ventilation circuit.

In some embodiments, step 1222 includes delivering NO with a gas flow, such as an air flow or an oxygen flow, supplied by a respiratory device, such as a ventilator, connected to the ventilation circuit. For example, step 1222 may include combining a gas flow, such as an air flow or an oxygen flow, supplied by a respiratory device, such as a ventilator, with a flow of product gas received from an NO system to generate a gas mixture. In some embodiments, step 1222 includes humidifying the gas mixture before delivering the gas mixture to the patient.

In some embodiments, step 1222 includes measuring, using a flow rate sensor, a flow rate of a gas flow, such as an air flow or an oxygen flow, supplied from a respiratory device, such as a ventilator. The flow rate sensor may be in communication with a control device via a wired or wireless connection. Step 1222 may further include sending sensing signals or readings from the flow rate sensor to the control device.

In some embodiments, step 1222 includes measuring, by one or more gas sensors or a gas monitoring device including one or more gas sensors, concentrations of one or more components of the gas mixture to be delivered to the patient. For example, step 1222 may include obtaining a sample gas flow of the gas mixture to be delivered to the patient and measuring the concentration of one or more components of the sample gas flow. The one or more gas sensors or the gas monitoring device may be in communication with a control device via a wired or wireless connection. Step 1222 may include sending sensing signals or readings from the one or more gas sensors or the gas monitoring device to the control device. In some embodiments, step 1222 includes providing an alarm when one or more readings of the one or more gas sensors is above or below a threshold. The alarm may be in any suitable form, such as audible or a visible alarm, for any suitable duration.

In some embodiments, step 1222 includes controlling a flow rate of the product gas to be mixed or combined with a gas flow, such as an air flow or an oxygen flow, supplied by the respiratory device, such as a ventilator. For example, the control device may be in communication with a flow control device configured to control the flow rate of the product gas from the NO system. The control device may send instructions to the flow control device to adjust the flow rate of the product gas. The control device may generate the instructions based on one or more sensing signals or readings of one or more of the flow rate sensors and/or one or more gas sensors.

In some embodiments, step 1222 includes controlling a flow rate of the air flow or oxygen flow supplied by the ventilator. For example, the control device may be in wired or wireless communication with the ventilator. The control device may send instructions to the ventilator to adjust the flow rate of the air flow or oxygen flow.

In some embodiments, step 1222 includes operating a gas monitoring device in one or more operating processes for measuring concentrations of concentrations of one or more components of the gas mixture to be delivered to the patient. For example, step 1222 may include performing one or more of an initialization process, a cleaning process, a sampling process, and a calibration process.

The foregoing descriptions have been presented for purposes of illustration. They are not exhaustive and are not limited to precise forms or embodiments disclosed. Modifications and adaptations of the embodiments will be apparent from consideration of the specification and practice of the disclosed embodiments. For example, the described implementations include hardware, but systems and methods consistent with the present disclosure can be implemented with hardware and software. In addition, while certain components have been described as being connected to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations or alterations based on the present disclosure. Further, the steps of the disclosed methods can be modified in any manner, including reordering steps or inserting or deleting steps.

The features and advantages of the disclosure are apparent from the detailed specification. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

It is appreciated that the above-described embodiments can be implemented by hardware, or software (program codes), or a combination of hardware and software. If implemented by software, it may be stored in the above-described computer-readable media. The software, when executed by the processor can perform at least some of the steps of the disclosed methods.

In the foregoing specification, embodiments have been described with reference to numerous specific details that can vary from implementation to implementation. Certain adaptations and modifications of the described embodiments can be made. Other embodiments can be apparent to those skilled in the art from consideration of the specification and practice of the disclosure disclosed herein. It is intended that the specification and examples be considered as exemplary only, with a true scope and spirit of the disclosure being indicated by the following claims. It is also intended that the sequence of steps shown in figures are only for illustrative purposes and are not intended to imply all steps must be performed for any given method of operation or to be limited to any particular sequence of steps. As such, those skilled in the art can appreciate that these steps can be performed in a different order while implementing the same method. Further, the apparatuses shown in figures are illustrative only and a given apparatus or system may include a different combination of the components or modules of these apparatuses.

The invention claimed is:

1. An apparatus for generating nitric oxide (NO), the apparatus comprising:

a reaction chamber having a liquid region and a gas region, the liquid region configured to contain a reaction medium, the gas region configured to contain a product gas comprising NO;

a plurality of electrodes disposed in the reaction medium, the plurality of electrodes comprising a cathode;

an energy source electrically connected to the plurality of electrodes and configured to apply a predetermined voltage or a predetermined current to the cathode to generate NO;

a sparger disposed in the reaction medium;

an inlet circuit in fluid communication with the sparger and configured to convey a carrier gas to the sparger, wherein the carrier gas preferably comprises nitrogen;

an outlet circuit in fluid communication with the gas region of the reaction chamber and configured to convey the product gas from the reaction chamber; and a recirculation circuit including:

a circulation inlet in fluid communication with the gas region of the reaction chamber, configured to receive a fluid flow of the product gas from the gas region;

a circulation outlet in fluid communication with the sparger; and a pump configured to create the fluid flow of the product gas from the circulation inlet to the sparger through the circulation outlet.

2. The apparatus of claim 1, wherein the fluid flow comprises a flow of the product gas.

3. The apparatus of claim 1, wherein the sparger is disposed adjacent the cathode and configured to emanate bubbles in the reaction medium to propagate along a surface of the cathode.

4. The apparatus of claim 1, wherein the reaction chamber comprises a first side and a second side opposite to the first side, and the cathode comprises an electrode plate positioned substantially perpendicular to the second side of the reaction chamber.

5. The apparatus of claim 4, wherein the electrode plate comprises a surface, a first edge, and a second edge opposite to the first edge, the first edge extending along the first side of the reaction chamber, the second edge extending along the second side of the reaction chamber.

6. The apparatus of claim 5, wherein the sparger is disposed between the second side of the reaction chamber and the second edge of the electrode plate and configured to emanate bubbles along a bubble path extending from the second edge to the first edge of the electrode plate.

7. The apparatus of claim 1, wherein the reaction medium comprises a buffer solution, a source of nitrite ions, and a catalyst.

8. The apparatus of claim 1, wherein the predetermined voltage is from about 1 V to about 5.0V.

9. The apparatus of claim 1, further comprising a pressure vessel in fluid communication with the outlet circuit, the pressure vessel configured to receive the product gas from the outlet circuit, store the received product gas at or below a predetermined pressure, and release the received product gas, wherein the pressure vessel comprises:

a body defining an interior cavity comprising a first region and a second region, the second region in fluid communication with and disposed downstream of the first region;

a gas inlet and a gas outlet in fluid communication with the first region; and a plurality of baffles defining a circuitous flow path through the first region and the second region; and a pressure relief valve disposed on the body and in fluid communication with the second region.

10. The apparatus of claim 1, further comprising a filtration device disposed downstream of the circulation inlet and upstream of the pump of the recirculation circuit, the filtration device configured to reduce or remove one or more liquid and/or solid impurities in the fluid flow.

11. The apparatus of claim 1, further comprising a carrier gas source disposed upstream of and in fluid communication with the inlet circuit, the carrier gas source configured to generate or supply the carrier gas to the inlet circuit.

12. The apparatus of claim 1, further comprising:

a pressure vessel in fluid communication with the outlet circuit, the pressure vessel configured to receive the product gas from the outlet circuit, store the received product gas at or below a predetermined pressure, and release the received product gas, and a ventilation circuit configured to connect to a respiratory device, the ventilation circuit comprising an inspiratory circuit disposed downstream of and in fluid communication with the respiratory device and the pressure vessel.

13. The apparatus of claim 12, wherein the inspiratory circuit comprises:

an inlet configured to receive an air flow or an oxygen flow from the respiratory device;

a port disposed downstream of the inlet, the port configured to receive the product gas from the pressure vessel;

a flow rate sensor disposed downstream of the inlet and configured to measure a flow rate of the air flow or the oxygen flow; and an outlet configured to deliver a gas mixture comprising the product gas from the pressure vessel and the air or oxygen from the respiratory device.

14. The apparatus of claim 13, wherein the inspiratory circuit further comprises a sampling port disposed upstream of the outlet and configured to output a sample gas flow of the gas mixture.

15. The apparatus of claim 14, further comprising a gas monitoring device comprising one or more gas sensors configured to receive the sample gas flow and measure one or more concentrations of $NO_2$, NO, and $O_2$ of the sample gas flow.

16. The apparatus of claim 15, further comprising:

a flow control device configured to control a flow rate of the product gas entering the inspiratory circuit from the pressure vessel;

a control device in communication with the flow rate sensor, the flow control device, and the gas monitoring device, wherein the control device is configured to receive one or more sensing signals or readings from the gas monitoring device and/or the flow rate sensor;

generate instructions based on the one or more sensing signals or readings; and send the instructions to the flow control device to adjust the flow rate of the product gas entering the inspiratory circuit.

17. A method for generating nitric oxide (NO), the method comprising:

applying, by an energy source, a predetermined voltage or a predetermined current to a plurality of electrodes disposed in a reaction medium contained in a reaction chamber to generate NO, the plurality of electrodes comprising a cathode, the reaction chamber comprising a gas region and a liquid region, the liquid region configured to contain the reaction medium, the gas region configured to contain a product gas comprising NO;

receiving a carrier gas through an inlet circuit in fluid communication with a sparger disposed in the reaction medium;

emanating, by the sparger, bubbles of the carrier gas in the reaction medium to sweep a surface of one or more of the plurality of electrodes; and conveying the product gas from the reaction chamber through an outlet circuit, the outlet circuit in fluid communication with the gas region of the reaction chamber, wherein at least a portion of the product gas is circulated, in a recirculation circuit, back to the sparger in the reaction chamber.

18. The method of claim 17, wherein the portion of the product gas is circulated from the gas region of the reaction chamber, by a pump in the recirculation circuit, to the sparger.

19. The method of claim 18, further comprising combining the circulated product gas with the carrier gas upstream of the sparger.

20. The method of claim 17, further comprising before applying the predetermined voltage or the predetermined current, applying a stimulation voltage or a stimulation current to at least one of the plurality of electrodes for a stimulation period, wherein when the stimulation voltage is applied, the stimulation voltage has a magnitude greater than the predetermined voltage, and when the stimulation current is applied, the stimulation current has a magnitude greater than the predetermined current.

21. An apparatus for generating nitric oxide (NO), the apparatus comprising:

a reaction chamber having a liquid region and a gas region, the liquid region configured to contain a reaction medium, the gas region configured to contain a product gas comprising NO;

a plurality of electrodes disposed in the reaction medium, the plurality of electrodes comprising a cathode;

an energy source electrically connected to the plurality of electrodes and configured to apply a predetermined voltage or a predetermined current to the cathode to generate NO;

a sparger disposed in the reaction medium;

an inlet circuit in fluid communication with the sparger and configured to convey a carrier gas to the sparger, wherein the carrier gas preferably comprises nitrogen;

an outlet circuit in fluid communication with the gas region of the reaction chamber and configured to convey the product gas from the reaction chamber; and a pressure vessel in fluid communication with the outlet circuit, the pressure vessel configured to receive the product gas from the outlet circuit, store the received product gas at or below a predetermined pressure, and release the received product gas.

* * * * *